US012404346B2

(12) United States Patent
Sharma et al.

(10) Patent No.: US 12,404,346 B2
(45) Date of Patent: Sep. 2, 2025

(54) ANTI-NALOXONE AND ANTI-NALTREXONE MONOCLONAL ANTIBODIES AND METHODS OF PRODUCTION AND USE THEREOF

(71) Applicant: Siemens Healthcare Diagnostics Inc., Tarrytown, NY (US)

(72) Inventors: Manoj Sharma, Hockessin, DE (US); Tatiana Lebedeva, Aston, PA (US); Tatiana Mareeva, Haddonfield, NJ (US); Yuriy Smirnov, Haddonfield, NJ (US); Bogdan Draghici, Newark, DE (US); Zhu Teng, Garnet Valley, PA (US); Yi Feng Zheng, Wilmington, DE (US); Heungyeung Yau, Wilmington, DE (US); Nihmat Morjana, Newark, DE (US); William Bedzyk, Odessa, DE (US); Allison Dominowski, Middletown, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 871 days.

(21) Appl. No.: 17/310,042

(22) PCT Filed: Jan. 30, 2020

(86) PCT No.: PCT/US2020/015773
§ 371 (c)(1),
(2) Date: Jul. 13, 2021

(87) PCT Pub. No.: WO2020/160199
PCT Pub. Date: Aug. 6, 2020

(65) Prior Publication Data
US 2022/0049018 A1      Feb. 17, 2022

Related U.S. Application Data

(60) Provisional application No. 62/820,400, filed on Mar. 19, 2019, provisional application No. 62/799,399, filed on Jan. 31, 2019.

(51) Int. Cl.
*C07K 16/44* (2006.01)
*A61K 47/64* (2017.01)
(Continued)

(52) U.S. Cl.
CPC ............ *C07K 16/44* (2013.01); *A61K 47/643* (2017.08); *A61P 25/36* (2018.01);
(Continued)

(58) Field of Classification Search
CPC .............. C07K 16/44; C07K 2317/10; C07K 2317/565; C07K 2317/76; A61K 47/643; A61P 25/36; G01N 33/94
See application file for complete search history.

(56) References Cited

U.S. PATENT DOCUMENTS

| 7,241,873 B2 * | 7/2007 | Uede ................ A61P 37/00 |
| | | 530/387.3 |
| 2005/0152899 A1 | 7/2005 | Kinch et al. |

(Continued)

FOREIGN PATENT DOCUMENTS

| CN | 101426521 | 5/2009 |
| CN | 108368177 | 9/2018 |

(Continued)

OTHER PUBLICATIONS

Lloyd et al., "Modelling the human immune response: performance of a 10e11 human antibody repertoire against a broad panel of therapeutically relevant antigens", Protein Engineering, Design and Selection, vol. 22, Issue 3, Mar. 1, 2009, pp. 159-168. (Year: 2009).*
Brown et al., "Tolerance of single, but not multiple, amino acid replacements in antibody VH CDR 2: a means of minimizing B cell wastage from somatic hypermutation?", J Immunol. May 1996;156(9):3285-91. (Year: 1996).*
Vajdos et al.,"Comprehensive functional maps of the antigen-binding site of an anti-ErbB2 antibody obtained with shotgun scanning mutagenesis" J Mol Biol. Jul. 5, 2002;320(2):415-28, DOI: 10.1016/S0022-2836(02)00264-4). (Year: 2002).*
International Search Report for PCT/US2020/015773 dated Jun. 22, 2020.

(Continued)

*Primary Examiner* — Gregory S Emch
*Assistant Examiner* — Nam P Nguyen

(57) ABSTRACT

Antibodies that specifically bind naloxone or naltrexone are disclosed. Also disclosed are conjugates used in the production of the antibodies, as well as methods of producing the antibodies. Also disclosed are methods of using the antibodies in direct assays for naloxone or naltrexone. Further disclosed are methods of reducing naloxone or naltrexone interference in opiate assays using the antibodies.

(Continued)

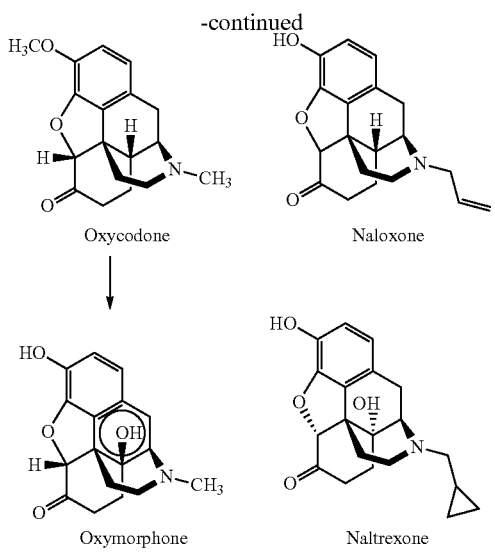

18 Claims, 22 Drawing Sheets

Specification includes a Sequence Listing.

(51) Int. Cl.
  *A61P 25/36* (2006.01)
  *G01N 33/94* (2006.01)
(52) U.S. Cl.
  CPC .... *C07K 2317/10* (2013.01); *C07K 2317/565* (2013.01); *G01N 33/94* (2013.01)

(56) References Cited

U.S. PATENT DOCUMENTS

| | | | |
|---|---|---|---|
| 2008/0292639 A1 | 11/2008 | Shen et al. | |
| 2012/0115244 A1 | 5/2012 | Adamczyk et al. | |
| 2015/0259409 A1 | 9/2015 | Chen et al. | |
| 2017/0362579 A1* | 12/2017 | Zheng | C12N 9/0006 |
| 2018/0258168 A1* | 9/2018 | Westerman | G01N 33/6893 |
| 2018/0312574 A1 | 11/2018 | Crowe et al. | |

FOREIGN PATENT DOCUMENTS

| | | | |
|---|---|---|---|
| CN | 108517014 | 9/2018 | |
| FR | 2859633 | 9/2004 | |
| FR | 2859633 A1 * | 3/2005 | ......... A61K 39/0013 |
| RU | 2635517 | 11/2017 | |
| WO | 98/26644 | 6/1998 | |
| WO | WO-9826644 A2 * | 6/1998 | |
| WO | 0170031 | 9/2001 | |
| WO | 2016100113 | 6/2016 | |
| WO | 2018195302 | 10/2018 | |

OTHER PUBLICATIONS

Berkowitz, Dr Barry et al: "Disposition of Naloxone: Use of a New Radioimmunoassay"; The Journal of Pharmacology and Experimental Therapeutics Copyright; vol. 195; pp. 499-504; (1975).
Lowry P et al: "Development of antibodies for the sensitive detection of zaleplon and related compounds"; Clinical Chemistry; Oxford University Press; vol. 55; No. 6, suppl; pp. A257; (2009).
Anonymous: "Toxicology Solutions"; XP055898913; www.randoxtoxicology.com/wp-content/uploads/2018/11/LT193TOX-Toxicology-Solutions-LQ-APR18.pdf / Jan. 4, 2018.
Usagawa Takoshi et al: "Characterization of morphine-specific monoclonal antibodies showing minimal cross-reactivity with codeine"; Journal of Immunological Methods; Elsevier; Science Publishers B.V.; Amsterdam; vol. 157; No. 1-2; pp. 143-148; (1993).
Cavanagh, Kevin et al: "Assessment of the EMIT technique as a screening test for opiates and methadone for a methadone maintenance clinic and its calibration by bayesian statistics"; Clinical Biochemistry; vol. 11; No. 5; pp. 210-213; (1978).
Wiencek Joseph R. et al: "Rapid Assessment of Drugs of Abuse" In: "Advances in Clinical Chemistry", Jan. 1, 2017 (Jan. 1, 2017), Saint Louis: Elsevier Science, US, XP055648282, ISBN: 978-0-128120750-0, vol. 80, pp. 193-225.
Saitman A. et al: False-Positive Interferences of Common Urine Drug Screen Immunoassays: A Review* , Journal of Analytical Toxicology, vol. 38, No. 7, Jul. 1, 2014 (Jul. 1, 2014), pp. 387-396.
Plant Elizabeth et al: "False Positive Urine Drug Screens in Patients Receiving Oral Naltrexone". Canadian Journal of Addiction, vol. 10, No. 2, Jun. 1, 2019 (Jun. 1, 2019), pp. 25-26, XP093287317, ISSN: 2368-472.
Milone Michael G: "Laboratory Testing for Prescription Opiods" Journal of Medical Toxicology, Springer US, New York, vol. 8, No. 1, Dec. 1, 2012 (Dec. 1, 2012), pp. 408-416.
Collinson Paul O et al: "Assay Imprecision and 99th-Percentile Reference Value of a High-Sensitivity Cardiac Troponin I Assay", Clinical Chemistry, vol. 55, No. 7, Jul. 1, 2009 (Jul. 1, 2009), pp. 1433-1434.

* cited by examiner

BD103715436-6
naloxone-3-Val-mcKLH

BD103715436-5
naltrexone-3-Val-mcKLH

Hydrocodone Assay (Ab 9C8)

| Naltrexone 3D3 Loading (mg/mL) | 0.00 | 0.60 |
|---|---|---|
| Cal Level (ng/mL) | Rate (mA/min) | Rate (mA/min) |
| 0 | 313 | 308 |
| 100 | 350 | 346 |
| 300 | 467 | 464 |
| 500 | 551 | 536 |
| 1000 | 639 | 603 |
| Total Curve | 326 | 295 |

| Cutoff (mA/min) | | 467 | 464 |
|---|---|---|---|
| Calibration curve | | Hydrocodone | Hydrocodone |
| Naloxone 1,000 ng/mL | Mean | 725 | 388 |
| | Conc. ng/mL | >1000 | 167 |
| | Pos/Neg | Pos | Neg |
| Naloxone 2,500 ng/mL | Mean | 742 | 463 |
| | Conc. ng/mL | >1000 | 298 |
| | Pos/Neg | Pos | Neg |
| Naltrexone 2,500 ng/mL | Mean | 750 | 362 |
| | Conc. ng/mL | >1000 | 126 |
| | Pos/Neg | Pos | Neg |
| Naltrexone 5,000 ng/mL | Mean | 743 | 416 |
| | Conc. ng/mL | >1000 | 211 |
| | Pos/Neg | Pos | Neg |

Hydrocodone Assay (Ab 7F9)

| Naltrexone 3D3 Loading (mg/mL) | 0.00 | 0.40 |
|---|---|---|
| Cal Level (ng/mL) | Rate (mA/min) | Rate (mA/min) |
| 0 | 361 | 365 |
| 100 | 396 | 401 |
| 300 | 510 | 517 |
| 500 | 642 | 632 |
| 1000 | 726 | 690 |
| Total Curve | 365 | 325 |

| Cutoff (mA/min) | | 510 | 517 |
|---|---|---|---|
| Calibration curve | | Hydrocodone | Hydrocodone |
| Naloxone 1,000 ng/mL | Mean | 731 | 443 |
| | Conc. ng/mL | >1000 | 189 |
| | Pos/Neg | Pos | Neg |
| Naloxone 2,500 ng/mL | Mean | 752 | 509 |
| | Conc. ng/mL | >1000 | 278 |
| | Pos/Neg | Pos | Neg |
| Naltrexone 2,500 ng/mL | Mean | 755 | 401 |
| | Conc. ng/mL | >1000 | 123 |
| | Pos/Neg | Pos | Neg |
| Naltrexone 5,000 ng/mL | Mean | 759 | 432 |
| | Conc. ng/mL | >1000 | 174 |
| | Pos/Neg | Pos | Neg |

FIG. 11

| Hydrocodone Assay (Ab 9C8) | | |
|---|---|---|
| Naloxone 6H6 Loading (mg/mL) | 0.00 | 0.25 |
| Cal Level (ng/mL) | Rate (mA/min) | |
| 0 | 343 | 337 |
| 100 | 383 | 371 |
| 300 | 506 | 459 |
| 500 | 601 | 510 |
| 1000 | 699 | 551 |
| Total Curve | 356 | 215 |

| Hydrocodone Assay (Ab 7F9) | | |
|---|---|---|
| Naloxone 6H6 Loading (mg/mL) | 0.00 | 0.25 |
| Cal Level (ng/mL) | Rate (mA/min) | |
| 0 | 361 | 351 |
| 100 | 394 | 377 |
| 300 | 508 | 450 |
| 500 | 657 | 512 |
| 1000 | 760 | 539 |
| Total Curve | 399 | 188 |

| Cutoff (mA/min) | | 506 | 459 |
|---|---|---|---|
| Calibration curve | | Hydrocodone | |
| Naloxone 500 ng/mL | Mean | 761 | 442 |
| | Conc. ng/mL | >1000 | 251 |
| | Pos/Neg | Pos | Neg |
| Naloxone 1,000 ng/mL | Mean | 801 | 519 |
| | Conc. ng/mL | >1000 | 568 |
| | Pos/Neg | Pos | Pos |
| Naltrexone 500 ng/mL | Mean | 798 | 535 |
| | Conc. ng/mL | >1000 | 713 |
| | Pos/Neg | Pos | Pos |
| Naltrexone 1,000 ng/mL | Mean | 816 | 628 |
| | Conc. ng/mL | >1000 | >1000 |
| | Pos/Neg | Pos | Pos |

| Cutoff (mA/min) | | 508 | 450 |
|---|---|---|---|
| Calibration curve | | Hydrocodone | |
| Naloxone 500 ng/mL | Mean | 680 | 441 |
| | Conc. ng/mL | >1000 | 260 |
| | Pos/Neg | Pos | Neg |
| Naloxone 1,000 ng/mL | Mean | 770 | 469 |
| | Conc. ng/mL | >1000 | 338 |
| | Pos/Neg | Pos | Pos |
| Naltrexone 500 ng/mL | Mean | 691 | 462 |
| | Conc. ng/mL | >1000 | 317 |
| | Pos/Neg | Pos | Pos |
| Naltrexone 1,000 ng/mL | Mean | 778 | 506 |
| | Conc. ng/mL | >1000 | 502 |
| | Pos/Neg | Pos | Pos |

FIG. 12

Hydrocodone Assay (Ab 9C8)

| | Naltrexone 2A12 Loading (mg/mL) | |
|---|---|---|
| | 0.00 | 0.40 |
| Cal Level (ng/mL) | Rate (mA/min) | Rate (mA/min) |
| 0 | 343 | 345 |
| 100 | 386 | 394 |
| 300 | 510 | 519 |
| 500 | 599 | 599 |
| 1000 | 686 | 675 |
| Total Curve | 343 | 330 |

| Cutoff (mA/min) | 510 | 519 |
|---|---|---|
| Calibration curve | Hydrocodone | |
| Naloxone 5,000 ng/mL | Mean Conc. ng/mL | 819 |
| | Pos/Neg | >1000 |
| | | Pos |
| Naltrexone 10,000 ng/mL | Mean Conc. ng/mL | 819 |
| | Pos/Neg | >1000 |
| | | Pos |

| Calibration curve | Hydrocodone | |
|---|---|---|
| Naloxone 5,000 ng/mL | Mean Conc. ng/mL | 514 |
| | | 288 |
| | Pos/Neg | Neg |
| Naltrexone 10,000 ng/mL | Mean Conc. ng/mL | 414 |
| | | 131 |
| | Pos/Neg | Neg |

Hydrocodone Assay (Ab 7F9)

| | Naltrexone 2A12 Loading (mg/mL) | |
|---|---|---|
| | 0.00 | 0.40 |
| Cal Level (ng/mL) | Rate (mA/min) | Rate (mA/min) |
| 0 | 356 | 361 |
| 100 | 392 | 403 |
| 300 | 503 | 529 |
| 500 | 667 | 660 |
| 1000 | 739 | 716 |
| Total Curve | 383 | 356 |

| Cutoff (mA/min) | 503 | 529 |
|---|---|---|
| Calibration curve | Hydrocodone | |
| Naloxone 5,000 ng/mL | Mean Conc. ng/mL | 819 |
| | | >1000 |
| | Pos/Neg | Pos |
| Naltrexone 10,000 ng/mL | Mean Conc. ng/mL | 819 |
| | | >1000 |
| | Pos/Neg | Pos |

| Calibration curve | Hydrocodone | |
|---|---|---|
| Naloxone 5,000 ng/mL | Mean Conc. ng/mL | 514 |
| | | 288 |
| | Pos/Neg | Neg |
| Naltrexone 10,000 ng/mL | Mean Conc. ng/mL | 414 |
| | | 131 |
| | Pos/Neg | Neg |

FIG. 13

ANTI-NALOXONE AND ANTI-NALTREXONE MONOCLONAL ANTIBODIES AND METHODS OF PRODUCTION AND USE THEREOF

CROSS REFERENCE TO RELATED APPLICATIONS/INCORPORATION BY REFERENCE STATEMENT

Not Applicable.

STATEMENT REGARDING FEDERALLY SPONSORED RESEARCH OR DEVELOPMENT

Not Applicable.

BACKGROUND

Naloxone is commonly used as an antagonist of abused opioids, typically in drug overdose cases. Naloxone is a life-saving, short acting drug that will bring a patient out of an opiate overdose by stripping the opiate from the opiate receptor. Patients are given repeated shots of naloxone (NARCAN® (naloxone HCl), ADAPT Pharma, Inc., Radnor, PA) to saturate drug receptors so that the pharmacological response to abused opioids is minimized. Naloxone acts within minutes and lasts for about an hour.

Naltrexone is another commonly used opioid antagonist drug that is also used in alcohol abuse cases; naltrexone is an opiate/alcohol blocking agent that has been used for the last 30 years. Naltrexone acts slowly and lasts longer than naloxone. VIVITROL® (Alkermes, Inc., Dublin, Ireland) is an extended release form of naltrexone. The extended release properties of VIVITROL® assist with patient compliance, since daily use is not required.

Both naloxone and naltrexone will also blunt the effects of alcohol, and as such, they are often used after discharge from a residential treatment program to prevent alcohol relapse.

Naloxone has a rapid distribution throughout the body. The mean serum half-life has been shown to range from 30 to 81 minutes, which is shorter than the average half-life of some opiates, and which necessitates repeat dosing if opioid receptors must be stopped from triggering for an extended period of time. Naloxone is primarily metabolized by the liver; its major metabolite is naloxone-3-glucuronide, which is excreted in the urine.

Naltrexone is metabolized in the liver mainly to 6β-naltrexol by the enzyme dihydrodiol dehydrogenase. Other metabolites include 2-hydroxy-3-methoxy-6β-naltrexol and 2-hydroxy-3-methoxy-naltrexone. These intermediates are then further metabolized by conjugation with glucuronide. The plasma half-life of naltrexone and its metabolite 6β-naltrexol are about four (4) and thirteen (13) hours, respectively.

Randox Toxicology (Crumlin, United Kingdom) offers a naloxone assay based on BioChip Array Technology (BAT) that is based on Enzyme-Linked Immunosorbent Assay (ELISA) principles. Biochip Array Technology is a precision multiplex testing platform allowing for the simultaneous quantitative or qualitative detection of a wide range of analytes from a single sample. The Biochip is a solid-state device with discrete test sites onto which antibodies specific to different drug compounds are immobilized and stabilized. Competitive chemiluminescent immunoassays are then employed, offering a highly sensitive screen. However, for this assay, the level of naltrexone cross-reactivity is 12.5%, and the level of naloxone 3-B-D glucuronide cross-reactivity is 70.6%.

Immunalysis Corporation (Pomona, CA) offers an ELISA Naltrexone assay for oral fluid and forensic use and also based on ELISA principles (see, for example, catalog numbers 239-0096 and 239-0480).

Neogen Corporation (Lansing, MI) offers a Naltrexone/Nalbuphine ELISA kit that is a qualitative one-step kit designed for use as a screening device for the detection of naltrexone, nalbuphine, and/or other metabolites. This test, however, has only 4% cross-reactivity to naloxone (see, for example, catalog numbers 133015 and 133019).

Other methods of detecting naloxone and naltrexone involve High Performance Liquid Chromatography/Tandem Mass Spectrometry (LC-MS/MS) analysis. For example, NMS Labs (Willow Grove, PA) offer LC-MS/MS analyses for naltrexone (total) and the metabolite 6-beta-naltrexol (total) in urine (see, for example, Test Code 3116U, Test Name Naltrexone and Metabolite—Total (Conjugated/Unconjugated), Urine).

However, there are currently no known homogeneous immunoassays available to either or both of these two drugs. Thus, there is a need in the art for monoclonal antibodies that specifically bind to naloxone and/or naltrexone, as well as homogeneous immunoassays that can be utilized to detect the presence of these drugs in a biological sample and/or provide a qualitative screening and/or a quantitative clinical measurement thereof.

In addition, given the similar structure of naloxone and naltrexone to various opiates (see FIG. 1), these drugs can cross-react in various opiate assays. In particular, it is commonly observed that various opiate assays provide false positive results for patients undergoing naloxone/naltrexone treatment. Thus, there is also a need in the art to neutralize naloxone and naltrexone present in biological samples to thereby prevent any false positive or falsely elevated opiate measurements, thus providing more accurate qualitative screenings and quantitative measurements in clinical opiate assays.

BRIEF DESCRIPTION OF THE DRAWINGS

FIG. 11 illustrates an evaluation of the monoclonal antibody 180A 3D3 in an opiate enzyme multiplied immunoassay.

FIG. 12 illustrates an evaluation of the monoclonal antibody 179A 6H6 in an opiate enzyme multiplied immunoassay.

FIG. 13 illustrates an evaluation of the monoclonal antibody 180C 2A12 in an opiate enzyme multiplied immunoassay.

DETAILED DESCRIPTION

Figure 1:
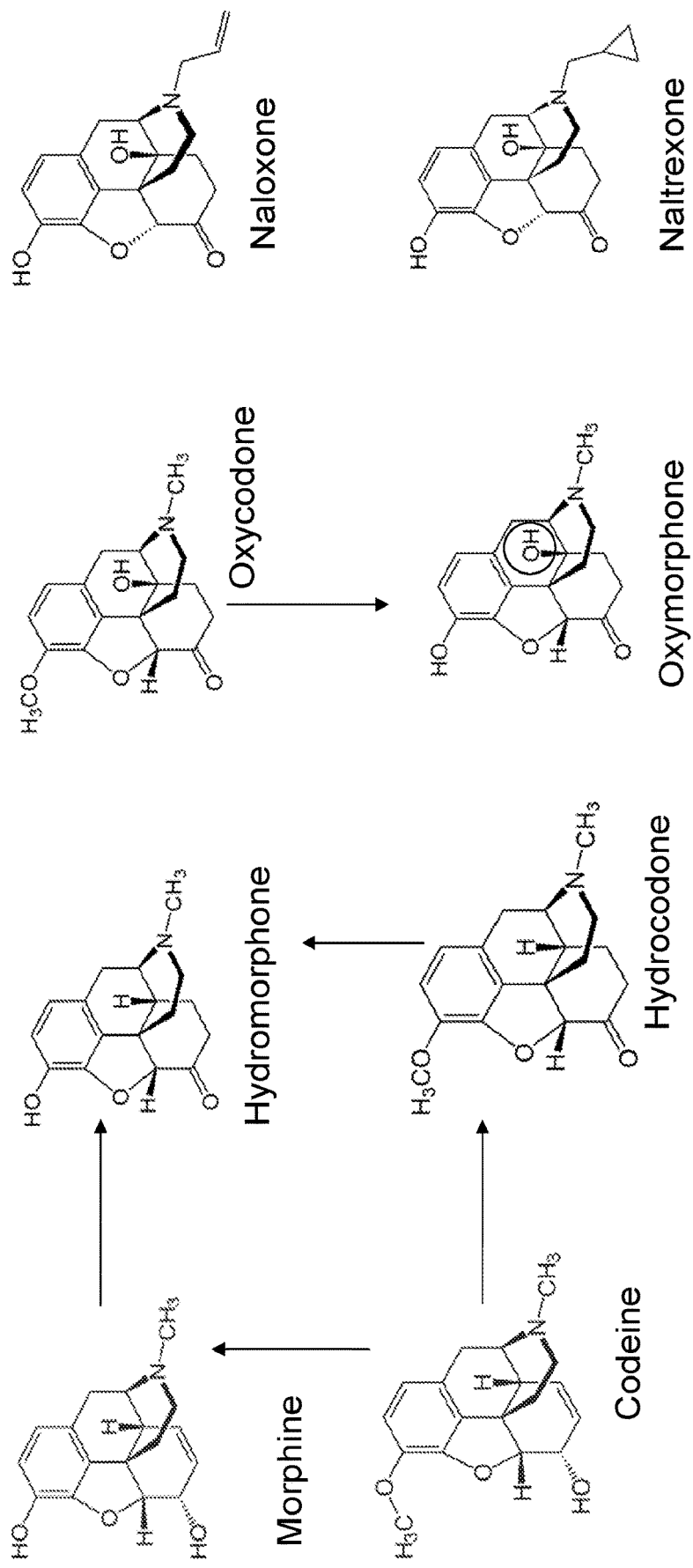
FIG. 1 depicts the chemical structures of naloxone and naltrexone as well as of various opiates with which naloxone and naltrexone cross-react in various opiate assays.

Before explaining at least one embodiment of the present disclosure in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual ($2^{nd}$ ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions, kits, and/or methods disclosed herein can be made and executed without undue experimentation in light of the present disclosure. While the compositions, kits, and/or methods have been described in terms of particular embodiments, it will be apparent to those of skill in the art that variations may be applied to the compositions, kits, and/or methods and in the steps or in the sequence of steps of the methods described herein without departing from the concept, spirit, and scope of the present disclosure. All such similar substitutes and modifications apparent to those skilled in the art are deemed to be within the spirit, scope, and concept of the present disclosure as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The terms "analog" and "derivative" are used herein interchangeably and refer to a substance which comprises the same basic carbon skeleton and carbon functionality in its structure as a given compound, but can also contain one or more substitutions thereto. The term "substitution" as used herein will be understood to refer to the replacement of at least one substituent on a compound with a residue R. In certain non-limiting embodiments, R may include H, hydroxyl, thiol, a halogenid selected from fluoride, chloride bromide or iodite, a C1-C4 compound selected one of the following: linear, branched or cyclic alkyl, optionally substituted, and linear branched or cyclic alkenyl, wherein the optional substitutents are selected from one or more alkenylalkyl, alkynylalkyl, cycloalkyl, cycloalkenylalkyl, arylalkyl, heteroarylalkyl, heterocyclealkyl, optionally substituted heterocycloalkenylalkyl, arylcycloalkyl, and arylheterocycloalkyl, each of which is optionally substituted wherein the optional substitutents are selected from one or more of alkenylalkyl, alkynylalkyl, cycloalkyl, cyclalkenylalkyl, arylalkyl, alkylaryl, heteroarylalkyl, heterocyclealkyl, optionally substituted heterocycloalkenylalkyl, arylcycloalkyl, and arylheterocyclalkyl, phenyl, cyano, hydroxyl, alkyl, aryl, cycloalkyl, cyano, alkoxy, alkylthio, amino, —NH (alkyl), —NH(cycloalkyl)$_2$, carboxy, and —C(O))-alkyl.

The term "sample" as used herein will be understood to include any type of biological sample that may be utilized in accordance with the present disclosure. Examples of fluidic biological samples that may be utilized include, but are not limited to, whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, combinations thereof, and the like.

The term "specific binding partner," as used herein, will be understood to refer to any molecule capable of specifically associating with a macrophilin-binding pharmaceutical for purposes of detection thereof. For example, but not by way of limitation, the specific binding partner may be an antibody, a receptor, a ligand, an aptamer, a molecular imprinted polymer (i.e., inorganic matrices), or any combination and/or derivative(s) thereof, as well as any other molecules capable of specific binding to the macrophilin-binding pharmaceutical.

The term "antibody" is used herein in the broadest sense and refers to, for example, intact monoclonal antibodies and polyclonal antibodies, multi-specific antibodies (e.g., bispecific antibodies), antibody fragments and conjugates thereof that exhibit the desired biological activity of analyte binding (such as, but not limited to, Fab, Fab', F(ab')2, Fv, scFv, Fd, diabodies, single-chain antibodies, and other antibody fragments and conjugates thereof that retain at least a portion of the variable region of an intact antibody), antibody substitute proteins or peptides (i.e., engineered binding proteins/peptides), and combinations or derivatives thereof. The antibody can be of any type or class (e.g., IgG, IgE, IgM, IgD, and IgA) or sub-class (e.g., IgG1, IgG2, IgG2a, IgG2b, IgG3, IgG4, IgA1, and IgA2).

The terms "peptide," "polypeptide," and "protein" are used herein to refer to a polymer of amino acid residues. The term "polypeptide" as used herein is a generic term to refer to native protein, protein fragments, or analogs of a polypeptide sequence. Hence, native protein, protein fragments, and analogs are species of the polypeptide genus. The term "isolated peptide/polypeptide/protein" as used herein refers to a peptide/polypeptide/protein of cDNA, recombinant RNA, or synthetic origin or some combination thereof, which by virtue of its origin, or source of derivation, the "isolated peptide/polypeptide/protein": (1) is not associated with peptides/polypeptides/proteins found in nature, (2) is free of other peptides/polypeptides/proteins from the same source, e.g., free of murine proteins, (3) is expressed by a cell from a different species, and/or (4) does not occur in nature.

As used herein, the term "amino acid" embraces all molecules, whether natural or synthetic, which include both an amino functionality and an acid functionality and capable of being included in a polymer of naturally-occurring amino acids. Exemplary amino acids include naturally-occurring amino acids; analogs, derivatives, and congeners thereof; amino acid analogs having variant side chains; and all stereoisomers of any of any of the foregoing.

The terms "polynucleotide" and "nucleic acid" are used interchangeably. They refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component. The terms "isolated nucleic acid" and "isolated polynucleotide" are used interchangeably; a nucleic acid or polynucleotide is considered "isolated" if it: (1) is not associated with all or a portion of a polynucleotide in which the "isolated polynucleotide" is found in nature, (2) is linked to a polynucleotide to which it is not linked in nature, or (3) does not occur in nature as part of a larger sequence.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby be replicated along with the host genome. Moreover, certain vectors are capable of directing the expression of genes. Such vectors are referred to herein as "recombinant expression vectors" (or simply, "expression vectors").

The term "naturally-occurring" as used herein as applied to an object refers to the fact that an object can be found in nature. For example, a polynucleotide or polypeptide sequence that is present in an organism (including viruses) that can be isolated from a source in nature and which has not been intentionally modified by man in the laboratory or otherwise is naturally-occurring. The term "naturally-occurring" may be used interchangeably herein with the term "native."

The term "selectively hybridize" referred to herein means to detectably and specifically bind. Polynucleotides, oligonucleotides and fragments thereof encoding peptides/polypeptides/proteins in accordance with the inventive concept(s) selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the inventive concept(s) and a nucleic acid sequence of interest will be at least 80%, and more typically with increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred (but non-limiting), with 2 or less being more preferred (but non-limiting). Alternatively, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA."

The following terms are used to describe the sequence relationships between two or more polynucleotide or amino acid sequences: "reference sequence," "comparison window," "sequence identity," "percentage of sequence identity," and "substantial identity." A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window," as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Adv. Appl. Math., 2:482 (1981)), by the homology alignment algorithm of Needleman and Wunsch (J. Mol. Biol., 48:443 (1970)), by the search for similarity method of Pearson and Lipman (Proc. Natl. Acad. Sci. (U.S.A.), 85:2444 (1988)), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages, or by inspection, and the best alignment (i.e., resulting in the highest percentage of homology over the comparison window) generated by the various methods is selected.

The term "sequence identity" means that two polynucleotide or amino acid sequences is identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, such as at least 90 to 95 percent sequence identity, or at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present disclosure. Examples of unconventional amino acids include: 4-hydroxyproline, α-carboxyglutamate, ε-N,N,N-trimethyllysine, ε-N-acetyllysine, O-phosphoserine, N-acetylserine, N-formyl-methionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, such as at least 90 percent sequence identity, or at least 95 percent sequence identity, or at least 99 percent sequence identity. In certain particular (but non-limiting) embodiments, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Particular conservative amino acids substitution groups are: valine-leucine-isoleucine, phenylalanine-tyrosine, lysine-arginine, alanine-valine, glutamic-aspartic, and asparagine-glutamine.

The term "variant" of a reference polypeptide refers to a polypeptide having one or more amino acid substitutions, deletions or insertions relative to the reference polypeptide. An amino acid substitution may be "conservative" or "non-conservative." A "conservative" amino acid substitution refers to the substitution of an amino acid in a polypeptide with another amino acid having similar properties, such as but not limited to, size and charge. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More particular families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. In particular (but non-limiting) embodiments, computerized comparison methods are used to identify sequence motifs or predicted protein conformation domains that occur in other proteins of known structure and/or function. Methods to identify protein sequences that fold into a known three-dimensional structure are known (Bowie et al., Science, 253:164 (1991)). Thus, the foregoing examples demonstrate that those of skill in the art can recognize sequence motifs and structural conformations that may be used to define structural and functional domains in accordance with the present disclosure.

Preferred amino acid substitutions are those which: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various mutations of a sequence other than the naturally-occurring peptide sequence. For example, single or multiple amino acid substitutions (such as, but not limited to, conservative amino acid substitutions) may be made in the naturally-occurring sequence (such as, but not limited to, in the portion of the polypeptide outside the domain(s) forming intermolecular contacts). A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure© (Branden and J. Tooze, eds., Garland Publishing, New York, N.Y. (1991)); and Thornton et al. (Nature 354:105 (1991)), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence. A polypeptide fragment may be any length that is less than the length of the reference polypeptide.

The term "antibody" is used in the broadest sense, and specifically covers monoclonal antibodies (including full length monoclonal antibodies), polyclonal antibodies, multispecific antibodies (e.g., bispecific antibodies), and antibody fragments so long as they exhibit the desired biological activity. Thus, the terms "Antibody" or "antibody peptide(s)" refer to a full length immunoglobulin molecule (i.e., an intact antibody), or a binding fragment thereof that competes with the intact antibody for specific antigen binding. Binding fragments may be produced by recombinant DNA techniques, or by enzymatic or chemical cleavage of intact antibodies. Binding fragments include Fab, Fab', F(ab')$_2$, Fv, scFv, disulfide linked Fv, Fd, diabodies, single-chain antibodies, single domain antibodies (such as but not limited to, NANOBODIES®) and other antibody fragments that retain at least a portion of the variable region of an intact antibody. See, e.g., Hudson et al. (Nature Med., 9:129-134 (2003)).

The term "antigen binding fragment" or "antigen-binding portion" of an antibody, as used herein, refers to one or more fragments of an antibody that retain the ability to bind to an antigen. The antigen-binding function of an antibody can be performed by fragments of an intact antibody. Examples of binding fragments encompassed within the term "antigen-binding fragment" of an antibody include but are not limited to, Fab, Fab', F(ab')2, Fv, scFv, disulfide linked Fv, Fd, diabodies, single-chain antibodies, single domain antibodies (such as but not limited to, NANOBODIES®), isolated CDRH3, and other antibody fragments that retain at least a portion of the variable region of an intact antibody. These antibody fragments are obtained using conventional recombinant and/or enzymatic techniques and are screened for antigen binding in the same manner as intact antibodies.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. Kappa and lambda light chains refer to the two major antibody light chain isotypes.

The terms "CDR," and its plural "CDRs," refer to a complementarity determining region (CDR) of an antibody or antibody fragment, which determine the binding character of an antibody or antibody fragment. In most instances, three CDRs are present in a light chain variable region (CDRL1, CDRL2 and CDRL3) and three CDRs are present in a heavy chain variable region (CDRH1, CDRH2 and CDRH3). CDRs contribute to the functional activity of an antibody molecule and are separated by amino acid sequences that comprise scaffolding or framework regions. Among the various CDRs, the CDR3 sequences, and particularly CDRH3, are the most diverse and therefore have the strongest contribution to antibody specificity. There are at least two techniques for determining CDRs: (1) an approach based on cross-species sequence variability (i.e., Kabat et al., Sequences of Proteins of Immunological Interest (National Institute of Health, Bethesda, Md. (1987), incorporated by reference in its entirety); and (2) an approach based on crystallographic studies of antigen-antibody complexes (Chothia et al., Nature, 342:877 (1989), incorporated by reference in its entirety).

The term "epitope" includes any protein determinant capable of specific binding to an immunoglobulin or T-cell receptor. In certain embodiments, an epitope is a region of an antigen that is specifically bound by an antibody. Epitopic determinants usually include chemically active surface groupings of molecules such as amino acids, sugar side chains, phosphoryl, or sulfonyl groups. In certain embodiments, an epitope may have specific three-dimensional structural characteristics (e.g., a "conformational epitope"), as well as specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

An antibody "specifically binds" an antigen when it preferentially recognizes the antigen in a complex mixture of proteins and/or macromolecules. In certain embodiments, an antibody comprises an antigen-binding site that specifically binds to a particular epitope. In certain such embodiments, the antibody is capable of binding different antigens so long as the different antigens comprise that particular epitope or closely related epitopes. In certain instances, for example, homologous proteins from different species may comprise the same epitope. In certain embodiments, an antibody specifically binds to an antigen with a dissociation constant of no greater than $10^{-6}$ M, $10^{-7}$ M, $10^{-8}$ M or $10^{-9}$ M. When an antibody specifically binds to a receptor or ligand (i.e., counterreceptor), it may substantially inhibit adhesion of the receptor to the ligand. As used herein, an antibody substantially inhibits adhesion of a receptor to a ligand when an excess of antibody reduces the quantity of receptor bound to ligand by at least about 20%, 40%, 60% or 80%, 85%, or 90% (as measured in an in vitro competitive binding assay).

An "isolated" antibody is one which has been separated and/or recovered from a component of the environment in which it was produced. Contaminant components of its production environment are materials which would interfere with diagnostic or therapeutic uses for the antibody, and may include enzymes, hormones, and other proteinaceous or nonproteinaceous solutes. In certain embodiments, the antibody will be purified as measurable by at least three different methods: 1) to greater than 50% by weight of antibody as determined by the Lowry method, such as more than 75% by weight, or more than 85% by weight, or more than 95% by weight, or more than 99% by weight; 2) to a degree sufficient to obtain at least 10 residues of N-terminal or internal amino acid sequence by use of a spinning cup sequenator, such as at least 15 residues of sequence; or 3) to homogeneity by SDS-PAGE under reducing or non-reducing conditions using Coomassie blue or, alternatively, silver stain. Isolated antibody includes the antibody in situ within recombinant cells since at least one component of the environment in which the antibody is produced will not be present. Ordinarily, however, isolated antibody will be prepared by at least one purification step. In addition, the "isolated antibody" is substantially free of other antibodies having different antigenic specificities. An isolated antibody may, however, have some cross-reactivity to other, related antigens.

The term "antibody mutant" refers to an amino acid sequence variant of an antibody wherein one or more of the amino acid residues have been modified. Such mutants necessarily have less than 100% sequence identity or similarity with the amino acid sequence having at least 75% amino acid sequence identity or similarity with the amino acid sequence of either the heavy or light chain variable domain of the antibody, such as at least 80%, or at least 85%, or at least 90%, or at least 95%.

The term "monoclonal antibody" as used herein refers to an antibody obtained from a population of substantially homogeneous antibodies that specifically bind to the same epitope, i.e., the individual antibodies comprising the population are identical except for possible naturally occurring mutations that may be present in minor amounts. In contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that in one method of production they may be synthesized by a hybridoma culture, and thus are uncontaminated by other immunoglobulins. The modifier "monoclonal" indicates the character of the antibody as being obtained from a substantially homogeneous population of antibodies, and is not to be construed as requiring production of the antibody by any particular method. For example, in one embodiment, the monoclonal antibodies produced in accordance with the present disclosure may be made by the hybridoma method first described by Kohler and Milstein (Nature, 256:495 (1975)).

The monoclonal antibodies utilized in accordance with the present disclosure may be produced by any methodology known in the art including, but not limited to, a result of a deliberate immunization protocol; a result of an immune response that results in the production of antibodies naturally in the course of a disease or cancer; phage-derived antibodies; and the like. In addition to the hybridoma production method listed above, the monoclonal antibodies of the present disclosure may be produced by other various methods such as, but not limited to, recombinant DNA methods (see, e.g., U.S. Pat. No. 4,816,567); isolation of antibody fragments from a phage display library (see, e.g., Clackson et al., Nature, 352: 624-628 (1991); and Marks et al., J. Mol. Biol., 222:581-597 (1991)); as well as various other monoclonal antibody production techniques (see, e.g., Harlow and Lane (1988) Antibodies: A Laboratory Manual (Cold Spring Harbor Laboratory, Cold Spring Harbor, N.Y.)).

Once the antibodies have been obtained, for example, once individual B cells have been identified and/or monoclonal antibodies have been produced, the sequences encoding the variable regions of these antibodies can be obtained. The variable region sequences can, for example, be obtained by first sequencing the antibody protein produced by the hybridoma, B-cell or phage and determining the encoding nucleic acid sequence. In one embodiment, the immunoglobulin variable region (VH and VL) DNA or cDNA may be sequenced instead. Where the antibody is derived from a hybridoma cell line or isolated B-cell, the cDNAs encoding the variable regions may be amplified using PCR by, for example, the methods described in Babcook et al. (Proc. Natl. Acad. Sci. USA, 93:7843-7848 (1996)), and in PCT Publication No. WO 92/02551. The contents of both references are expressly incorporated herein by reference in their entirety.

The term "neutralizing antibody" or "antibody that neutralizes" refers to an antibody that reduces at least one activity of a polypeptide comprising the epitope to which the antibody specifically binds. In certain embodiments, a neutralizing antibody reduces an activity in vitro and/or in vivo.

The term "antigen-binding site" refers to a portion of an antibody capable of specifically binding an antigen. In certain embodiments, an antigen-binding site is provided by one or more antibody variable regions.

As used herein, "substantially pure" means an object species is the predominant species present (i.e., on a molar basis it is more abundant than any other individual species in the composition). Generally, a substantially pure composition will comprise more than about 50% percent of all macromolecular species present in the composition, such as more than about 55%, 60%, 65%, 70%, 75%, 80%, 85%, 90%, 95%, and 99%. In one embodiment, the object species is purified to essential homogeneity (contaminant species cannot be detected in the composition by conventional detection methods) wherein the composition consists essentially of a single macromolecular species.

The term "agent" refers to a chemical compound, a mixture of chemical compounds, a biological macromolecule, or an extract made from biological materials. In certain embodiments, the "agent" may be a monoclonal antibody in accordance with the present disclosure.

The term "antagonist" refers to an agent that reduces an activity of a protein/enzyme.

The term "agonist" refers to an agent that increases an activity of a protein/enzyme.

The term "carrier protein" as used herein will be understood to refer to an immunogenic protein that can be attached to small molecules (such as (but not limited to) drugs, organic compounds, and peptides and oligosaccharides with a molecular weight of less than 2-5 kDa) that are typically not immunogenic, for the purpose of stimulating an immune system response in the form of production of antibodies against the small molecule.

Turning now to the inventive concepts, certain non-limiting embodiments of the present disclosure are directed to an antibody or functional fragment thereof that specifically binds to naloxone and/or naltrexone. These two compounds are depicted below as Formulas I and II, respectively.

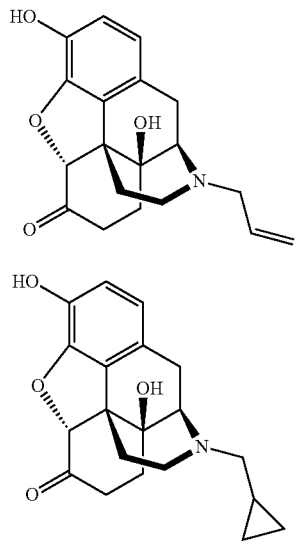

Formula I

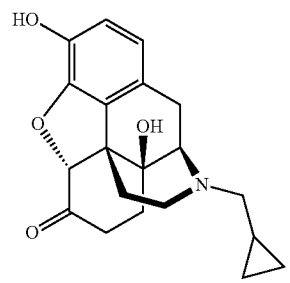

Formula II

In a particular non-limiting embodiment, the antibody or functional fragment thereof specifically binds to a conjugate comprising naloxone and/or naltrexone bound to a carrier protein. The conjugate may contain any carrier protein known in the art or otherwise contemplated herein, so long as the carrier protein: (1) can be conjugated to naloxone and/or naltrexone; (2) is immunogenic; and (3) can function to stimulate an immune system response in the form of production of antibodies against naloxone and/or naltrexone. Non-limiting examples of carrier proteins that may be utilized in accordance with the present disclosure include KLH (Keyhole Limpet Hemocyanin), BSA (Bovine Serum Albumin), Ovalbumin, BTG (Bovine Thyroglobulin), and BGG (Bovine Gamma Globulin).

In certain non-limiting embodiments, the carrier protein is attached to a specific carbon position on the naloxone and/or naltrexone. For example (but not by way of limitation), the carrier protein may be attached to the 1-carbon, 2-carbon, 3-carbon, 6-carbon, 7-carbon, or 8-carbon position of naloxone and/or naltrexone. Non-limiting examples of these conjugate immunogens are shown in Formulas III-VIII below. Note that each of these formulas covers both naloxone and naltrexone, and that the carrier protein is illustrated as being attached to a different carbon in each formula (Formula III: 3-carbon; Formula IV: 1-carbon; Formula V: 2-carbon; Formula VI: 6-carbon; Formula VII: 8-carbon; and Formula VIII: 7-carbon).

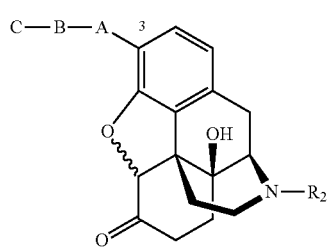

Formula III wherein, in Formula III: A is a hetero atom (such as, but not limited to: —O—, —N—, or —S—); B is a functional group (such as, but not limited to: —CO—, a lower alkyl ($C_0$ to $C_{10}$), —CONH—, —SO$_2$—, —PO$_4$—, and the like); C is a carrier protein (such as, but not limited to: KLH, BSA, OVA, BGG, G6PDH, or poly(amino acid)); and $R_2$ is H, alkyl, allyl, or methylenecyclopropyl.

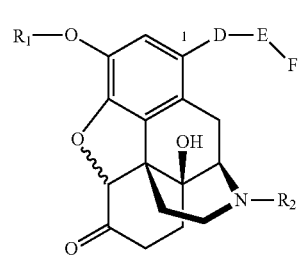

Formula IV wherein, in Formula IV: D is a hetero atom (such as, but not limited to: O—, S—, CO—, or CH$_2$—); E is a lower alkyl, CO$_2$—, CONH—, SO$_2$—, or PO$_4$—; F is a carrier protein (such as, but not limited to: KLH, BSA, OVA, BGG, G6PDH, or poly(amino acid)); $R_2$ is H, alkyl, allyl, or methylenecyclopropyl; and $R_1$ is H or CH$_3$.

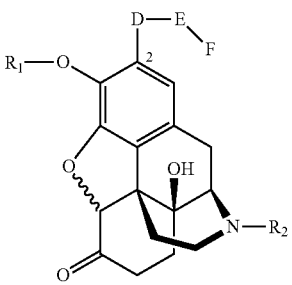

Formula V wherein, in Formula V: D is a hetero atom (such as, but not limited to: O—, S—, CO—, or CH$_2$—); E is a lower alkyl, CO$_2$—, CONH—, SO$_2$—, or PO$_4$—; F is a carrier protein (such as, but not limited to: KLH, BSA, OVA, BGG, G6PDH, or poly(amino acid)); $R_2$ is H, alkyl, allyl, or methylenecyclopropyl; and $R_1$ is H or CH$_3$.

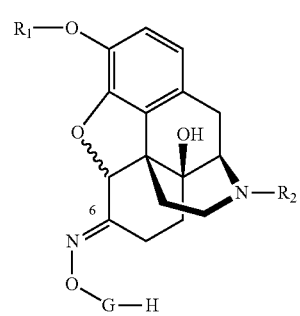

Formula VI wherein, in Formula VI: G is a linking group which includes at least two of the following: a lower alkyl chain, CO$_2$—, CONH—, SO$_2$—, and PO$_4$—; H is a carrier protein (such as, but not limited to: KLH, BSA, OVA, BGG, G6PDH, or poly(amino acid)); $R_1$ is H or CH$_3$; and $R_2$ is H, alkyl, allyl, or methylenecyclopropyl.

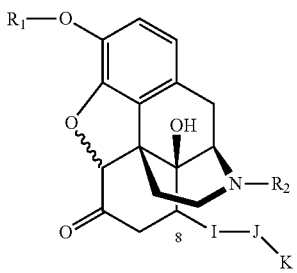

Formula VII wherein, in Formula VII: I is a hetero atom (such as, but not limited to: O—, S—, CO—, or CH$_2$—); J is a lower alkyl chain, CO$_2$—, CONH—, SO$_2$—, or PO$_4$—; K is a carrier protein (such as, but not limited to: KLH, BSA, OVA, BGG, G6PDH, or poly(amino acid)); R$_1$ is H or CH$_3$; and R$_2$ is H, alkyl, allyl, or methylenecyclopropyl.

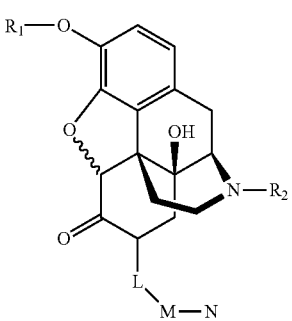

Formula VIII wherein, in Formula VII: L is a hetero atom (such as, but not limited to O, S, CO, or CH$_2$); M is a lower alkyl chain, CO$_2$—, CONH—, SO$_2$—, or PO$_4$—; N is a carrier protein (such as, but not limited to: KLH, BSA, OVA, BGG, G6PDH, and the like); R$_1$ is H or CH$_3$; and R$_2$ is H, alkyl, allyl, or methylenecyclopropyl.

In a particular (but non-limiting) embodiment, the antibody or functional fragment thereof specifically binds to a conjugate comprising OVA attached to the 3-carbon position and/or 6-carbon position of naloxone and/or naltrexone.

Certain non-limiting embodiments of the present disclosure are directed to an antibody or functional fragment thereof that specifically binds to naltrexone (and in certain particular (but non-limiting) embodiments, the conjugate of Formula III, wherein R$_2$ is an allyl), wherein the antibody comprises one or more of: (i) a heavy chain variable region CDR1 having the amino acid sequence of SEQ ID NO:2; (ii) a heavy chain variable region CDR2 having the amino acid sequence of SEQ ID NO:3; (iii) a heavy chain variable region CDR3 having the amino acid sequence of SEQ ID NO:4; (iv) a light chain variable region CDR1 having the amino acid sequence of SEQ ID NO:6; (v) a light chain variable region CDR2 having the amino acid sequence of SEQ ID NO:7; and (vi) a light chain variable region CDR3 having the amino acid sequence of SEQ ID NO:8. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naltrexone, wherein the antibody comprises one or more of: (i) a heavy chain variable region CDR1 having the amino acid sequence of SEQ ID NO:22; (ii) a heavy chain variable region CDR2 having the amino acid sequence of SEQ ID NO:23; (iii) a heavy chain variable region CDR3 having the amino acid sequence of SEQ ID NO:24; (iv) a light chain variable region CDR1 having the amino acid sequence of SEQ ID NO:26; (v) a light chain variable region CDR2 having the amino acid sequence of SEQ ID NO:27; and (vi) a light chain variable region CDR3 having the amino acid sequence of SEQ ID NO:28. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naltrexone, wherein the antibody comprises one or more of: (i) a heavy chain variable region CDR1 having the amino acid sequence of SEQ ID NO:42; (ii) a heavy chain variable region CDR2 having the amino acid sequence of SEQ ID NO:43; (iii) a heavy chain variable region CDR3 having the amino acid sequence of SEQ ID NO:44; (iv) a light chain variable region CDR1 having the amino acid sequence of SEQ ID NO:46; (v) a light chain variable region CDR2 having the amino acid sequence of SEQ ID NO:47; and (vi) a light chain variable region CDR3 having the amino acid sequence of SEQ ID NO:48. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naltrexone, wherein the antibody comprises one or more of: (i) a heavy chain variable region CDR1 having the amino acid sequence of SEQ ID NO:62; (ii) a heavy chain variable region CDR2 having the amino acid sequence of SEQ ID NO:63; (iii) a heavy chain variable region CDR3 having the amino acid sequence of SEQ ID NO:64; (iv) a light chain variable region CDR1 having the amino acid sequence of SEQ ID NO:66; (v) a light chain variable region CDR2 having the amino acid sequence of SEQ ID NO:67; and (vi) a light chain variable region CDR3 having the amino acid sequence of SEQ ID NO:68. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naltrexone, wherein the antibody comprises one or more of: (i) a heavy chain variable region CDR1 having the amino acid sequence of SEQ ID NO:82; (ii) a heavy chain variable region CDR2 having the amino acid sequence of SEQ ID NO:83; (iii) a heavy chain variable region CDR3 having the amino acid sequence of SEQ ID NO:84; (iv) a light chain variable region CDR1 having the amino acid sequence of SEQ ID NO:86; (v) a light chain variable region CDR2 having the amino acid sequence of SEQ ID NO:87; and (vi) a light chain variable region CDR3 having the amino acid sequence of SEQ ID NO:88. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naltrexone, wherein the antibody comprises one or more of: (i) a heavy chain variable region CDR1 having the amino acid sequence of SEQ ID NO:102; (ii) a heavy chain variable region CDR2 having the amino acid sequence of SEQ ID NO:103; (iii) a heavy chain variable region CDR3 having the amino acid sequence of SEQ ID NO:104; (iv) a light chain variable region CDR1 having the amino acid sequence of SEQ ID NO:106; (v) a light chain variable region CDR2 having the amino acid sequence of SEQ ID NO:107; and (vi) a light chain variable region CDR3 having the amino acid sequence of SEQ ID NO:108. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naltrexone, wherein the antibody comprises one or more of: (i) a heavy chain variable region CDR1 having the amino acid sequence of SEQ ID NO:122; (ii) a heavy chain variable region CDR2 having the amino acid sequence of SEQ ID NO:123; (iii) a heavy chain variable region CDR3 having the amino acid sequence of SEQ ID NO:124; (iv) a light chain variable region CDR1 having the amino acid sequence of SEQ ID NO:126; (v) a light chain variable region CDR2 having the amino acid sequence of SEQ ID NO:127; and (vi) a light chain variable region CDR3 having the amino acid sequence of SEQ ID NO:128. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naltrexone, wherein the antibody comprises one or more of: (i) a heavy chain variable region CDR1 having the amino acid sequence of SEQ ID NO:142; (ii) a heavy chain variable region CDR2 having the amino acid sequence of SEQ ID NO:143; (iii) a heavy chain variable region CDR3 having the amino acid sequence of SEQ ID NO:144; (iv) a light chain variable region CDR1 having the amino acid sequence of SEQ ID NO:146; (v) a light chain variable region CDR2 having the amino acid sequence of SEQ ID NO:147; and (vi) a light chain variable region CDR3 having the amino acid sequence of SEQ ID NO:148. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naloxone, wherein the antibody comprises one or more of: (i) a heavy chain variable region CDR1 having the amino acid sequence of SEQ ID NO:162; (ii) a heavy chain variable region CDR2 having the amino acid sequence of SEQ ID NO:163; (iii) a heavy chain variable region CDR3 having the amino acid sequence of SEQ ID NO:164; (iv) a light chain variable region CDR1 having the amino acid sequence of SEQ ID NO:166; (v) a light chain variable region CDR2 having the amino acid sequence of SEQ ID NO:167; and (vi) a light chain variable region CDR3 having the amino acid sequence of SEQ ID NO:168. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naloxone, wherein the antibody comprises one or more of: (i) a heavy chain variable region CDR1 having the amino acid sequence of SEQ ID NO:182; (ii) a heavy chain variable region CDR2 having the amino acid sequence of SEQ ID NO:183; (iii) a heavy chain variable region CDR3 having the amino acid sequence of SEQ ID NO:184; (iv) a light chain variable region CDR1 having the amino acid sequence of SEQ ID NO:186; (v) a light chain variable region CDR2 having the amino acid sequence of SEQ ID NO:187; and (vi) a light chain variable region CDR3 having the amino acid sequence of SEQ ID NO:188. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naloxone, wherein the antibody comprises one or more of: (i) a heavy chain variable region CDR1 having the amino acid sequence of SEQ ID NO:202; (ii) a heavy chain variable region CDR2 having the amino acid sequence of SEQ ID NO:203; (iii) a heavy chain variable region CDR3 having the amino acid sequence of SEQ ID NO:204; (iv) a light chain variable region CDR1 having the amino acid sequence of SEQ ID NO:206; (v) a light chain variable region CDR2 having the amino acid sequence of SEQ ID NO:207; and (vi) a light chain variable region CDR3 having the amino acid sequence of SEQ ID NO:208. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naloxone, wherein the antibody comprises one or more of: (i) a heavy chain variable region CDR1 having the amino acid sequence of SEQ ID NO:222; (ii) a heavy chain variable region CDR2 having the amino acid sequence of SEQ ID NO:223; (iii) a heavy chain variable region CDR3 having the amino acid sequence of SEQ ID NO:224; (iv) a light chain variable region CDR1 having the amino acid sequence of SEQ ID NO:226; (v) a light chain variable region CDR2 having the amino acid sequence of SEQ ID NO:227; and (vi) a light chain variable region CDR3 having the amino acid sequence of SEQ ID NO:228. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naloxone, wherein the antibody comprises one or more of: (i) a heavy chain variable region CDR1 having the amino acid sequence of SEQ ID NO:242; (ii) a heavy chain variable region CDR2 having the amino acid sequence of SEQ ID NO:243; (iii) a heavy chain variable region CDR3 having the amino acid sequence of SEQ ID NO:244; (iv) a light chain variable region CDR1 having the amino acid sequence of SEQ ID NO:246; (v) a light chain variable region CDR2 having the amino acid sequence of SEQ ID NO:247; and (vi) a light chain variable region CDR3 having the amino acid sequence of SEQ ID NO:248. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

In a particular (but non-limiting) embodiment, the antibody or functional fragment thereof has a heavy chain variable region with an amino acid sequence that is at least about 70% identical to any of the heavy chain variable region amino acid sequences outlined in Tables 2-14 (i.e., SEQ ID NO:17, 37, 57, 77, 97, 117, 137, 157, 177, 197, 217, 237, or 257), such as (but not limited to) at least about 75% identical, at least about 80% identical, at least about 85% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:17, 37, 57, 77, 97, 117, 137, 157, 177, 197, 217, 237, or 257.

In a particular (but non-limiting) embodiment, the antibody or functional fragment thereof has a heavy chain variable region with an amino acid sequence that differs from SEQ ID NO:17, 37, 57, 77, 97, 117, 137, 157, 177, 197, 217, 237, or 257 by less than about 25 amino acids, less than about 24 amino acids, less than about 23 amino acids, less than about 22 amino acids, less than about 21 amino acids, less than about 20 amino acids, less than about 19 amino acids, less than about 18 amino acids, less than about 17 amino acids, less than about 16 amino acids, less than about 15 amino acids, less than about 14 amino acids, less than about 13 amino acids, less than about 12 amino acids, less than about 11 amino acids, less than about 10 amino acids, less than about 9 amino acids, less than about 8 amino acids, less than about 7 amino acids, less than about 6 amino acids, less than about 5 amino acids, less than about 4 amino acids, less than about 3 amino acids, less than about 2 amino acids, or less than about 1 amino acids.

In a particular (but non-limiting) embodiment, and alternatively and/or in addition to the above embodiments, the antibody or functional fragment thereof has a light chain variable region with an amino acid sequence that is at least about 70% identical to any of the light chain variable region amino acid sequences outlined in Tables 2-14 (i.e., SEQ ID NO:18, 38, 58, 78, 98, 118, 138, 158, 178, 198, 218, 238, or 258), such as (but not limited to) at least about 75% identical, at least about 80% identical, at least about 85% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:18, 38, 58, 78, 98, 118, 138, 158, 178, 198, 218, 238, or 258.

In a particular (but non-limiting) embodiment, the antibody or functional fragment thereof has a light chain variable region with an amino acid sequence that differs from SEQ ID NO:18, 38, 58, 78, 98, 118, 138, 158, 178, 198, 218, 238, or 258 by less than about 21 amino acids, less than about 20 amino acids, less than about 19 amino acids, less than about 18 amino acids, less than about 17 amino acids, less than about 16 amino acids, less than about 15 amino acids, less than about 14 amino acids, less than about 13 amino acids, less than about 12 amino acids, less than about 11 amino acids, less than about 10 amino acids, less than about 9 amino acids, less than about 8 amino acids, less than about 7 amino acids, less than about 6 amino acids, less than about 5 amino acids, less than about 4 amino acids, less than about 3 amino acids, less than about 2 amino acids, or less than about 1 amino acids.

In a particular (but non-limiting) embodiment, the antibody or functional fragment thereof has a heavy chain variable region with an amino acid sequence that is at least about 90% identical to SEQ ID NO:17, 37, 57, 77, 97, 117, 137, 157, 177, 197, 217, 237, or 257, and/or the antibody or functional fragment thereof has a light chain variable region with an amino acid sequence that is at least about 90% identical to SEQ ID NO:18, 38, 58, 78, 98, 118, 138, 158, 178, 198, 218, 238, or 258. In a particular (but non-limiting) embodiment, the antibody or functional fragment thereof has a heavy chain variable region with an amino acid sequence that differs from SEQ ID NO:17, 37, 57, 77, 97, 117, 137, 157, 177, 197, 217, 237, or 257 by less than about 12 amino acids, and/or a light chain variable region with an amino acid sequence that differs from SEQ ID NO:18, 38, 58, 78, 98, 118, 138, 158, 178, 198, 218, 238, or 258 by less than about 12 amino acids.

In another particular (but non-limiting) embodiment, the antibody or functional fragment thereof has a heavy chain variable region with the amino acid sequence of SEQ ID NO:17, 37, 57, 77, 97, 117, 137, 157, 177, 197, 217, 237, or 257 and/or a light chain variable region with the amino acid sequence of SEQ ID NO:18, 38, 58, 78, 98, 118, 138, 158, 178, 198, 218, 238, or 258.

In another particular (but non-limiting) embodiment, the antibody or functional fragment thereof has a heavy chain with an amino acid sequence that is at least about 70% identical to any of the heavy chain amino acid sequences outlined in Tables 2-14 (i.e., SEQ ID NO:1, 21, 41, 61, 81, 101, 121, 141, 161, 181, 201, 221, or 241), such as (but not limited to) at least about 75% identical, at least about 80% identical, at least about 85% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:1, 21, 41, 61, 81, 101, 121, 141, 161, 181, 201, 221, or 241.

In a particular (but non-limiting) embodiment, the antibody or functional fragment thereof has a heavy chain with an amino acid sequence that differs from SEQ ID NO:1, 21, 41, 61, 81, 101, 121, 141, 161, 181, 201, 221, or 241 by less than about 100 amino acids, less than about 90 amino acids, less than about 80 amino acids, less than about 75 amino acids, less than about 70 amino acids, less than about 65 amino acids, less than about 60 amino acids, less than about 55 amino acids, less than about 50 amino acids, less than about 45 amino acids, less than about 40 amino acids, less than about 35 amino acids, less than about 30 amino acids, less than about 25 amino acids, less than about 24 amino acids, less than about 23 amino acids, less than about 22 amino acids, less than about 21 amino acids, less than about 20 amino acids, less than about 19 amino acids, less than about 18 amino acids, less than about 17 amino acids, less than about 16 amino acids, less than about 15 amino acids, less than about 14 amino acids, less than about 13 amino acids, less than about 12 amino acids, less than about 11 amino acids, less than about 10 amino acids, less than about 9 amino acids, less than about 8 amino acids, less than about 7 amino acids, less than about 6 amino acids, less than about 5 amino acids, less than about 4 amino acids, less than about 3 amino acids, less than about 2 amino acids, or less than about 1 amino acids.

In a particular (but non-limiting) embodiment, and alternatively and/or in addition to the above embodiments, the antibody or functional fragment thereof has a light chain with an amino acid sequence that is at least about 70% identical to any of the light chain amino acid sequences outlined in Tables 2-14 (i.e., SEQ ID NO:5, 25, 45, 65, 85, 105, 125, 145, 165, 185, 205, 225, or 245), such as (but not limited to) at least about 75% identical, at least about 80% identical, at least about 85% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:5, 25, 45, 65, 85, 105, 125, 145, 165, 185, 205, 225, or 245.

In a particular (but non-limiting) embodiment, the antibody or functional fragment thereof has a light chain with an amino acid sequence that differs from SEQ ID NO:5, 25, 45, 65, 85, 105, 125, 145, 165, 185, 205, 225, or 245 by less than about 45 amino acids, less than about 40 amino acids, less than about 35 amino acids, less than about 30 amino acids, less than about 25 amino acids, less than about 24 amino acids, less than about 23 amino acids, less than about 22 amino acids, less than about 21 amino acids, less than about 20 amino acids, less than about 19 amino acids, less than about 18 amino acids, less than about 17 amino acids, less than about 16 amino acids, less than about 15 amino acids, less than about 14 amino acids, less than about 13 amino acids, less than about 12 amino acids, less than about 11 amino acids, less than about 10 amino acids, less than about 9 amino acids, less than about 8 amino acids, less than about 7 amino acids, less than about 6 amino acids, less than about 5 amino acids, less than about 4 amino acids, less than about 3 amino acids, less than about 2 amino acids, or less than about 1 amino acids.

In a particular (but non-limiting) embodiment, the antibody or functional fragment thereof has a heavy chain with an amino acid sequence that is at least about 90% identical to SEQ ID NO:1, 21, 41, 61, 81, 101, 121, 141, 161, 181, 201, 221, or 241, and/or the antibody or functional fragment thereof has a light chain with an amino acid sequence that is at least about 70% identical to SEQ ID NO:5, 25, 45, 65, 85, 105, 125, 145, 165, 185, 205, 225, or 245. In a particular (but non-limiting) embodiment, the antibody or functional fragment thereof has a heavy chain with an amino acid sequence that differs from SEQ ID NO:1, 21, 41, 61, 81, 101, 121, 141, 161, 181, 201, 221, or 241 by less than about 46 amino acids, and/or a light chain with an amino acids sequence that differs from SEQ ID NO:5, 25, 45, 65, 85, 105, 125, 145, 165, 185, 205, 225, or 245 by less than about 24 amino acids.

In another particular (but non-limiting) embodiment, the antibody or functional fragment thereof has a heavy chain with the amino acid sequence of SEQ ID NO:1, 21, 41, 61, 81, 101, 121, 141, 161, 181, 201, 221, or 241 and/or a light chain with the amino acid sequence of SEQ ID NO:5, 25, 45, 65, 85, 105, 125, 145, 165, 185, 205, 225, or 245.

In yet another particular (but non-limiting) embodiment, the antibody or functional fragment has a heavy chain encoded by a polynucleotide that is at least about 70% identical to SEQ ID NO:9, 29, 49, 69, 89, 109, 129, 149, 169, 189, 209, 229, or 249 (and/or a heavy chain variable region encoded by a polynucleotide that is at least about 70% identical to SEQ ID NO:19, 39, 59, 79, 99, 119, 139, 159, 179, 199, 219, 239, or 259), such as (but not limited to) at least about 75% identical, at least about 80% identical, at least about 85% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:9, 29, 49, 69, 89, 109, 129, 149, 169, 189, 209, 229, or 249 and/or SEQ ID NO:19, 39, 59, 79, 99, 119, 139, 159, 179, 199, 219, 239, or 259.

In yet another particular (but non-limiting) embodiment, and alternatively and/or in addition to the above embodiment, the antibody or functional fragment has a light chain encoded by a polynucleotide that is at least about 70% identical to SEQ ID NO:13, 33, 53, 73, 93, 113, 133, 153, 173, 193, 213, 233, or 253 (and/or a light chain variable region encoded by a polynucleotide that is at least about 70% identical to SEQ ID NO:20, 40, 60, 80, 100, 120, 140, 160, 180, 200, 220, 240, or 260), such as (but not limited to) at least about 75% identical, at least about 80% identical, at least about 85% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:13, 33, 53, 73, 93, 113, 133, 153, 173, 193, 213, 233, or 253 and/or SEQ ID NO:20, 40, 60, 80, 100, 120, 140, 160, 180, 200, 220, 240, or 260.

In yet a further particular (but non-limiting) embodiment, the antibody or functional fragment has a heavy chain encoded by a polynucleotide that is at least about 70% identical to SEQ ID NO:9, 29, 49, 69, 89, 109, 129, 149, 169, 189, 209, 229, or 249, and/or the antibody or functional fragment has a light chain encoded by a polynucleotide that is at least about 70% identical to SEQ ID NO:13, 33, 53, 73, 93, 113, 133, 153, 173, 193, 213, 233, or 253.

In yet a further particular (but non-limiting) embodiment, the antibody or functional fragment has a heavy chain variable region encoded by a polynucleotide that is at least about 70% identical to SEQ ID NO:19, 39, 59, 79, 99, 119, 139, 159, 179, 199, 219, 239, or 259, and/or the antibody or functional fragment has a light chain variable region encoded by a polynucleotide that is at least about 70% identical to SEQ ID NO:20, 40, 60, 80, 100, 120, 140, 160, 180, 200, 220, 240, or 260.

In yet another particular (but non-limiting) embodiment, the antibody or functional fragment thereof has a heavy chain encoded by a sequence that differs from SEQ ID NO:9, 29, 49, 69, 89, 109, 129, 149, 169, 189, 209, 229, or 249 (and/or a heavy chain variable region encoded by a sequence that differs from SEQ ID NO:19, 39, 59, 79, 99, 119, 139, 159, 179, 199, 219, 239, or 259) by less than about 100 nucleotides, less than about 90 nucleotides, less than about 80 nucleotides, less than about 75 nucleotides, less than about 70 nucleotides, less than about 60 nucleotides, less than about 50 nucleotides, less than about 45 nucleotides, less than about 40 nucleotides, less than about 35 nucleotides, less than about 30 nucleotides, less than about 25 nucleotides, less than about 20 nucleotides, less than about 15 nucleotides, less than about 10 nucleotides, less than about 9 nucleotides, less than about 8 nucleotides, less than about 7 nucleotides, less than about 6 nucleotides, less than about 5 nucleotides, less than about 4 nucleotides, less than about 3 nucleotides, less than about 2 nucleotides, or less than about 1 nucleotide.

In yet another particular (but non-limiting) embodiment, and alternatively and/or in addition to the above embodiment, the antibody or functional fragment thereof has a light chain encoded by a sequence that differs from SEQ ID NO:9, 29, 49, 69, 89, 109, 129, 149, 169, 189, 209, 229, or 249 (and/or a light chain variable region encoded by a sequence that differs from SEQ ID NO:20, 40, 60, 80, 100, 120, 140, 160, 180, 200, 220, 240, or 260) by less than about 100 nucleotides, less than about 90 nucleotides, less than about 80 nucleotides, less than about 75 nucleotides, less than about 70 nucleotides, less than about 60 nucleotides, less than about 50 nucleotides, less than about 45 nucleotides, less than about 40 nucleotides, less than about 35 nucleotides, less than about 30 nucleotides, less than about 25 nucleotides, less than about 20 nucleotides, less than about 15 nucleotides, less than about 10 nucleotides, less than about 9 nucleotides, less than about 8 nucleotides, less than about 7 nucleotides, less than about 6 nucleotides, less than about 5 nucleotides, less than about 4 nucleotides, less than about 3 nucleotides, less than about 2 nucleotides, or less than about 1 nucleotide.

In yet another particular (but non-limiting) embodiment, the antibody or functional fragment thereof has a heavy chain encoded by a sequence that differs from SEQ ID NO:9, 29, 49, 69, 89, 109, 129, 149, 169, 189, 209, 229, or 249 by less than about 100 nucleotides and/or a light chain encoded by a sequence that differs from SEQ ID NO:13, 33, 53, 73, 93, 113, 133, 153, 173, 193, 213, 233, or 253 by less than about 70 nucleotides.

In yet another particular (but non-limiting) embodiment, the antibody or functional fragment thereof has a heavy chain variable region encoded by a sequence that differs from SEQ ID NO:19, 39, 59, 79, 99, 119, 139, 159, 179, 199, 219, 239, or 259 by less than about 35 nucleotides and/or a light chain variable region encoded by a sequence that differs from SEQ ID NO:20, 40, 60, 80, 100, 120, 140, 160, 180, 200, 220, 240, or 260 by less than about 34 nucleotides.

Certain non-limiting embodiments of the present disclosure are directed to an antibody or functional fragment thereof that specifically binds to naltrexone (and in certain particular (but non-limiting) embodiments, the conjugate of Formula III, wherein $R_2$ is a cyclopropyl), wherein the antibody comprises one or more of: (i) a heavy chain variable region CDR1 encoded by a sequence of SEQ ID NO:10; (ii) a heavy chain variable region CDR2 encoded by a sequence of SEQ ID NO:11; (iii) a heavy chain variable region CDR3 encoded by a sequence of SEQ ID NO:12; (iv) a light chain variable region CDR1 encoded by a sequence of SEQ ID NO:14; (v) a light chain variable region CDR2 encoded by a sequence of SEQ ID NO:15; and (vi) a light chain variable region CDR3 encoded by a sequence of SEQ ID NO:16. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naltrexone (and in certain particular (but non-limiting) embodiments, the conjugate of Formula III, wherein $R_2$ is a cyclopropyl), wherein the antibody comprises one or more of: (i) a heavy chain variable region CDR1 encoded by a sequence of SEQ ID NO:30; (ii) a heavy chain variable region CDR2 encoded by a sequence of SEQ ID NO:31; (iii) a heavy chain variable region CDR3 encoded by a sequence of SEQ ID NO:32; (iv) a light chain variable region CDR1 encoded by a sequence of SEQ ID NO:34; (v) a light chain variable region CDR2 encoded by a sequence of SEQ ID NO:35; and (vi) a light chain variable region CDR3 encoded by a sequence of SEQ ID NO:36. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naltrexone (and in certain particular (but non-limiting) embodiments, the conjugate of Formula III, wherein $R_2$ is a cyclopropyl), wherein the antibody comprises one or more of: (i) a heavy chain variable region CDR1 encoded by a sequence of SEQ ID NO:50; (ii) a heavy chain variable region CDR2 encoded by a sequence of SEQ ID NO:51; (iii) a heavy chain variable region CDR3 encoded by a sequence of SEQ ID NO:52; (iv) a light chain variable region CDR1 encoded by a sequence of SEQ ID NO:54; (v) a light chain variable region CDR2 encoded by a sequence of SEQ ID NO:55; and (vi) a light chain variable region CDR3 encoded by a sequence of SEQ ID NO:56. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naltrexone (and in certain particular (but non-limiting) embodiments, the conjugate of Formula III, wherein $R_2$ is a cyclopropyl), wherein the antibody comprises one or more of: (i) a heavy chain variable region CDR1 encoded by a sequence of SEQ ID NO:70; (ii) a heavy chain variable region CDR2 encoded by a sequence of SEQ ID NO:71; (iii) a heavy chain variable region CDR3 encoded by a sequence of SEQ ID NO:72; (iv) a light chain variable region CDR1 encoded by a sequence of SEQ ID NO:74; (v) a light chain variable region CDR2 encoded by a sequence of SEQ ID NO:75; and (vi) a light chain variable region CDR3 encoded by a sequence of SEQ ID NO:76. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naltrexone (and in certain particular (but non-limiting) embodiments, the conjugate of Formula III, wherein $R_2$ is a cyclopropyl), wherein the antibody comprises one or more of: (i) a heavy chain variable region CDR1 encoded by a sequence of SEQ ID NO:90; (ii) a heavy chain variable region CDR2 encoded by a sequence of SEQ ID NO:91; (iii) a heavy chain variable region CDR3 encoded by a sequence of SEQ ID NO:92; (iv) a light chain variable region CDR1 encoded by a sequence of SEQ ID NO:94; (v) a light chain variable region CDR2 encoded by a sequence of SEQ ID NO:95; and (vi) a light chain variable region CDR3 encoded by a sequence of SEQ ID NO:96. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naltrexone (and in certain particular (but non-limiting) embodiments, the conjugate of Formula III, wherein $R_2$ is a cyclopropyl), wherein the antibody comprises one or more of: (i) a heavy chain variable region CDR1 encoded by a sequence of SEQ ID NO:110; (ii) a heavy chain variable region CDR2 encoded by a sequence of SEQ ID NO:111; (iii) a heavy chain variable region CDR3 encoded by a sequence of SEQ ID NO:112; (iv) a light chain variable region CDR1 encoded by a sequence of SEQ ID NO:114; (v) a light chain variable region CDR2 encoded by a sequence of SEQ ID NO:115; and (vi) a light chain variable region CDR3 encoded by a sequence of SEQ ID NO:116. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naltrexone (and in certain particular (but non-limiting) embodiments, the conjugate of Formula III, wherein $R_2$ is a cyclopropyl), wherein the antibody comprises one or more of: (i) a heavy chain variable region CDR1 encoded by a sequence of SEQ ID NO:130; (ii) a heavy chain variable region CDR2 encoded by a sequence of SEQ ID NO:131; (iii) a heavy chain variable region CDR3 encoded by a sequence of SEQ ID NO:132; (iv) a light chain variable region CDR1 encoded by a sequence of SEQ ID NO:134; (v) a light chain variable region CDR2 encoded by a sequence of SEQ ID NO:135; and (vi) a light chain variable region CDR3 encoded by a sequence of SEQ ID NO:136. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naltrexone (and in certain particular (but non-limiting) embodiments, the conjugate of Formula III, wherein $R_2$ is a cyclopropyl), wherein the antibody comprises one or more of: (i) a heavy chain variable region CDR1 encoded by a sequence of SEQ ID NO:150; (ii) a heavy chain variable region CDR2 encoded by a sequence of SEQ ID NO:151; (iii) a heavy chain variable region CDR3 encoded by a sequence of SEQ ID NO:152; (iv) a light chain variable region CDR1 encoded by a sequence of SEQ ID NO:154; (v) a light chain variable region CDR2 encoded by a sequence of SEQ ID NO:155; and (vi) a light chain variable region CDR3 encoded by a sequence of SEQ ID NO:156. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naloxone (and in certain particular (but non-limiting) embodiments, the conjugate of Formula III, wherein $R_2$ is a cyclopropyl), wherein the antibody comprises one or more of: (i) a heavy chain variable region CDR1 encoded by a sequence of SEQ ID NO:170; (ii) a heavy chain variable region CDR2 encoded by a sequence of SEQ ID NO:171; (iii) a heavy chain variable region CDR3 encoded by a sequence of SEQ ID NO:172; (iv) a light chain variable region CDR1 encoded by a sequence of SEQ ID NO:174; (v) a light chain variable region CDR2 encoded by a sequence of SEQ ID NO:175; and (vi) a light chain variable region CDR3 encoded by a sequence of SEQ ID NO:176. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naloxone (and in certain particular (but non-limiting) embodiments, the conjugate of Formula III, wherein $R_2$ is a cyclopropyl), wherein the antibody comprises one or more of: (i) a heavy chain variable region CDR1 encoded by a sequence of SEQ ID NO:190; (ii) a heavy chain variable region CDR2 encoded by a sequence of SEQ ID NO:191; (iii) a heavy chain variable region CDR3 encoded by a sequence of SEQ ID NO:192; (iv) a light chain variable region CDR1 encoded by a sequence of SEQ ID NO:194; (v) a light chain variable region CDR2 encoded by a sequence of SEQ ID NO:195; and (vi) a light chain variable region CDR3 encoded by a sequence of SEQ ID NO:196. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naloxone (and in certain particular (but non-limiting) embodiments, the conjugate of Formula III, wherein $R_2$ is a cyclopropyl), wherein the antibody comprises one or more of: (i) a heavy chain variable region CDR1 encoded by a sequence of SEQ ID NO:210; (ii) a heavy chain variable region CDR2 encoded by a sequence of SEQ ID NO:211; (iii) a heavy chain variable region CDR3 encoded by a sequence of SEQ ID NO:212; (iv) a light chain variable region CDR1 encoded by a sequence of SEQ ID NO:214; (v) a light chain variable region CDR2 encoded by a sequence of SEQ ID NO:215; and (vi) a light chain variable region CDR3 encoded by a sequence of SEQ ID NO:216. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naloxone (and in certain particular (but non-limiting) embodiments, the conjugate of Formula III, wherein $R_2$ is a cyclopropyl), wherein the antibody comprises one or more of: (i) a heavy chain variable region CDR1 encoded by a sequence of SEQ ID NO:230; (ii) a heavy chain variable region CDR2 encoded by a sequence of SEQ ID NO:231; (iii) a heavy chain variable region CDR3 encoded by a sequence of SEQ ID NO:232; (iv) a light chain variable region CDR1 encoded by a sequence of SEQ ID NO:234; (v) a light chain variable region CDR2 encoded by a sequence of SEQ ID NO:235; and (vi) a light chain variable region CDR3 encoded by a sequence of SEQ ID NO:236. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

Certain non-limiting embodiments of the present disclosure are directed to an antibody or functional fragment thereof that specifically binds to naloxone (and in certain particular (but non-limiting) embodiments, the conjugate of Formula III, wherein $R_2$ is a cyclopropyl), wherein the antibody comprises one or more of: (i) a heavy chain variable region CDR1 encoded by a sequence of SEQ ID NO:250; (ii) a heavy chain variable region CDR2 encoded by a sequence of SEQ ID NO:251; (iii) a heavy chain variable region CDR3 encoded by a sequence of SEQ ID NO:252; (iv) a light chain variable region CDR1 encoded by a sequence of SEQ ID NO:254; (v) a light chain variable region CDR2 encoded by a sequence of SEQ ID NO:255; and (vi) a light chain variable region CDR3 encoded by a sequence of SEQ ID NO:256. In a particular non-limiting embodiment, the antibody or functional fragment thereof comprises two, three, four, or five of (i)-(vi) above. In another particular non-limiting embodiment, the antibody or functional fragment thereof comprises all of (i)-(vi) above.

The antibody or functional fragment thereof may be a monoclonal antibody or functional fragment thereof. Alternatively, the antibody or functional fragment thereof may be a polyclonal antibody or functional fragment thereof.

In certain non-limiting embodiments, the antibody or functional fragment thereof is further defined as being selected from a full length immunoglobulin molecule, an scFv, a Fab fragment, a Fab' fragment, a F(ab')2, a Fv, a disulfide linked Fv, and combinations thereof.

In certain non-limiting embodiments, the antibody or functional fragment thereof is isolated. In particular (but non-limiting) embodiments, the antibody or functional fragment thereof is purified.

The present disclosure is also directed to antibodies or functional fragments thereof that bind to the same epitope as any of the antibodies or functional fragments described herein above.

Certain non-limiting embodiments of the present disclosure are also directed to a method of producing an antibody or functional fragment thereof which can specifically bind to naloxone and/or naltrexone. The method includes immunizing a non-human animal with an antigenic compound comprising a conjugate of a carrier protein attached to naloxone and/or naltrexone; and recovering the antibody or functional fragment thereof from blood plasma of the non-human animal.

Certain non-limiting embodiments of the present disclosure are also directed to a method of producing an antibody or functional fragment thereof which can specifically bind to naloxone and/or naltrexone. The method includes immunizing a non-human animal with an antigenic compound comprising a conjugate of a carrier protein attached to naloxone and/or naltrexone, thereby inducing B-cells producing antibodies that bind to the conjugate; and obtaining an antibody or functional fragment thereof produced by the B-cells. The antibody or functional fragment thereof can be obtained by various means known in the art, such as (but not limited to) via hybridoma technology or by B-cell PCR technology. The method may further include the optional step of further selecting for the antibody or functional fragment thereof based on binding to naloxone and/or naltrexone.

Certain non-limiting embodiments of the present disclosure are directed to a hybridoma producing any of the antibodies or functional fragments thereof described herein above.

Certain non-limiting embodiments of the present disclosure are directed to a method of producing an antibody or functional fragment thereof which can specifically bind to naloxone and/or naltrexone. In the method, a hybridoma capable of producing any of the antibodies or functional fragments thereof described or otherwise contemplated herein is cultured to produce any of the antibodies or functional fragments thereof described herein above. In at least certain non-limiting embodiments, the antibody or functional fragment thereof is recovered.

Certain non-limiting embodiments of the present disclosure are also directed to a conjugate comprising any of the antibodies or functional fragments thereof disclosed or otherwise contemplated herein attached to a detectable label. Non-limiting examples of detectable labels that may be utilized in accordance with the present disclosure include an enzyme label, a radioactive label, a fluorescent label, a chemiluminescent label, a bioluminescent label, and a particulate label, as well as any combinations thereof. In addition, the detectable label may be attached to the antibody or functional fragment via direct or indirect conjugation.

Certain non-limiting embodiments of the present disclosure are also directed to a conjugate comprising any of the antibodies or functional fragments thereof disclosed or otherwise contemplated herein attached to a solid support. Attachment of the antibody/function fragment to a solid support (via direct or indirect conjugation) produces an affinity purification chromatography substrate such as, for example, a column.

Certain non-limiting embodiments of the present disclosure are directed to a polynucleotide encoding any of the antibodies or functional fragments thereof disclosed or otherwise contemplated herein.

In a particular (but non-limiting) embodiment, a portion of the polynucleotide encoding a heavy chain of the antibody or functional fragment thereof is at least about 70% identical to SEQ ID NO:9, 29, 49, 69, 89, 109, 129, 149, 169, 189, 209, 229, or 249 (and/or a portion of the polynucleotide encoding a heavy chain variable region of the antibody or functional fragment thereof is at least about 70% identical to SEQ ID NO:19, 39, 59, 79, 99, 119, 139, 159, 179, 199, 219, 239, or 259), such as (but not limited to) at least about 75% identical, at least about 80% identical, at least about 85% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:9, 29, 49, 69, 89, 109, 129, 149, 169, 189, 209, 229, or 249 and/or SEQ ID NO:19, 39, 59, 79, 99, 119, 139, 159, 179, 199, 219, 239, or 259.

In yet another particular (but non-limiting) embodiment, and alternatively and/or in addition to the above embodiment, a portion of the polynucleotide encoding a light chain of the antibody or functional fragment thereof is at least about 70% identical to SEQ ID NO:13, 33, 53, 73, 93, 113, 133, 153, 173, 193, 213, 233, or 253 (and/or a portion of the polynucleotide encoding a light chain variable region of the antibody or functional fragment thereof is at least about 70% identical to SEQ ID NO:20, 40, 60, 80, 100, 120, 140, 160, 180, 200, 220, 240, or 260), such as (but not limited to) at least about 75% identical, at least about 80% identical, at least about 85% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:13, 33, 53, 73, 93, 113, 133, 153, 173, 193, 213, 233, or 253 and/or SEQ ID NO:20, 40, 60, 80, 100, 120, 140, 160, 180, 200, 220, 240, or 260.

In yet another particular (but non-limiting) embodiment, a portion of the polynucleotide encoding a heavy chain of the antibody or functional fragment thereof is at least about 90% identical to SEQ ID NO:9, 29, 49, 69, 89, 109, 129, 149, 169, 189, 209, 229, or 249 and/or a portion of the polynucleotide encoding a light chain of the antibody or functional fragment thereof is at least about 90% identical to SEQ ID NO:13, 33, 53, 73, 93, 113, 133, 153, 173, 193, 213, 233, or 253.

In yet another particular (but non-limiting) embodiment, a portion of the polynucleotide encoding a heavy chain variable region of the antibody or functional fragment thereof is at least about 90% identical to SEQ ID NO:19, 39, 59, 79, 99, 119, 139, 159, 179, 199, 219, 239, or 259 and/or a portion of the polynucleotide encoding a light chain variable region of the antibody or functional fragment thereof is at least about 90% identical to SEQ ID NO:20, 40, 60, 80, 100, 120, 140, 160, 180, 200, 220, 240, or 260.

In another particular (but non-limiting) embodiment, the portion of the sequence corresponding to the heavy chain of the antibody or functional fragment thereof and/or the portion of the sequence corresponding to the light chain of the antibody or functional fragment thereof differs from SEQ ID NO:9, 29, 49, 69, 89, 109, 129, 149, 169, 189, 209, 229, or 249 or SEQ ID NO:13, 33, 53, 73, 93, 113, 133, 153, 173, 193, 213, 233, or 253, respectively (and/or the portion of the sequence corresponding to the heavy chain variable region of the antibody or functional fragment thereof and/or the portion of the sequence corresponding to the light chain variable region of the antibody or functional fragment thereof differs from SEQ ID NO:19, 39, 59, 79, 99, 119, 139, 159, 179, 199, 219, 239, or 259 or SEQ ID NO:20, 40, 60, 80, 100, 120, 140, 160, 180, 200, 220, 240, or 260, respectively), by less than about 100 nucleotides, less than about 90 nucleotides, less than about 80 nucleotides, less than about 75 nucleotides, less than about 70 nucleotides, less than about 60 nucleotides, less than about 50 nucleotides, less than about 45 nucleotides, less than about 40 nucleotides, less than about 35 nucleotides, less than about 30 nucleotides, less than about 25 nucleotides, less than about 20 nucleotides, less than about 15 nucleotides, less than about 10 nucleotides, less than about 9 nucleotides, less than about 8 nucleotides, less than about 7 nucleotides, less than about 6 nucleotides, less than about 5 nucleotides, less than about 4 nucleotides, less than about 3 nucleotides, less than about 2 nucleotides, or less than about 1 nucleotide.

In yet another particular (but non-limiting) embodiment, the portion of the sequence corresponding to the heavy chain of the antibody or functional fragment thereof differs from SEQ ID NO:9, 29, 49, 69, 89, 109, 129, 149, 169, 189, 209, 229, or 249 by less than about 100 nucleotides, and/or the portion of the sequence corresponding to the light chain of the antibody or functional fragment thereof differs from SEQ ID NO:13, 33, 53, 73, 93, 113, 133, 153, 173, 193, 213, 233, or 253 by less than about 70 nucleotides.

In yet another particular (but non-limiting) embodiment, the portion of the sequence corresponding to the heavy chain variable region of the antibody or functional fragment thereof differs from SEQ ID NO:19, 39, 59, 79, 99, 119, 139, 159, 179, 199, 219, 239, or 259 by less than about 35 nucleotides, and/or the portion of the sequence corresponding to the light chain variable region of the antibody or functional fragment thereof differs from SEQ ID NO:20, 40, 60, 80, 100, 120, 140, 160, 180, 200, 220, 240, or 260 by less than about 34 nucleotides.

Certain non-limiting embodiments of the present disclosure are directed to a vector comprising any of the polynucleotides encoding an antibody or functional fragment thereof described or otherwise contemplated herein.

Certain non-limiting embodiments of the present disclosure are directed to a recombinant host cell comprising any of the polynucleotides encoding an antibody or functional fragment thereof described or otherwise contemplated herein. Certain non-limiting embodiments of the present disclosure are directed to a recombinant host cell comprising any of the vectors described or otherwise contemplated herein.

Certain non-limiting embodiments of the present disclosure are directed to a method of producing an antibody or functional fragment thereof which can specifically bind to naloxone and/or naltrexone. The method comprises: (a) culturing any of the recombinant host cells described or otherwise contemplated herein in a cell culture under conditions that allow for the expression of the antibody or functional fragment thereof encoded by the polynucleotide; and (b) isolating the antibody or functional fragment thereof from the cell culture.

Certain non-limiting embodiments of the present disclosure are directed to a method of detecting naloxone and/or naltrexone present in a biological sample. The method comprises: contacting the biological sample with any of the antibodies or functional fragments thereof disclosed or otherwise contemplated herein under conditions whereby an antibody/naloxone and/or antibody/naltrexone complex is formed if naloxone and/or naltrexone, respectively, is present in the sample; and detecting any antibody/naloxone and/or antibody/naltrexone complex formed, wherein an amount of antibody/naloxone and/or antibody/naltrexone complex formed is directly proportional to an amount of naloxone and/or naltrexone, respectively, present in the sample.

In a particular (but non-limiting) embodiment, a label as described herein above is attached to the antibody/functional fragment for use in the detection of the antibody/naloxone and/or antibody/naltrexone complex.

Certain non-limiting embodiments of the present disclosure are directed to methods of substantially reducing (or substantially removing) naloxone and/or naltrexone interference from an opiate assay of a biological sample. The method comprises contacting the biological sample with one or more of any of the antibodies or functional fragments thereof disclosed or otherwise contemplated herein under conditions whereby an antibody/naloxone and/or antibody/naltrexone complex is formed if naloxone and/or naltrexone, respectively, is present in the sample; removing any antibody/naloxone and/or antibody/naltrexone complex formed; and performing the opiate assay on the biological sample in which naloxone and/or naltrexone has been substantially reduced/removed. This method may be utilized with an assay for any opiate as well as any opiate assay format. For example (but not by way of limitation), the opiate to be assayed may be codeine, hydrocodone, hydromorphone, morphine, oxycodone, oxymorphone, heroin (6-acetylmorphine), combinations thereof, and the like. Non-limiting examples of opiate assay formats include ELISAs, chip assays, LC/MS/MS, immunoassays, enzyme immunoassays, enzyme multiplied immunoassays, fluorescence polarization immunoassays, combinations thereof, and the like. Various types of opiate assays are well known and well used in the art. Thus, no further description thereof is deemed necessary to allow a person of ordinary skill in the art to perform the methods disclosed herein.

In a particular (but non-limiting) embodiment, the at least one antibody or functional fragment thereof used in the method of substantially reducing (or substantially removing) naloxone and/or naltrexone interference from an opiate assay includes at least two antibodies or functional fragments thereof: (1) at least one antibody or functional fragment thereof that specifically binds naloxone, and (2) at least one antibody or functional fragment thereof that specifically binds naltrexone.

Certain non-limiting embodiments of the present disclosure also include kits containing any of the antibodies/functional fragments and/or compositions disclosed or otherwise contemplated herein (such as the compositions comprising antibody/functional fragment attached to a detectable label or a solid support), as well as any other reagents that may be utilized in the assays/methods described herein. For example (but not by way of limitation), the kit may further include one or more components of the opiate assays described herein above. For example (but not by way of limitation), the kit may include an antibody or functional fragment thereof that binds to any of the opiates described or otherwise contemplated herein, for use in an opiate immunoassay.

The assay components/reagents of the compositions/kits/methods may be provided in any form that allows them to function in accordance with the present disclosure. For example, but not by way of limitation, each of the reagents may be provided in liquid form and disposed in bulk and/or single aliquot form within the kit. Alternatively, in a particular (but non-limiting) embodiment, one or more of the reagents may be disposed in the kit in the form of a single aliquot lyophilized reagent. The use of dried reagents in microfluidics devices is described in detail in U.S. Pat. No. 9,244,085 (Samproni), the entire contents of which are hereby expressly incorporated herein by reference.

In addition to the assay components/reagents described in detail herein above, the kits may further contain other reagent(s) for conducting any of the particular assays described or otherwise contemplated herein. The nature of these additional reagent(s) will depend upon the particular assay format, and identification thereof is well within the skill of one of ordinary skill in the art; therefore, no further description thereof is deemed necessary. Also, the components/reagents present in the kits may each be in separate containers/compartments, or various components/reagents can be combined in one or more containers/compartments, depending on the cross-reactivity and stability of the components/reagents. In addition, the kit may include a microfluidics device in which the components/reagents are disposed.

The relative amounts of the various components/reagents in the kits can vary widely to provide for concentrations of the components/reagents that substantially optimize the reactions that need to occur during the assay methods and further to optimize substantially the sensitivity of an assay. Under appropriate circumstances, one or more of the components/reagents in the kit can be provided as a dry powder, such as a lyophilized powder, and the kit may further include excipient(s) for dissolution of the dried reagents; in this manner, a reagent solution having the appropriate concentrations for performing a method or assay in accordance with the present disclosure can be obtained from these components. Positive and/or negative controls may also be included with the kit. In addition, the kit can further include a set of written instructions explaining how to use the kit. A kit of this nature can be used in any of the methods described or otherwise contemplated herein.

EXAMPLES

Examples are provided hereinbelow. However, the present disclosure is to be understood to not be limited in its application to the specific experimentation, results, and laboratory procedures disclosed herein. Rather, the Examples are simply provided as one of various embodiments and are meant to be exemplary, not exhaustive.

Example 1: Production of Immunogens Comprising Naloxone and Naltrexone Conjugates This Example illustrates the production of various conjugates containing naloxone or naltrexone through multiple C-position linkages.

Materials and Equipment: The compounds were purified on a Shimadzu HPLC system equipped with a Silica-bond—C18 reverse phase column. The chemical reactions were monitored by TLC (thin layer chromatography) using Silica gel plates from Analtech Inc. (Newark, DE). The silica gel plates were visualized using UV short wave (254 nm). All chemicals were obtained from Sigma Aldrich (St. Louis, MO), Fluka (Waltham, MA), Thermo Scientific (Waltham, MA), and VWR (Radnor, PA), and were used as received. $^1$H NMR was recorded on a Bruker ULTRASHIELD™ 600 MHz spectrometer (Bruker, Billerica, MA) Chemical shifts were reported in parts per million (ppm, δ) and related to tetramethylsilane or with deuterated solvent as internal reference. NMR abbreviations used are: s (singlet), br s (broad singlet), d (doublet), t (triplet), q (quartet), dd (doublet of doublets), dt (doublet of triplets), td (triplet of doublets), ddd (doublet of doublet of doublets), J (coupling constant), Hz (Hertz). ESI-MS spectra were recorded on an Agilent HPLC 1290 single quad system equipped with a 6130 mass detector at Siemens Healthineers analytical facilities (Newark, DE). UV: Carry 60 was used for OD280 and BCA concentration measurements.

Figure 2:
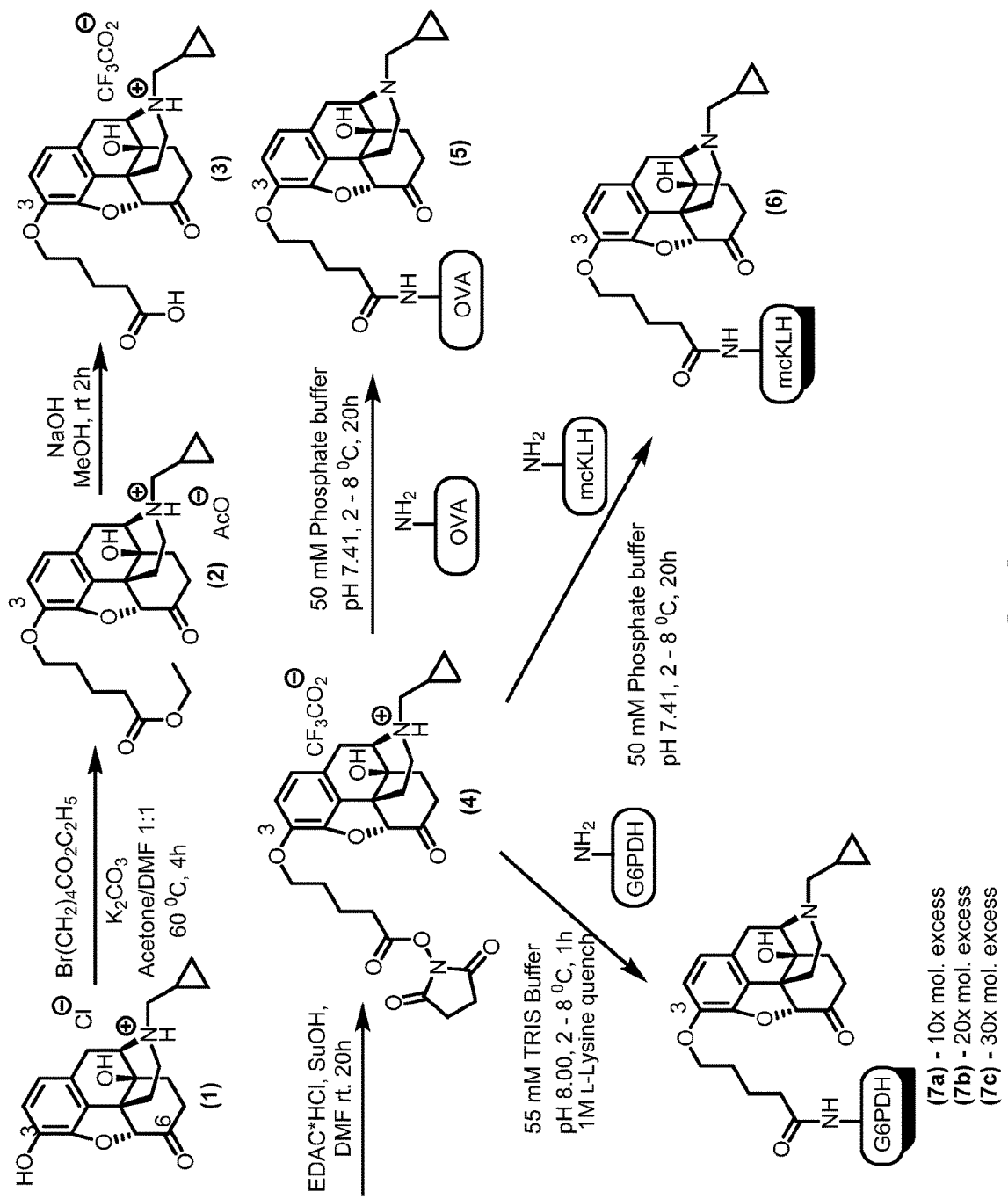
FIG. 2 schematically depicts syntheses of naltrexone hapten, KLH immunogen, and ovalbumin and G6PDH conjugates through C-3 position linkage.

The following abbreviations have the meanings set forth below:

BCA assay—Bicinchoninic acid assay
eq.—molar equivalent
g—grams
mg—milligram
mmol, mM—millimole
nm—nanometer
CV—column volume
$cm^2$—square centimeter
DCM—Dichloromethane
MeOH—Methanol
MeOD-$d_4$—Deuterated Methanol having 4 deuterium atoms (for NMR spectra)
DMF—N,N-Dimethylformamide
SuOH—N-hydroxysuccinimide
NaOAc—Sodium acetate
AcOH—Acetic acid
$AcO^-$—Acetate salt
EDAC·HCl—N-(3-Dimethylaminopropyl)-N'-ethylcarbodiimide hydrochloride
TFA—Trifluoroacetic acid
TLC—Thin layer chromatography
Rf—retention factor in TLC analysis
UV—Ultra Violet v/v—Volume ratio
ESI-MS—Electrospray ionization mass spectrometry
m/z—mass to charge ratio
NMR—Nuclear magnetic resonance
MHz—Megahertz
nG6PDH—native Glucose-6-phosphate dehydrogenase enzyme
β-NADH—Nicotinamide adenine dinucleotide
$G_6PDNa_2$—Glucose-6-phosphate disodium salt
OVA—Ovalbumin isolated from chicken egg white
mcKLH—Mariculture Keyhole Limpet Hemocyanin (ThermoFisher Scientific)
TRIS—Tris(hydroxymethyl)aminomethane
KU—dimeric protein complex of $nG_6PDH$
RPM—rotations per minute
CFA—Complete Freund's Adjuvant
IFA—Incomplete Freund's Adjuvant
ELISA—Enzyme-Linked Immunosorbant Assay
EIA—Enzyme Immunoassay
PBS—Phosphate Buffered Saline
HRP—Horseradish Peroxidase
TMB—3,3',5,5'-Tetramethylbenzidine
μL—Microliter
μg—Microgram
$V_H$—Variable Heavy Chain
$V_L$—Variable Light Chain
$C_H$—Constant Heavy Chain
$C_L$—Constant Light Chain
$NAD^+$—Oxidized Nicotinamide Adenine Dinucleotide
NADH—Reduced Nicotinamide Adenine Dinucleotide FIG. 2 schematically depicts syntheses of naltrexone hapten, KLH immunogen, and G6PDH conjugates through C-3 position linkage, as described in further detail herein below.

Preparation of Compound (2): In an oven-dried 50 mL round bottom flask equipped with a magnetic stir bar, naltrexone hydrochloride (1) (330 mg, 0.87 mmol) was added into the flask followed by DMF (5 mL), acetone (5 mL), and potassium carbonate (575 mg, 4.16 mmol, 4.78 eq.). The resulting reaction mixture was stirred at room temperature (rt.) for 5 minutes under nitrogen flow; then, ethyl-5-bromovaleric acid (375 μL, 495 mg, 2.36 mmol, ~2.71 eq.) was added into the mixture. The resulting reaction mixture was placed in an oil bath, and a condenser was attached to the round bottom flask. The reaction mixture was heated at 60° C. under stirring, and the reaction was completed after 4 hours by TLC [(DCM/MeOH 8/2 v/v) $Rf_{(1)}$=0.36, $Rf_{(2)}$=0.80]. The solvent was removed on a rotatory evaporator to give a white precipitate which was suspended in acetonitrile (2×10 mL) and filtered-off. The organic extract was concentrated on a rotatory evaporator and further dried overnight (16 h) on an oil pump to remove traces of volatiles. The product was suspended in Acetonitrile/Water (30/70 v/v containing 0.1% Acetic acid) and injected into a Shimadzu HPLC system for purification. Fractions containing the desired product were pooled out, concentrated on a rotatory evaporator, and lyophilized overnight (16-20 hours) to give 474.8 mg of compound (2) as a colorless powder in 93% yield. Compound (2): ESI-MS m/z calcd. for: $[C_{27}H_{36}NO_6]^+$ 470.3, found $[M+H]^+$=470.3; $^1H$ NMR (600 MHz, MeOD-$d_4$) δ: 6.86 (d, J=8.28 Hz, 1H), 6.81 (d, J=8.28 Hz, 1H), 4.97 (br s, 1H), 4.90 (s, 1H), 4.18-4.16 (m, 2H), 4.11 (q, J=7.14 Hz, 3H), 3.45 (d, J=19.74 Hz, 1H), 3.40 (dd, J=13.62, 7.20 Hz, 1H), 3.25 (dd, J=12.69, 4.35 Hz, 1H), 3.19 (dd, J=19.77, 6.27 Hz, 1H), 3.08-3.01 (m, 2H), 2.84 (td, J=13.28, 4.68 Hz, 1H), 2.74 (td, J=12.93, 3.86 Hz, 1H), 2.41-2.38 (m, 2H), 2.25 (dt, J=14.64, 3.00 Hz, 1H), 2.12-2.09 (m, 1H), 1.78-1.74 (m, 4H), 1.72-1.68 (m, 2H), 1.24 (t, J=7.14 Hz, 3H), 1.18-1.15 (m, 1H), 0.86-0.83 (m, 1H), 0.79-0.75 (m, 1H), 0.59-0.50 (m, 2H).

Preparation of compound (3): Compound (2) (474.8 mg, 0.81 mmol) was dissolved in MeOH (5 mL); then, sodium hydroxide 10N solution was added (0.53 mL), and the resulting reaction mixture was stirred at room temperature for 2 hours. The reaction completion was confirmed by checking by TLC [(DCM/MeOH 8/2 v/v), $Rf_{(2)}$=0.80 $Rf_{(3)}$=0.20]. The reaction mixture was acidified with HCl (12N, 0.5 mL) on an ice bath. The solvent was removed on a rotatory evaporator. The resulting white cake was suspended in acetonitrile (2 mL) and filtered-off. The filtrate was concentrated on a rotatory evaporator. Then water containing 0.1% TFA was added, and the resulting sample was lyophilized overnight (16-20 hours). After lyophilization, 471 mg of the title compound was obtained as a colorless powder in 100% yield. Compound (3): ESI-MS m/z calcd. for: $[C_{25}H_{32}NO_6]^+$ 442.2, found $[M+H]^+$=442.2; $^1H$ NMR (600 MHz, MeOD-$d_4$) δ: 6.85 (d, J=8.28 Hz, 1H), 6.78 (d, J=8.28 Hz, 1H), 4.86 (s, 1H), 4.20-4.18 (m, 2H), 3.91 (d, J=6.06 Hz, 1H), 3.37 (d, J=19.54 Hz, 1H), 3.19 (dd, J=13.32, 7.08 Hz, 1H), 3.11 (dd, J=12.66, 4.74 Hz, 1H), 3.07-3.06 (m, 1H), 3.02 (dd, J=14.55, 5.13 Hz, 1H), 2.89 (dd, J=13.38, 7.32 Hz, 1H), 2.76 (td, J=13.16, 4.90 Hz, 1H), 2.61 (td, J=12.82, 4.00 Hz, 1H), 2.34-2.32 (m, 2H), 2.26 (dt, J=14.61, 3.14 Hz, 1H), 2.04-2.02 (m, 1H), 1.81-1.76 (m, 4H), 1.70 (td, J=14.31, 3.52 Hz, 1H), 1.65 (dd, J=13.44, 3.00 Hz, 1H), 1.28-1.10 (m, 1H), 0.81-0.78 (m, 1H), 0.75-0.71 (m, 1H), 0.51-0.44 (m, 2H).

Preparation of compound (4): Compound (3) (10.6 mg, 0.019 mmol) was dissolved in degassed DMF (1.06 mL) to make a 10 mg/mL hapten-DMF solution; then, H-hydroxysuccinimide (6.58 mg, 0.057 mmol, 3 eq.) was added. The resulting reaction mixture was stirred until homogenous, and then EDAC·HCl (7.30 mg, 0.038 mmol, 2 eq.) was added. The resulting reaction mixture was stirred at room temperature for 20 hours and monitored by TLC [(DCM/MeOH 8/2 v/v), $Rf_{(3)}$=0.80, $Rf_{(4)}$=0.20)]. The formation of compound (4) was confirmed by TLC and MS direct loop: ESI m/z calcd. for: $[C_{29}H_{35}N_2O_8]^+$=539.2, found $[M+H]^+$=539.3 and $[M+Na]^+$=561.3. This compound (4) was used for the next reaction without any further purification.

Preparation of naltrexone OVA (5): OVA, (12 mg, 2.81×$10^{-4}$ mmol) was dissolved in 50 mM phosphate buffer, pH 7.41 (2 mL). The resulting protein solution was gentle vortexed until homogenous; then, it was cooled to 0-4° C. using an ice bath. The compound (4)—DMF solution (0.501 mL, 40 eq.) prepared previously was added dropwise under gentle swirling to the protein solution. The resulting reaction mixtures were rocked at 4° C. for 20 hours (overnight), then purified on the G-25M SEPHADEX® column (GE Healthcare, Chicago, IL) (CV=70 $cm^3$, pre-equilibrated with 2 CV of 50 mM phosphate buffer pH 7.00). The conjugate elution was monitored at $OD_{280}$. A sharp peak containing the desired naltrexone OVA conjugate was eluted in the interval 67-90 mL. Naltrexone OVA (5) was collected and concentrated. The concentration of the conjugate was determined by $OD_{280}$ to be 0.89 mg/ml. OVA conjugate (5) was obtained in a total of 9 mg with 75% yield.

Preparation of naltrexone KLH immunogen (6): Naltrexone KLH immunogen (6) was prepared using the same protocol as described for preparation of naltrexone OVA (5). In this case, 20 mg of mcKLH was used, which was treated with compound (4)—DMF solution (0.488 mL, 7×$10^{-3}$ mmol). After purification, the concentration of the conjugate was determined by BCA assay to be 0.96 mg/ml. KLH immunogen (6) was obtained in 15.35 mg with 76.8% yield.

Preparation of native G6PDH for bio-conjugation: Native G6PDH enzyme emulsion (5.5 mL, 5.5 KU, 64.35 mg) was centrifuged at 18,000 RPM, 4° C. for 30 minutes. The resulting clear aqueous layer was discarded and the remaining white cake was suspended in 55 mM TRIS buffer pH 8.00 (2.00 mL). The suspension was gentle swirled until dissolved; then, it was loaded onto a pre-equilibrated G-25M Sephadex column (CV=196 mL) with 55 mM TRIS buffer pH 8.00. The enzyme eluted in the interval 75-116 mL. The enzyme's concentration was adjusted to 5 mg/mL using an Amicon stirring cell concentrator (30,000 MW cut-off); then, it was cooled to 0-4° C. using an ice-bath. Glucose-6-phosphate di-sodium salt [G6PDNa$_2$] 240 mg was then added. The resulting reaction mixture was gentle swirled to 1 minute; then, β-NADH (120 mg) was added, and the resulting reaction mixture was stirred again for 1 minute. This enzyme solution was equally divided onto three plastic tubes (1.90 mL corresponding to 9.50 mg of enzyme per tube). The tubes 1-3 containing native G6PDHs were stored on an ice bath and ready for compound (4) addition.

Preparation of compound (4) for bio-conjugation: Compound (3) (9.71 mg, 0.017 mmol) was dissolved in degassed DMF (0.242 mL) to make a 40 mg/mL hapten-DMF solution; then, N-hydroxysuccinimide (6.20 mg, 0.054 mmol, ~3 eq.) was added. The resulting reaction mixture was stirred until homogenous, and then EDAC·HCl (7.30 mg, 0.038 mmol, 2 eq.) was added. The resulting reaction mixture was stirred for 22 hours at room temperature and monitored by TLC [(DCM/MeOH 8/2 v/v), Rf$_{(4)}$=0.80, Rf$_{(3)}$=0.20]. After the formation of compound (4), degassed DMF (0.242 μL) was added to make a 20 mg/mL compound (4)—DMF solution. ESI m/z calcd. for: $[C_{29}H_{35}N_2O_8]^+$=539.3, found $[M+H]^+$=539.3, $[M+Na]^+$=561.3; This compound (4) was used for bio-conjugation any without further purification.

Preparation of naltrexone nG6PDH enzyme (7a-c): In tube 1, compound (4) (243 μL—DMF solution) was added [10× molar excess of compound (4) to nG6PDH]. The reaction mixture was rocked at 2-8° C. for 1 hour; then, it was quenched with L-lysine [1M solution, 9 μL, 10× molar excess L-Lysine respective compound (4)]. The reaction mixture was then rocked at room temperature for 20 minutes. This conjugate was purified by a G-50M SEPHADEX® column (CV=67 cm$^2$) pre-equilibrated with 55 mM TRIS buffer pH 7.00 (2 CV). The conjugate was eluted in the interval 45-60 mL as a sharp peak. All fractions containing the desired conjugate were collected and concentrated. The concentration of the conjugate was determined by OD$_{280}$ to be 1.16 mg/mL. The G6PDH conjugate (7a) was obtained in 7.93 mg, with a yield of 83%.

In tube 2, compound (4) (485 μL of—DMF solution) was added (20× molar excess of compound (4) to nG6PDH); the reaction mixture was rocked at 2-8° C. for 1 hour; then, it was quenched with L-lysine [1M solution, 18 μL, 10× molar excess L-Lysine to compound (4)]. The reaction mixture was then rocked at room temperature for 20 minutes. This conjugate was purified by a G-50M SEPHADEX® column (CV=67 cm$^2$) pre-equilibrated with 55 mM TRIS buffer pH 7.00 (2 CV). The conjugate was eluted in the interval 45-60 mL as a sharp peak. All fractions containing the desired conjugate were collected and concentrated. The concentration of the conjugate was determined by OD$_{280}$ to be 1.25 mg/mL. The G6PDH conjugate (7b) was obtained in 8.09 mg, with a yield of 85%.

In tube 3, compound (4) (729 μL—DMF solution) was added [30× molar excess of compound (4) to nG6PDH]. The reaction mixture was rocked at 2-8° C. for 1 hour; then, it was quenched with L-lysine [1M solution, 27 μL, 10× molar excess L-Lysine to compound (4)]. The reaction mixture was then rocked at room temperature for 20 minutes. This conjugate was purified by a G-50M SEPHADEX® column (CV=67 cm$^2$) pre-equilibrated with 55 mM TRIS buffer pH 7.00 (2 CV). The conjugate was eluted in the interval 45-60 mL as a sharp peak. All fractions containing the desired conjugate were collected and concentrated. The concentration of the conjugate was determined by OD$_{280}$ to be 1.28 mg/mL. The G6PDH conjugate (7c) was obtained in 8.27 mg, with a yield of 87%.

Figure 3:
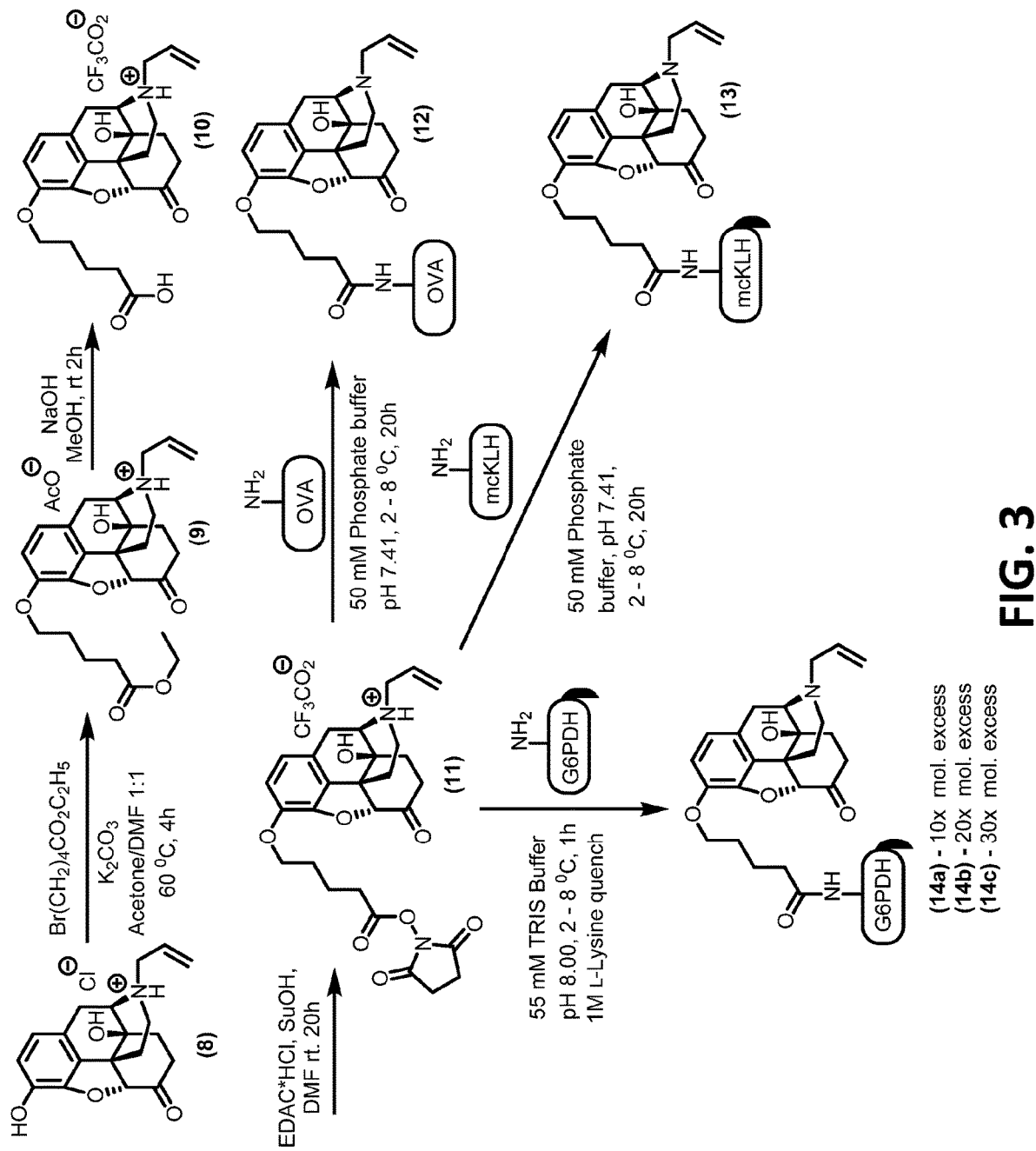
FIG. 3 schematically depicts syntheses of naloxone hapten, KLH immunogen, and ovalbumin and G6PDH conjugates through C-3 position linkage.

FIG. 3 schematically depicts syntheses of naloxone hapten, KLH immunogen, and G6PDH conjugates through C-3 position linkage, as described in further detail herein below.

Preparation of compound (9): This compound was prepared using the same synthetic method as described for preparation of compound (2). After lyophilization, compound (9) (465.5 mg) was obtained as a colorless powder in 99% yield. Compound (9): ESI-MS m/z calcd. for: $[C_{26}H_{34}NO_6]^+$=456.2, found $[M+H]^+$=456.2; $^1$H NMR (600 MHz, MeOD-d$_4$) δ: 6.87 (d, J=8.28 Hz, 1H), 6.82 (d, J=8.28 Hz, 1H), 6.03-5.96 (m, 1H), 5.71 (d, J=16.98 Hz, 1H), 5.64 (d, J=10.26 Hz, 1H), 4.90 (s, 1H), 4.20-4.16 (m, 2H), 4.11 (q, J=7.14 Hz, 2H), 3.98 (dd, J=13.59, 8.62 Hz, 1H), 3.89 (dd, J=13.62, 5.64 Hz, 1H), 3.78 (d, J=6.00 Hz, 1H), 3.48 (d, J=19.80 Hz, 1H), 3.31-3.28 (m, 1H), 3.10 (dd, J=19.80, 6.18 Hz, 1H), 3.03 (td, J=14.65, 4.97 Hz, 1H), 2.87-2.75 (m, 2H), 2.40 (m, 2H), 2.24 (dt, J=14.70, 3.00 Hz, 1H), 2.06-2.02 (m, 1H), 1.78-1.76 (m, 4H), 1.73-1.66 (m, 2H), 1.25 (t, J=7.14 Hz, 3H).

Preparation of compound (10): This compound was prepared using the same synthetic method as described for preparation of compound (3). After lyophilization, compound (10) (447 mg) was obtained as a colorless powder with a yield of nearly 100%. Compound (10): ESI-MS m/z calcd. for: $[C_{24}H_{30}NO_6]^+$=428.2, found $[M+H]^+$=428.2; $^1$H NMR (600 MHz, MeOD-d$_4$) δ: 6.82 (d, J=8.22 Hz, 1H), 6.75 (d, J=8.22 Hz, 1H), 5.99-5.91 (m, 1H), 5.48 (dd, J=17.13, 1.17 Hz, 1H), 5.43-5.41 (m, 2H), 4.82 (s 1H), 4.18-4.16 (m, 2H), 3.60 (dd, J=13.60, 7.53 Hz, 1H), 3.55 (dd, J=13.59, 6.03 Hz, 1H), 3.42 (d, J=5.88 Hz, 1H), 3.30 (s, 1H), 3.03 (td, J=14.55, 5.10 Hz, 1H), 2.96 (dd, J=12.48, 4.80 Hz, 1H), 2.85 (dd, J=19.32, 6.06 Hz, 1H), 2.65 (td, J=12.99, 5.04 Hz, 1H), 2.46 (td, J=12.63, 3.92 Hz, 1H), 2.36-2.33 (m, 2H), 2.22 (dt, J=14.52, 3.12 Hz, 1H), 1.97-1.94 (m, 1H), 1.80-1.76 (m, 4H), 1.65 (dd, J=14.25, 3.45 Hz, 1H), 1.61-1.58 (m, 1H).

Preparation of compound (11): This compound was prepared using the same synthetic method as described for preparation of compound (4).

Preparation of naloxone OVA (12): This conjugate was prepared using the same synthetic method as described for preparation of OVA conjugate (5).

Preparation of naloxone KLH Immunogen (13): This immunogen was prepared using the same synthetic method as described for preparation of KLH immunogen (6).

Preparation of naloxone nG6PDH [14(a-c)]: These nG6PDH conjugates were prepared using the same synthetic method as described for preparation of nG6PDHs [7(a-c)].

Figure 4:
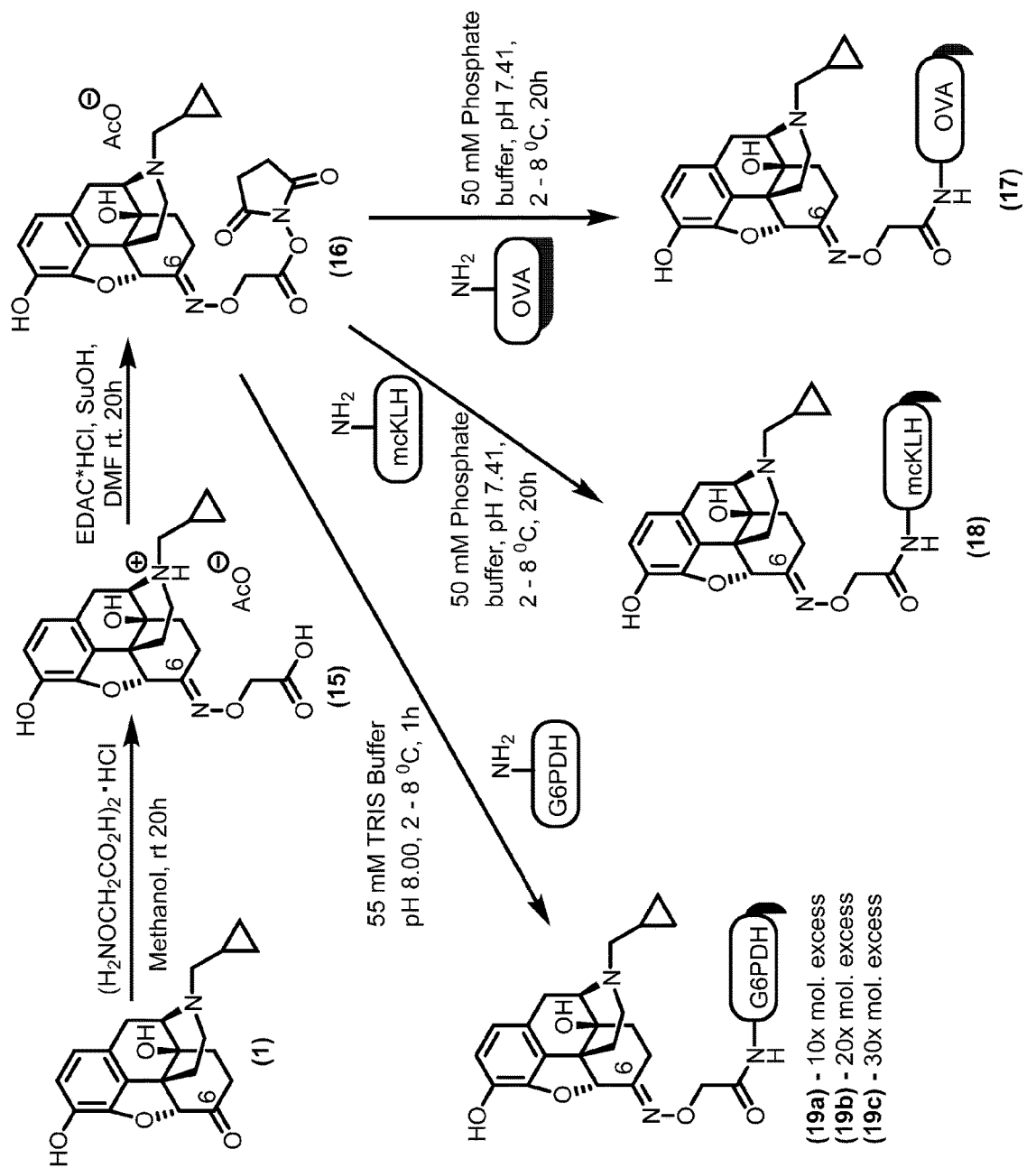
FIG. 4 schematically depicts syntheses of naltrexone hapten, KLH immunogen, and ovalbumin and G6PDH conjugates through C-6 position linkage.

FIG. 4 schematically depicts syntheses of naltrexone hapten, KLH immunogen, and G6PDH conjugates through C-6 position linkage, as described in detail herein below.

Preparation of compound (15): Naltrexone hydrochloride (1) (118 mg, 0.31 mmol) was dissolved in MeOH (7 mL); then, NaOAc (292 mg, 2.24 mmol) was added. The resulting reaction mixture was stirred at room temperature for 5 minutes; then, O-(carboxymethyl)hydroxylamine hemihydrochloride (210.7 mg, 1.92 mmol) was added into the mixture. The resulting reaction mixture was stirred at room temperature overnight (20 hours). TLC analysis of the reaction mixture showed reaction completion [(DCM/MeOH 8/2 v/v) $Rf_{(1)}$=0.4, $Rf_{(15)}$=0.02]. The solvent was removed on a rotatory evaporator to give a white suspension. Then, water/acetonitrile (1.4 mL/0.6 mL v/v) containing 0.1% AcOH was added. The crude reaction mixture was then injected into a preparative Shimadzu HPLC system for purification. Fractions containing the desired product were pooled together, concentrated on a rotatory evaporator, and lyophilized overnight (16-20 hours). This gave the compound (15) (124 mg) as a colorless powder in 75% yield. Compound (15): ESI-MS m/z calcd. for: $[C_{22}H_{27}NO_6]^+$ 415.2, found $[M+H]^+$=415.2, and $[M+Na]^+$=429.2; $^1H$ NMR (600 MHz, MeOD-$d_4$) δ: 6.76 (d, J=8.10 Hz, 1H), 6.72 (d, J=8.22 Hz, 1H), 5.06 (s, 1H), 4.66 (s, 2H), 3.99 (d, J=6.60 Hz, 1H), 3.42 (d, J=19.74 Hz, 1H), 3.38 (dd, J=13.32, 7.03 Hz, 1H), 3.17 (dd, J=12.99, 5.01 Hz, 1H), 3.12 (dd, J=19.86, 6.84 Hz, 1H), 2.97 (dd, J=13.62, 7.50 Hz, 1H), 2.91 (td, J=13.05, 4.04 Hz, 1H), 2.82 (ddd, J=17.76, 6.54, 1.86 Hz, 1H), 2.68 (td, J=13.43, 5.00 Hz, 1H), 2.65-2.59 (m, 1H), 1.80-1.76 (m, 2H), 1.51 (ddd, J=14.25, 12.09, 6.54 Hz, 1H), 1.17-1.10 (m, 1H), 0.88-0.84 (m, 1H), 0.80-0.75 (m, 1H), 0.57-0.50 (m, 2H).

Preparation of compound (16): This compound was prepared using the same synthetic method as described for preparation of compound (4).

Preparation of naltrexone OVA (17): This conjugate was prepared using the same synthetic method as described for preparation of OVA conjugate (5).

Preparation of naltrexone KLH Immunogen (18): This immunogen was prepared using the same synthetic method as described for preparation of KLH immunogen (6).

Preparation of naltrexone nG6PDH [19(a-c)]: These nG6PDH conjugates were prepared using the same synthetic method as described for preparation of nG6PDHs [7(a-c)].

Figure 5:
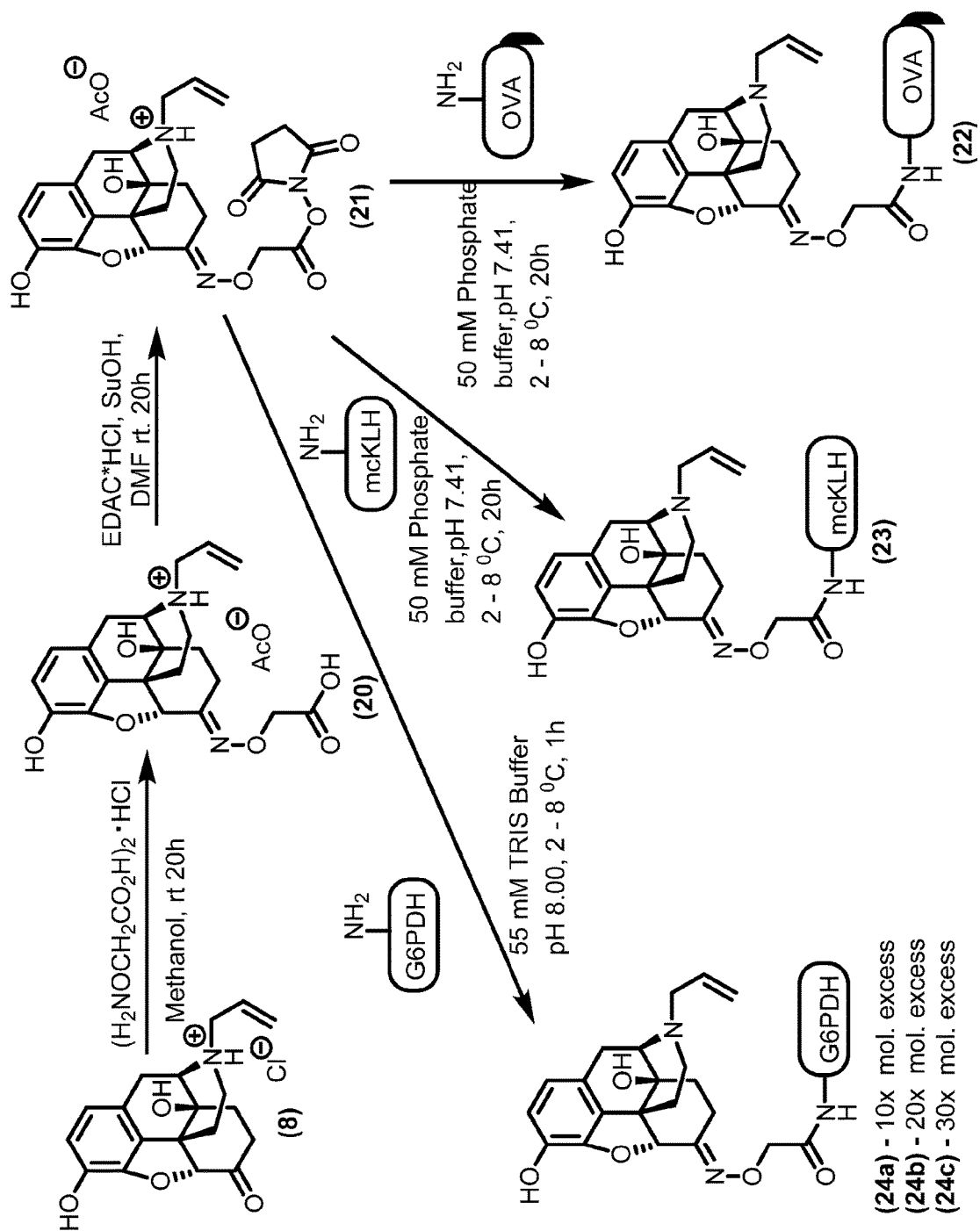
FIG. 5 schematically depicts syntheses of naloxone hapten, KLH immunogen, and ovalbumin and G6PDH conjugates through C-6 position linkage.

FIG. 5 schematically depicts syntheses of naloxone hapten, KLH immunogen, and G6PDH conjugates through C-6 position linkage, as described in detail herein below.

Preparation of compound (20): Naloxone hydrochloride (8) (110 mg, 0.27 mmol) was dissolved in MeOH (7 mL); then, NaOAc (260 mg, 2.00 mmol) was added. The resulting reaction mixture was stirred at room temperature for 5 minutes; then, O-(carboxymethyl)hydroxylamine hemihydrochloride (186 mg, 1.69 mmol) was added. The resulting reaction mixture was stirred at room temperature overnight. TLC analysis showed the reaction completion (DCM/MeOH 8/2 v/v $Rf_{(1)}$=0.40, $Rf_{(20)}$=0.02). The reaction mixture formed a white precipitate. The reaction mixture was concentrated on a rotatory evaporator to give a white suspension, which was dissolved in water containing 0.1% AcOH and injected into a Shimadzu HPLC for purification. Fractions containing the desired product were pooled together, concentrated on a rotatory evaporator, and lyophilized overnight (16-20 hours). This gave the compound (20) (125 mg) in 87% yield. Compound (20): ESI-MS m/z calcd. for: $[C_{21}H_{25}NO_6]^+$ 401.2, found $[M+H]^+$=401.2, $[M+Na]^+$=423.2; $^1H$ NMR (600 MHz, MeOD-$d_4$) δ: 6.74 (d, J=8.17 Hz, 1H), 6.70 (d, J=8.22 Hz, 1H), 5.98-5.90 (m, 1H), 5.68 (d, J=17.16 Hz, 1H), 5.64 (d, J=10.38 Hz, 1H), 5.04 (s, 1H), 4.64 (s, 2H), 3.95 (dd, J=13.65, 8.67 Hz, 1H), 3.81 (dd, J=13.68, 5.58 Hz, 1H), 3.63 (d, J=6.54 Hz, 1H), 3.43 (d, J=19.74 Hz, 1H), 3.22 (dd, J=12.93, 4.95 Hz, 1H), 3.02 (dd, J=19.80, 6.60 Hz, 1H), 2.92 (td, J=13.13, 4.10 Hz, 1H), 2.80 (ddd, J=17.73, 6.39, 1.89 Hz, 1H), 2.65 (td, J=13.47, 5.04 Hz, 1H), 2.61-2.54 (m, 1H), 1.77 (dd, J=13.68, 3.30 Hz, 1H), 1.71 (ddd, J=14.26, 6.67, 2.38 Hz, 1H), 1.45 (ddd, J=14.26, 12.20, 6.43 Hz, 1H).

Preparation of compound (21): This compound was prepared using the same synthetic method as described for preparation of compound (4).

Preparation of naloxone OVA (22): This conjugate was prepared using the same synthetic method as described for preparation of OVA conjugate (5).

Preparation of naloxone KLH Immunogen (23): This immunogen was prepared using the same synthetic method as described for preparation of KLH immunogen (6).

Preparation of naloxone nG6PDH [24(a-c)]: These nG6PDH conjugates were prepared using the same synthetic method as described for preparation of nG6PDHs [7(a-c)].

Example 2: Production of Anti-Naloxone and Anti-Naltrexone Monoclonal Antibodies This Example illustrates the production of specific monoclonal antibodies to naloxone and naltrexone. These monoclonal antibodies can be used in naloxone and naltrexone specific assays, respectively.

In addition, these monoclonal antibodies can be used as blocker antibodies in opiate assays (such as, but not limited to, a hydrocodone assay). It is commonly observed that various opiate assays provide false positive results for patients undergoing naloxone/naltrexone treatment. In such cases, the patients can be screened using the naloxone/naltrexone specific assays disclosed herein to rule out any false positives. In addition (and/or alternatively), biological samples utilized in various opiate assays can be subjected to a pretreatment step with these naloxone/naltrexone-specific monoclonal antibodies to remove any naloxone/naltrexone present in the samples and thus prevent or substantially reduce any naloxone/naltrexone interference observed in quantitative clinical opiate assays.

Figure 6:
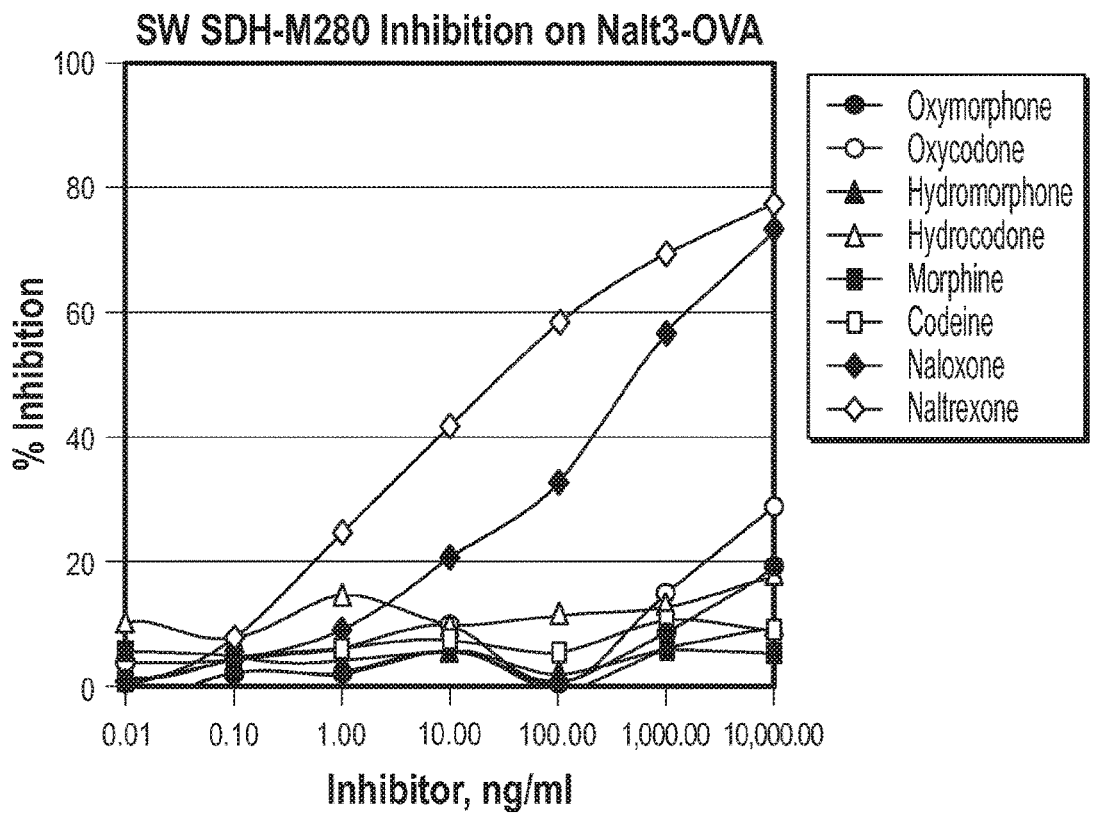
FIG. 6 graphically depicts ELISA inhibition assays for various opiates conducted using various bleeds obtained from selected mice immunized with naloxone- or naltrexone-KLH conjugates.
Figure 6:
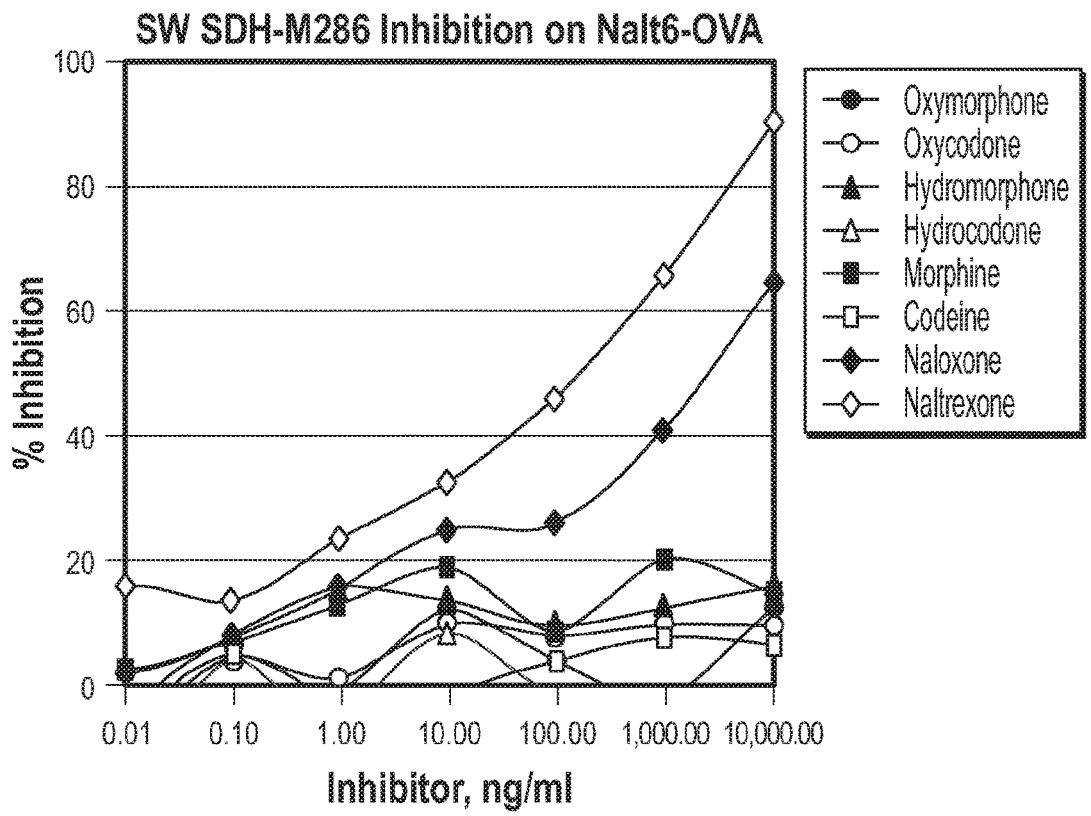
Figure 6:
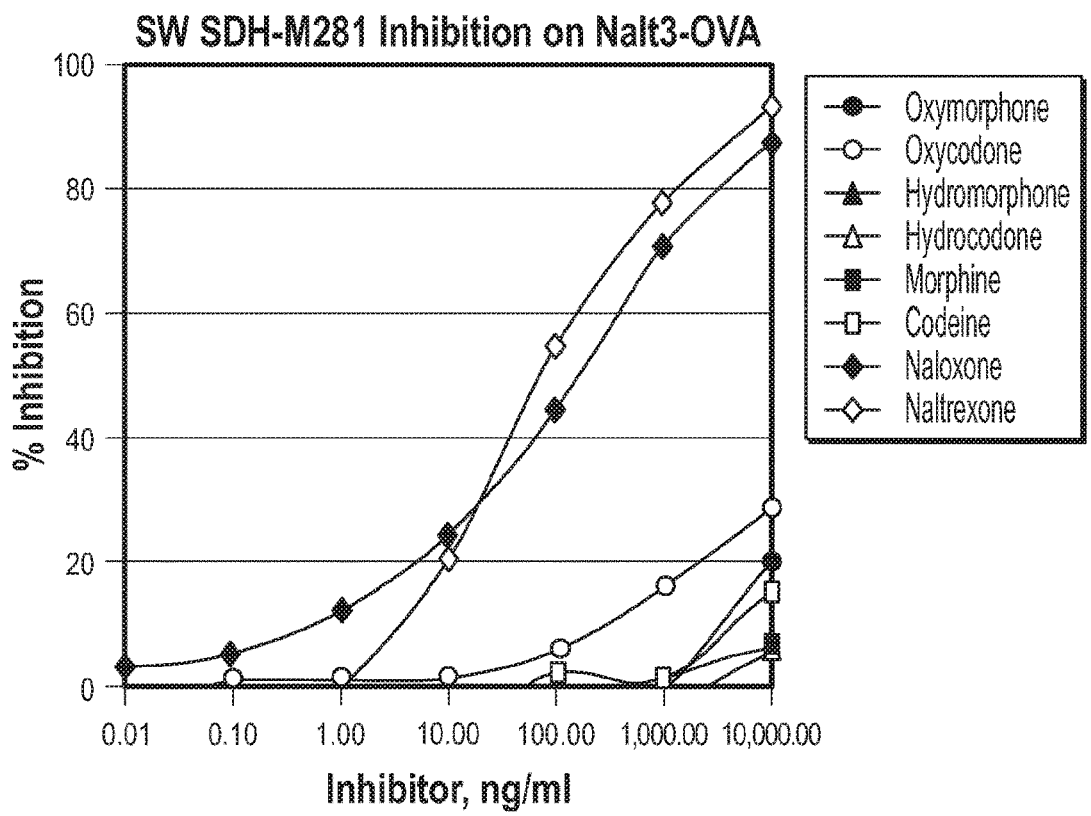
Figure 6:
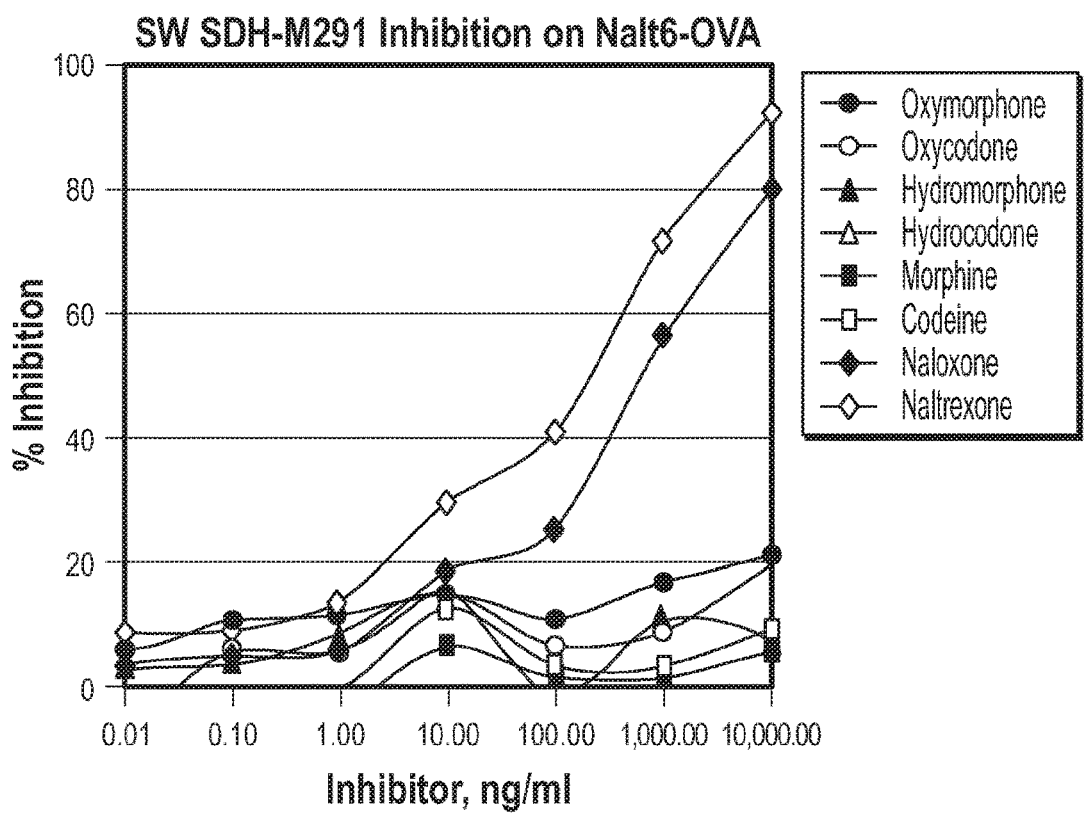
Figure 6:
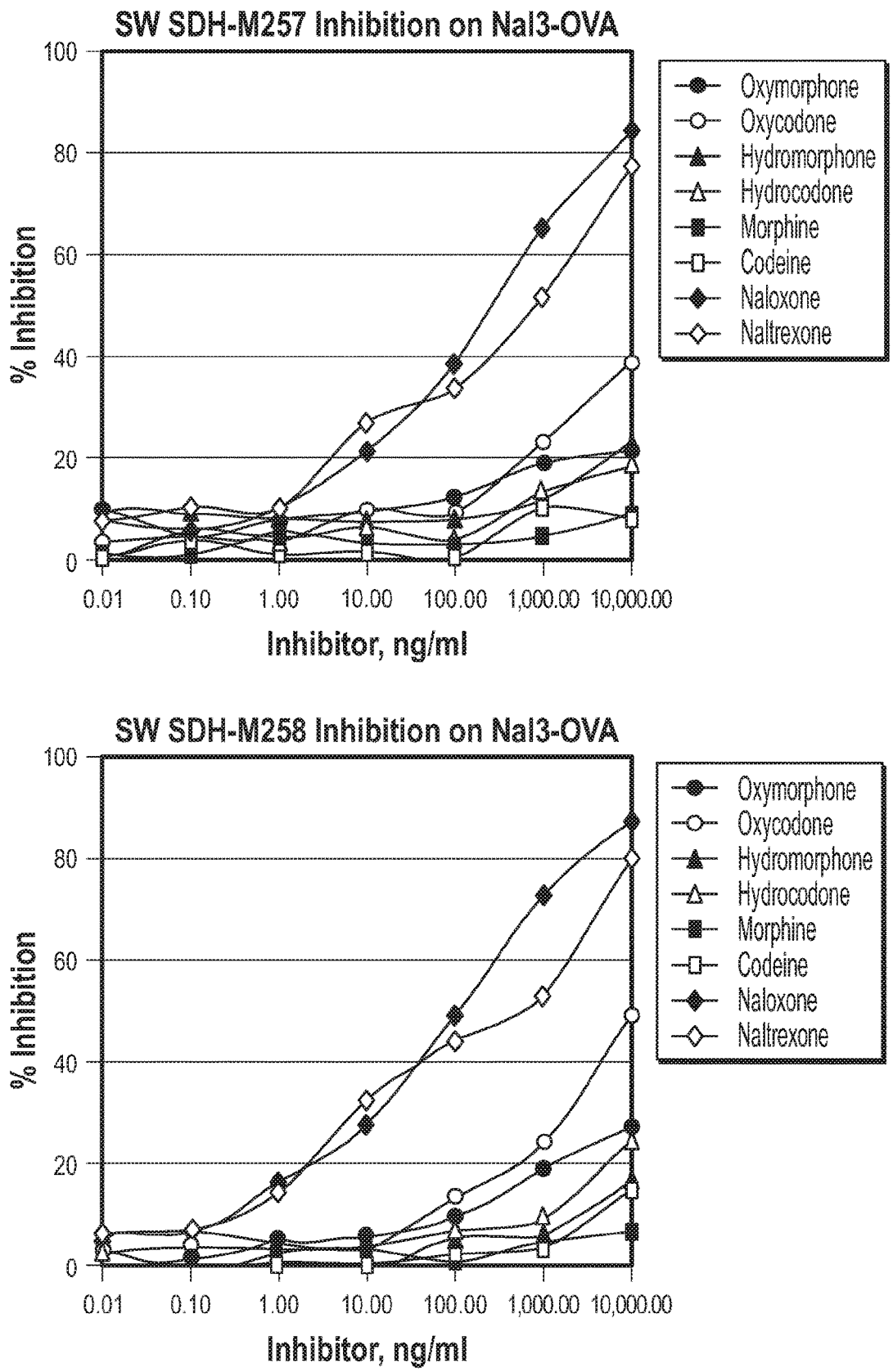
Figure 6:
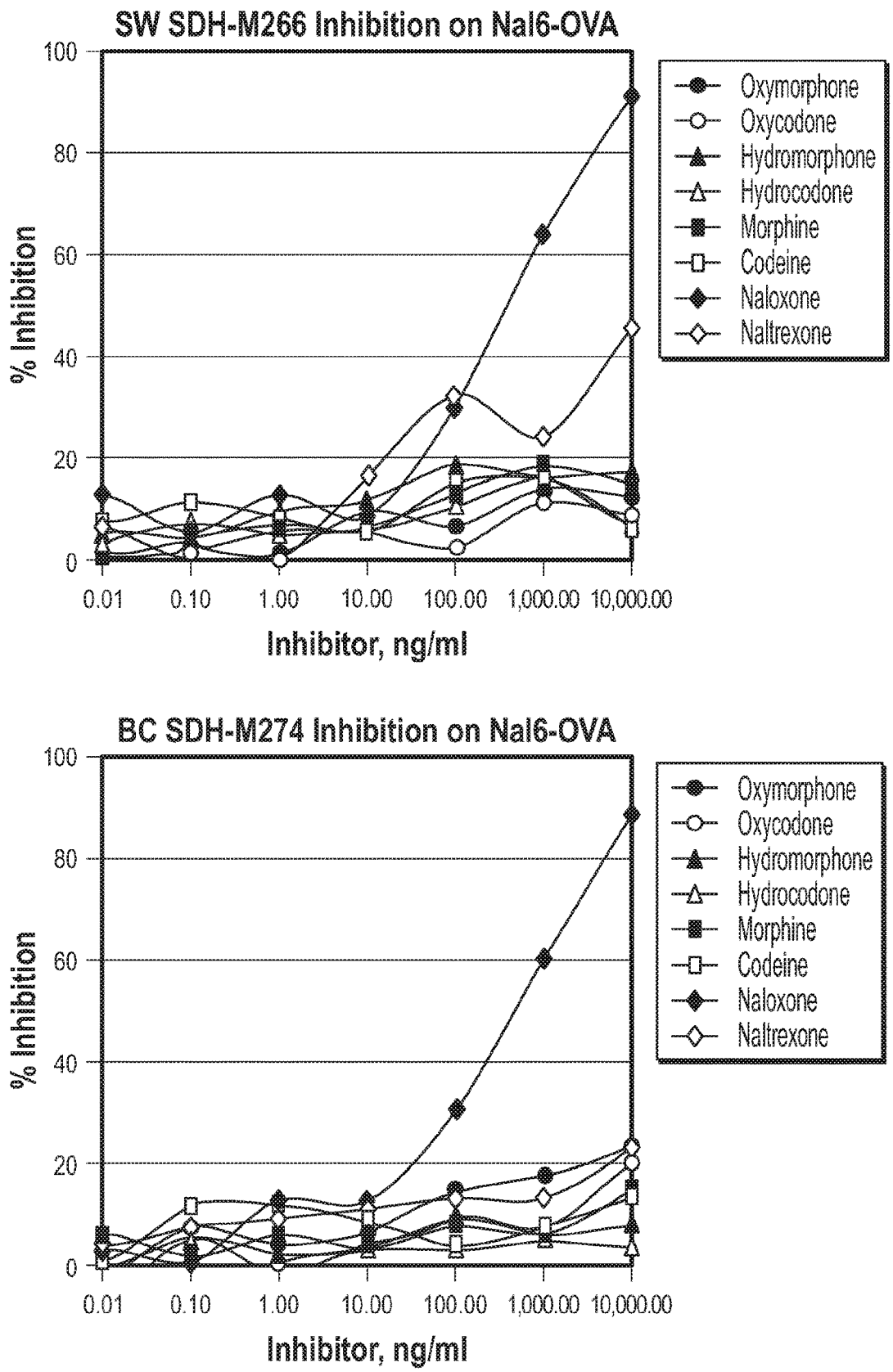

In this Example, various immunogens comprising naloxone or naltrexone attached to KLH at various positions were prepared and used as immunogens to immunize mice (e.g., BALB/c mice, Swiss Webster mice, or an Ai strain of mice) intraperitoneally. Mice were immunized three or more times to generate high titer immune response. Primary immunization was performed using adjuvants like CFA (immunogen emulsified using CFA), followed by subsequent booster immunizations using adjuvants like IFA. Following immunizations, mice were bled, and serum samples were isolated using centrifugation technique. Serum samples from these mice were tested for anti-naloxone and anti-naltrexone antibodies using a conjugate of naloxone and/or naltrexone with ovalbumin (ovalbumin conjugate). A microtiter plate ELISA was employed, and the antibodies were examined for binding to the ovalbumin conjugate and subsequently to free drug molecules using an inhibition ELISA. FIG. 6 shows inhibition ELISA results using eight important opioid drugs. The immunogens used to obtain the mice bleeds shown in FIG. 6 are as follows. Top row, left to right: naltrexone 3-KLH (Formula III, wherein $R_2$ is a cyclopropyl); naltrexone 6-KLH (Formula VI, wherein $R_2$ is a cyclopropyl); naloxone 3-KLH (Formula III, wherein $R_2$ is an allyl); and naloxone 3-KLH. Bottom row, left to right: naltrexone 3-KLH; naltrexone 6-KLH; naloxone 6-KLH (Formula VI, wherein $R_2$ is an allyl); and naloxone 6-KLH.

Mice with good anti-drug antibody titers and binding to free drug in the ELISA inhibition assays were selected to proceed with generation of monoclonal antibodies, in a similar manner to that described in U.S. Pat. No. 9,815,907

(issued to Sharma et al. on Nov. 14, 2017). In particular, mice with highest titers and best specificity were boosted three days prior to fusion. On the day of fusion, spleen cells were harvested from these mice and were fused with myeloma cell line P3X63Ag8.653 using PEG-assisted fusion protocols. After about ten days, hybridoma supernatants were screened for anti-naloxone and anti-naltrexone antibodies using a plate ELISA (direct binding and inhibition ELISA for specificity). Positive clones were further expanded and sub-cloned, and supernatants were purified using a Protein A SEPHAROSE® (GE Healthcare, Chicago, IL) column. Purified antibody samples were tested using ELISA for binding to the immunogen (i.e., a conjugate of drug-carrier protein) and to free opioids.

Table 1 lists the designations for some of the selected hybridoma clones generated against naloxone and naltrexone drug molecules, as described herein.

TABLE 1

List of Monoclonal Antibodies Generated Against Naloxone- and Naltrexone-KLH Conjugates

| mAb Designation | Drug |
|---|---|
| 179B 9G1.1 | Naloxone |
| 179B 9E12 | Naloxone |
| 179B 10A7 | Naloxone |
| 179A 6H6 | Naloxone |
| 179B 9E7 | Naloxone |
| 180A 3D3 | Naltrexone |
| 180B 13F7 | Naltrexone |
| 180C 1F8 | Naltrexone |
| 180C 7G8 | Naltrexone |
| 180C 8A10 | Naltrexone |
| 180C 9D5 | Naltrexone |
| 180C 9G8 | Naltrexone |
| 180C 2A12 | Naltrexone |

Antibody solution (Immune mouse bleeds or hybridoma clones supernatant or purified antibody) was screened using an inhibition ELISA procedure according to the following protocol. Plates were coated with Naloxone 3-Ovalbumin, Naloxone 6-Ovalbumin, Naltrexone 3-Ovalbumin, or Naltrexone 6-Ovalbumin at 1 µg/mL in phosphate buffered saline at 50 µL per well. Plate coating was performed for 1 hour or more at room temperature or overnight at about 2° C. to 8° C. The plates were then flicked dry and blocked with 200 µL per well of blocking buffer solution (0.5% Casein solution in PBS containing 0.05% TWEEN® 20 surfactant (Croda International PLC, Snaith, United Kingdom). Plate blocking was performed by incubation for 30 minutes or more at room temperature with plate shaking. The plates were washed using a plate washer (BioTek®, Winooski, VT) with plate stacker with the washing buffer being MILLIQ® water (Millipore Corporation, Billerica, MA) containing 0.05% TWEEN® 20. The monoclonal antibody to be screened was then added to each well along with free drug as follows: 25 µL per well of appropriately diluted culture supernatant (or antibody solution) and added 25 µL of 20 µg/mL of free drug. Incubation was performed for about 1 hour at room temperature with plate shaking. The plate was washed. An enzyme conjugate (goat anti-mouse IgG coupled to HRP diluted in blocking buffer diluted to 1:3000) was added at 50 µL per well. Incubation was performed for about 1 hour at room temperature with shaking. The plate was then washed, and a chromogenic solution (TMB from Moss Substrates, Pasadena MD) was added at a volume of 100 µL per well. If a desired antibody was present in the hybridoma supernatant, then a decrease in optical density was observed compared to the well containing no free drug. The plates were read at 650 nm wavelength using an ELISA plate reader (Molecular Devices, San Jose, CA). Note: appropriate dilution of antibody solution was determined by performing a titration ELISA. The antibody dilution was chosen where around 1.0 optical density was observed.

Figure 7:
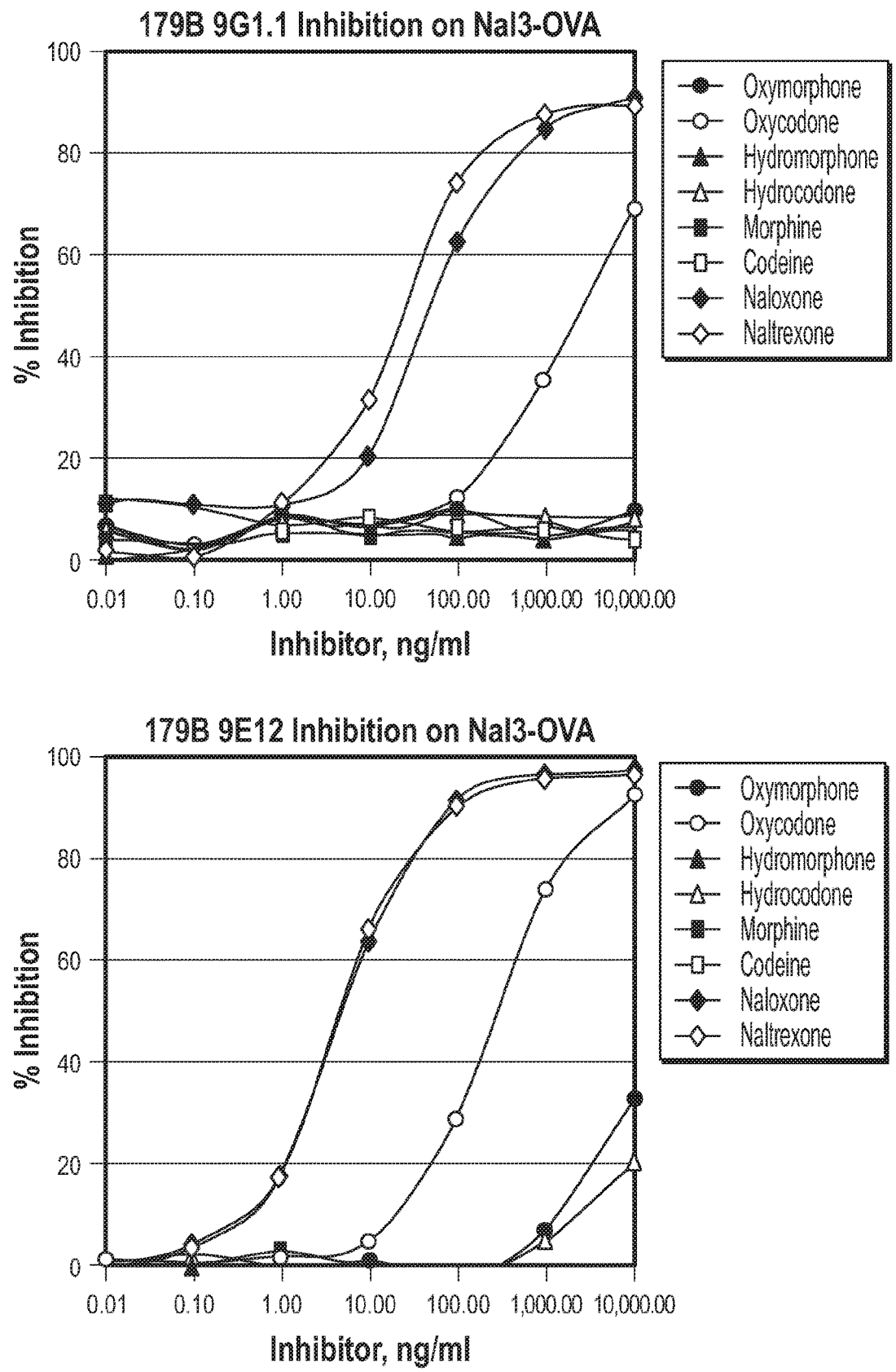
FIG. 7 graphically depicts ELISA inhibition assays for five selected anti-naloxone monoclonal antibodies using eight key opioids (immunogen indicated in lower right of Figure).
Figure 7:
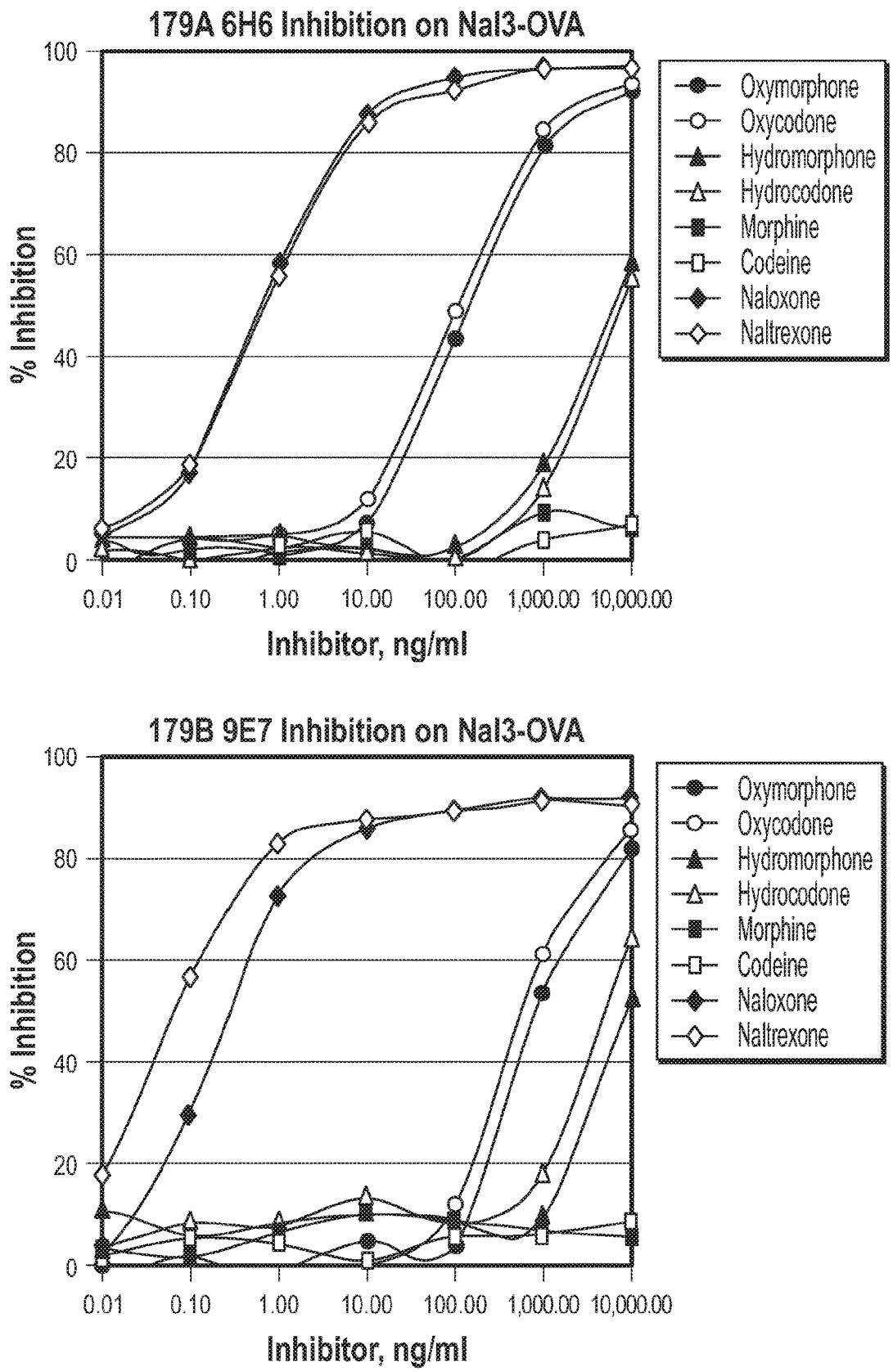
Figure 7:
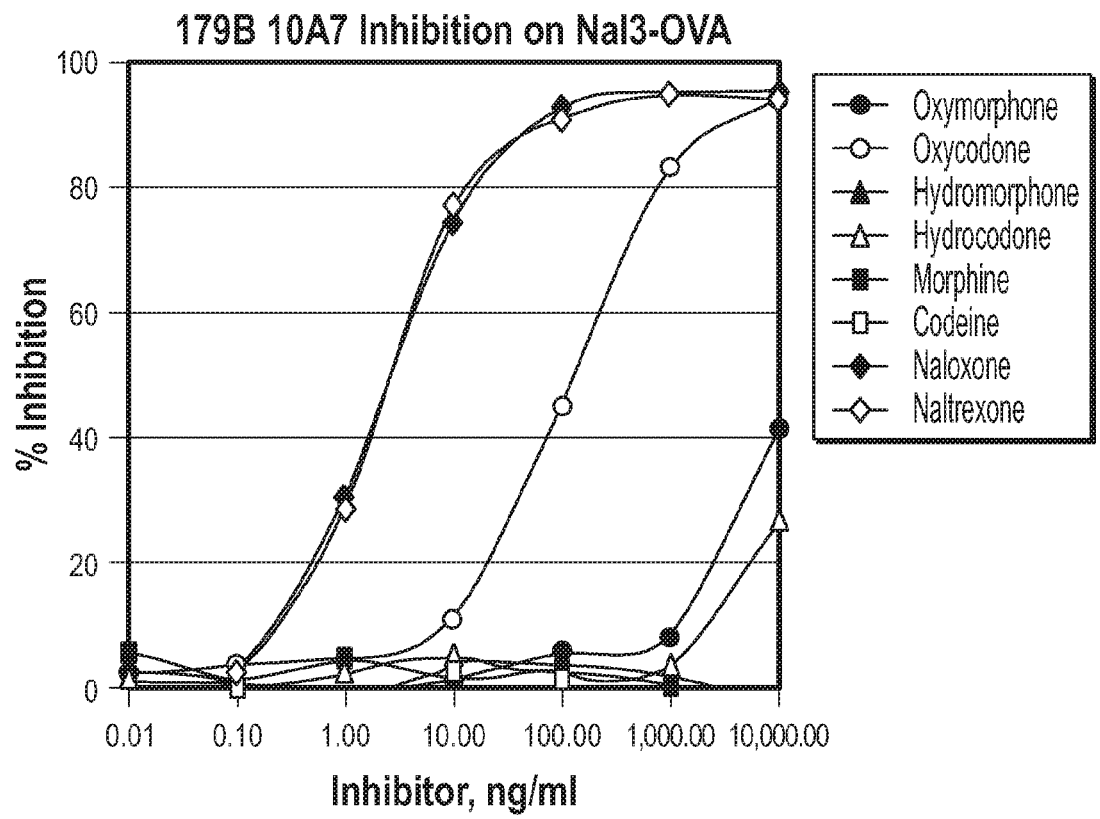
Figure 7:
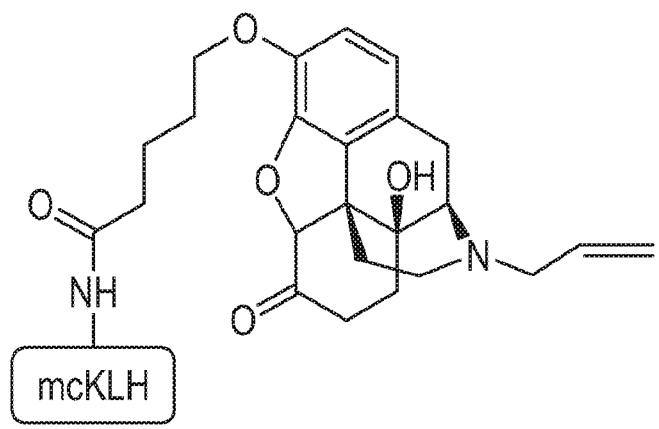
Figure 8:
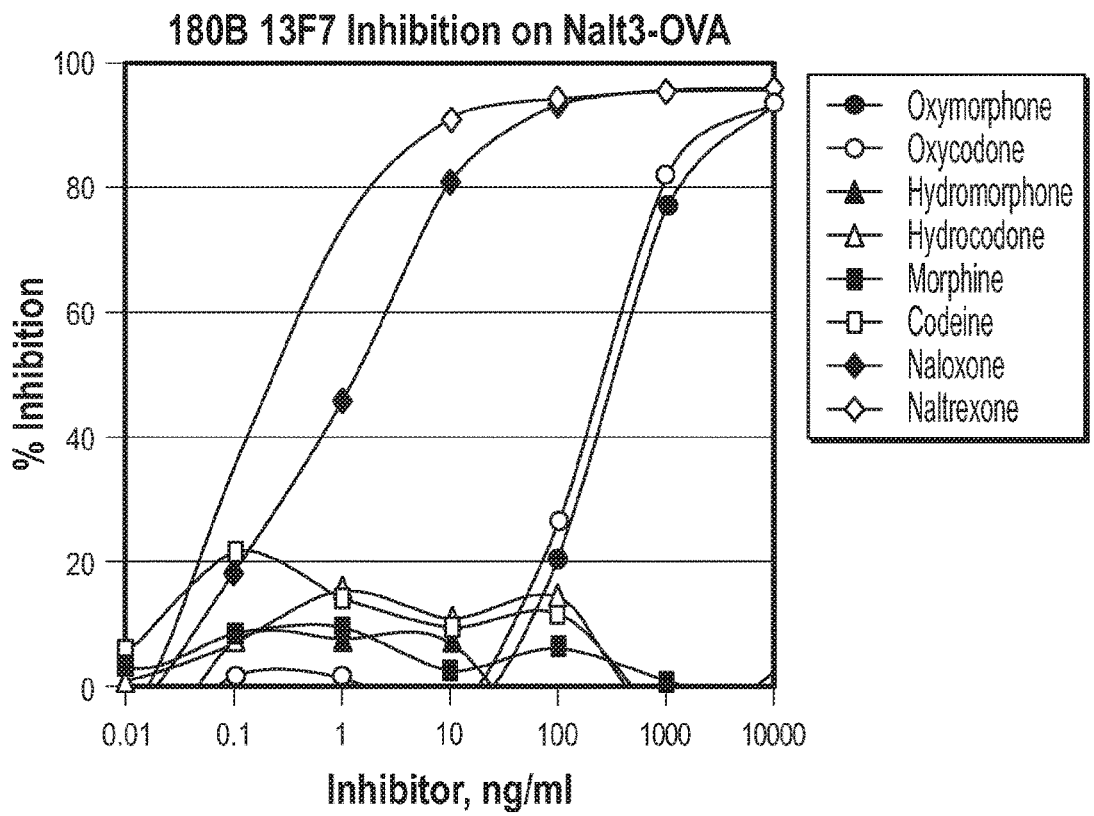
FIG. 8 graphically depicts ELISA inhibition assays for eight selected anti-naltrexone monoclonal antibodies using eight key opioids (immunogen indicated in lower panel of Figure).
Figure 8:
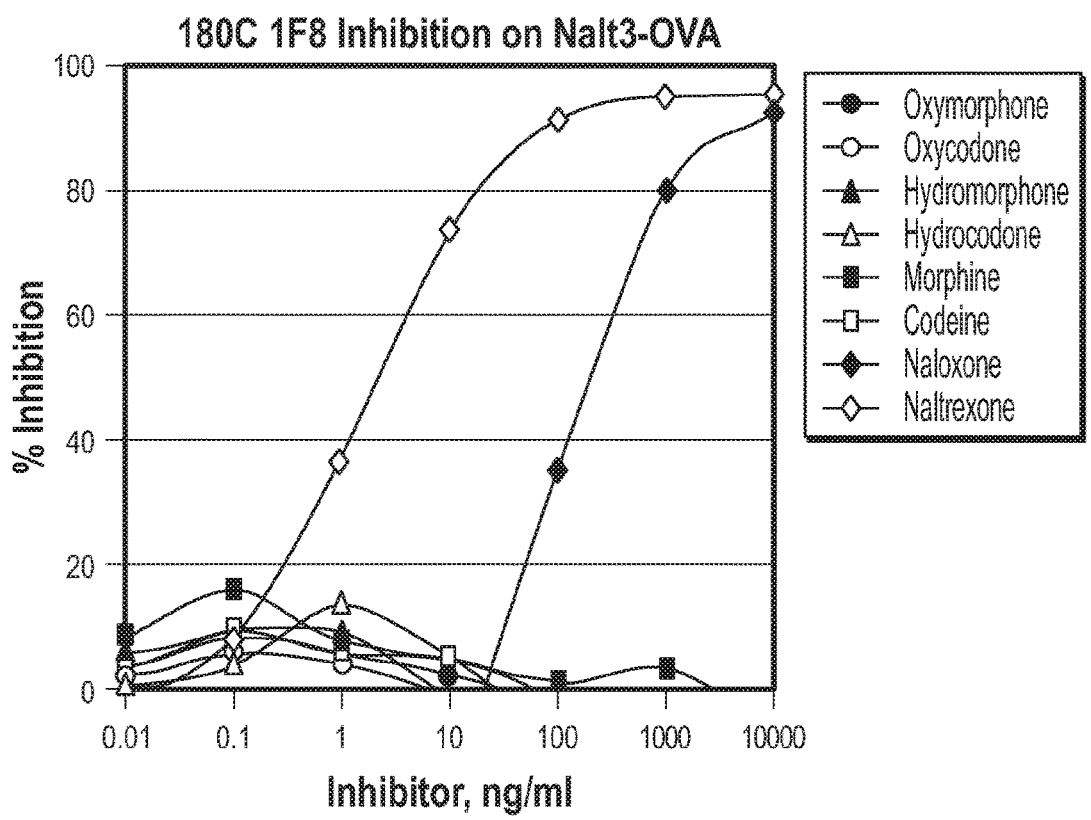
Figure 8:
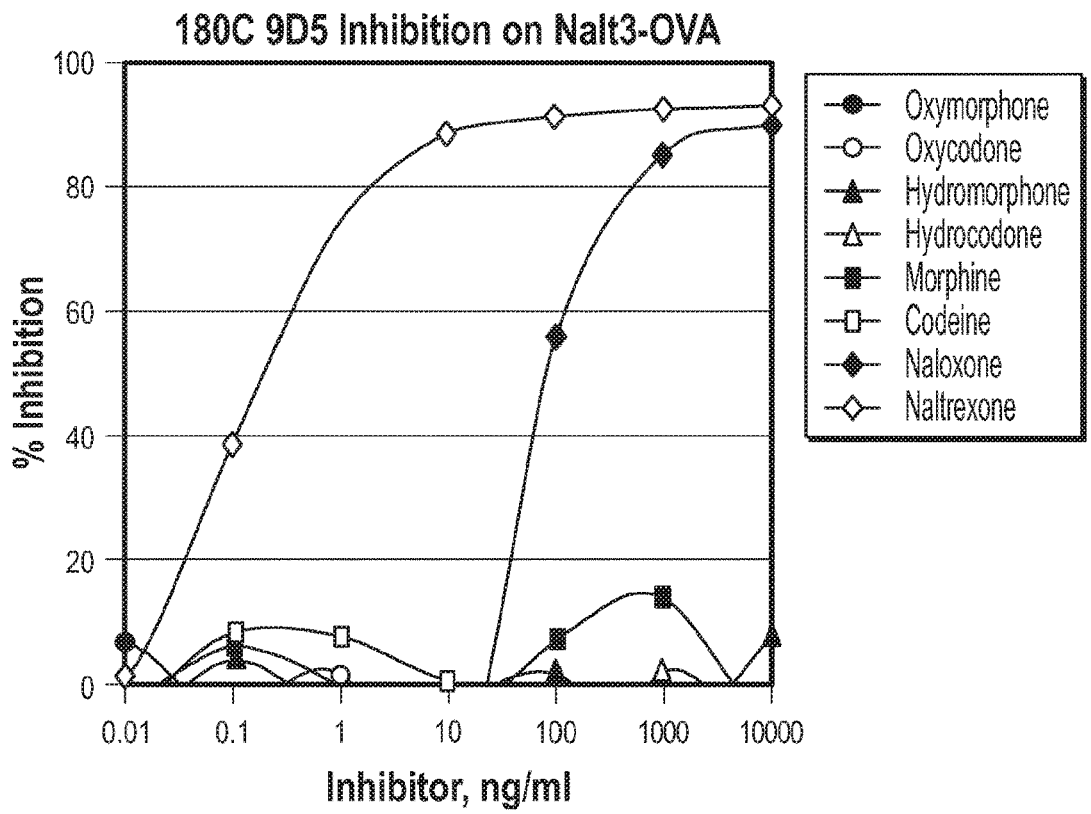
Figure 8:
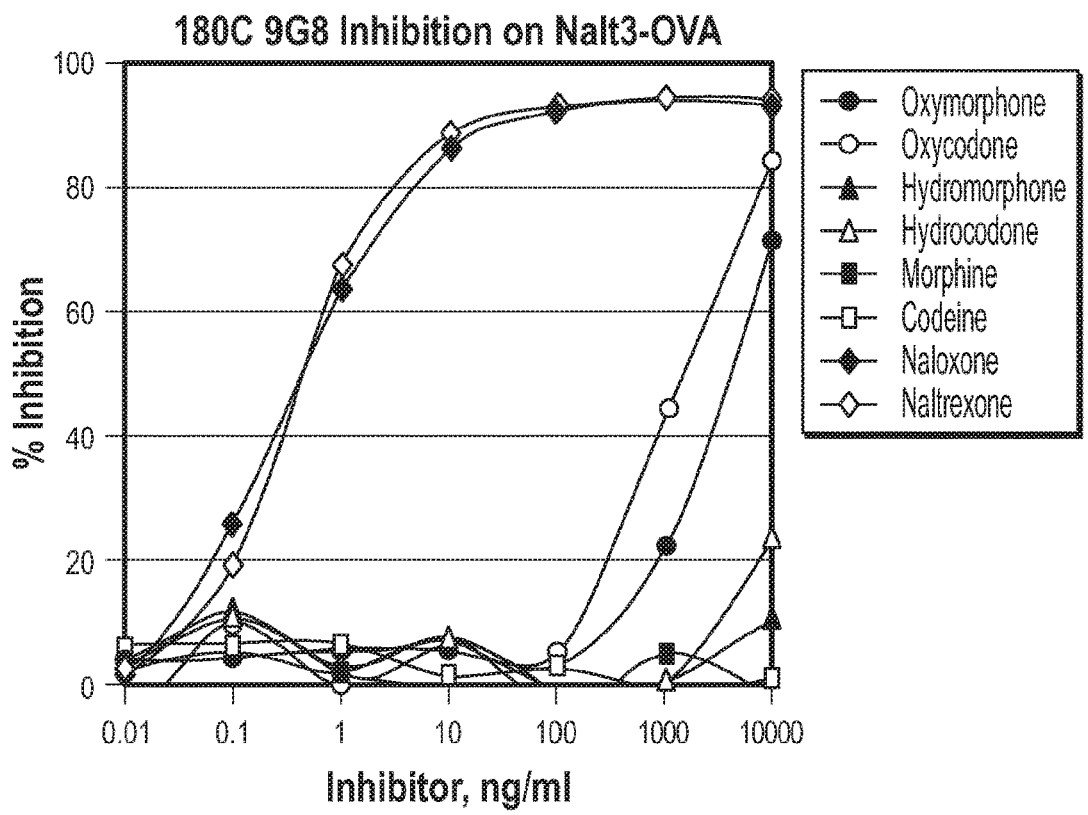
Figure 8:
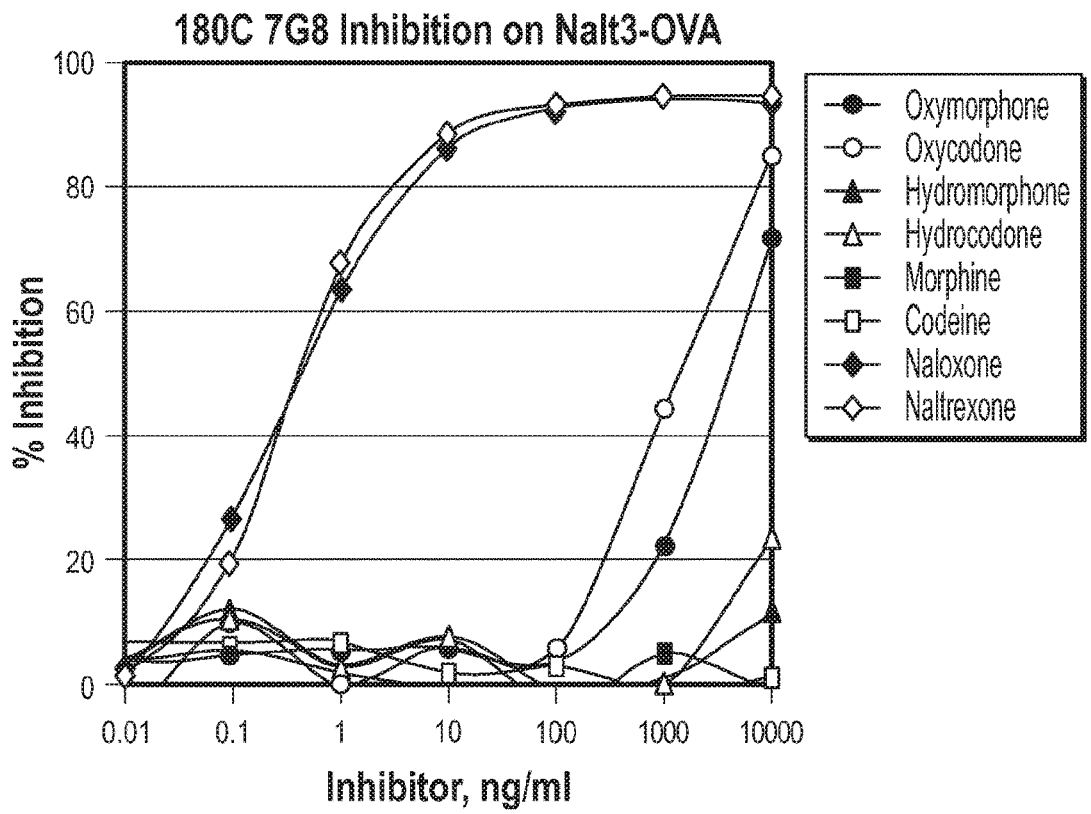
Figure 8:
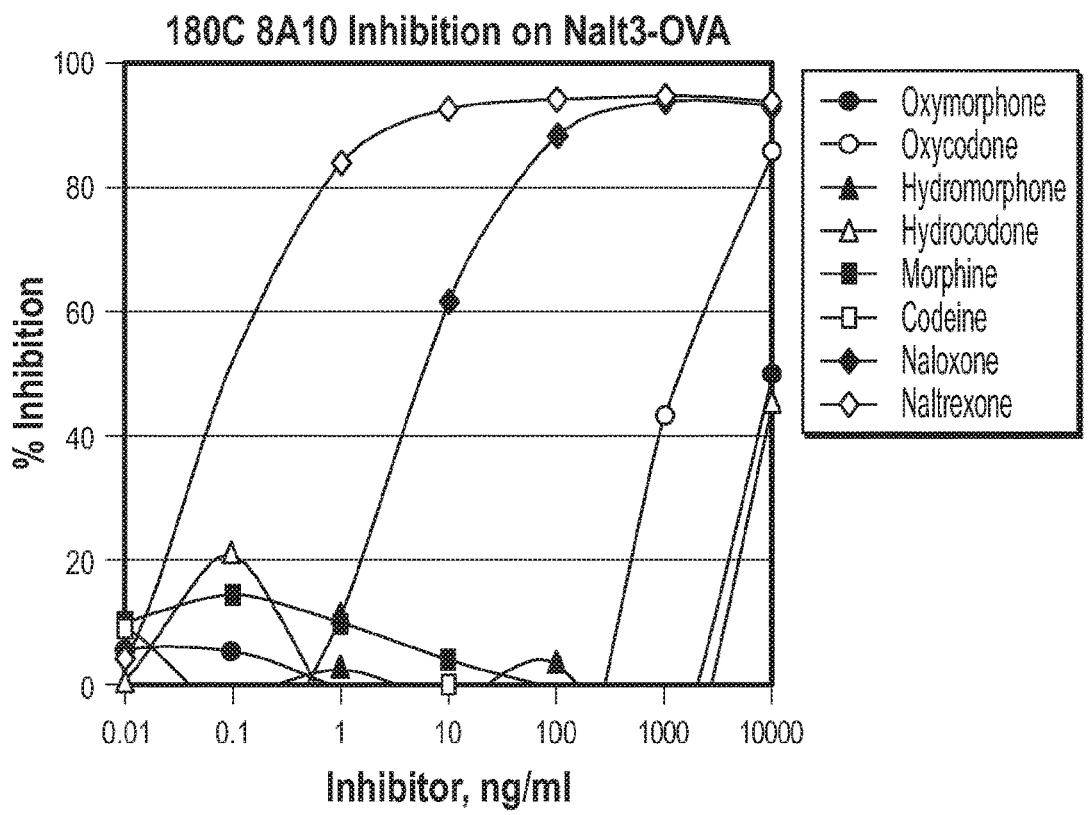
Figure 8:
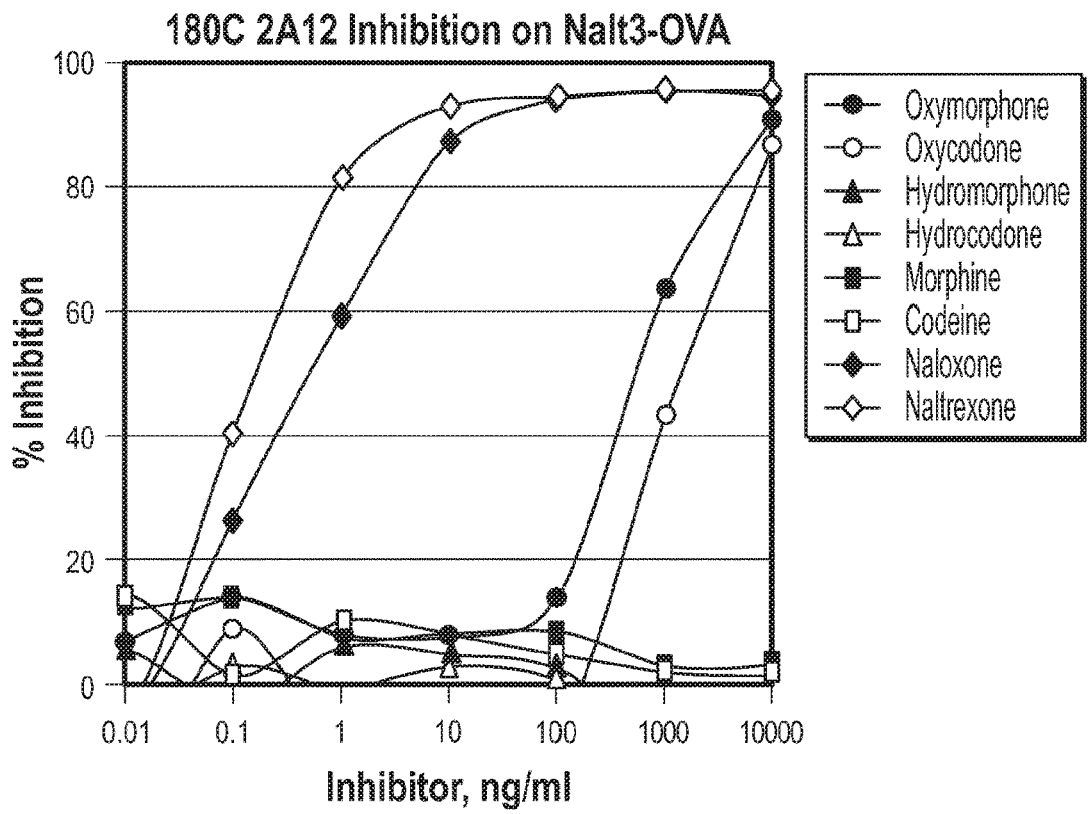
Figure 8:
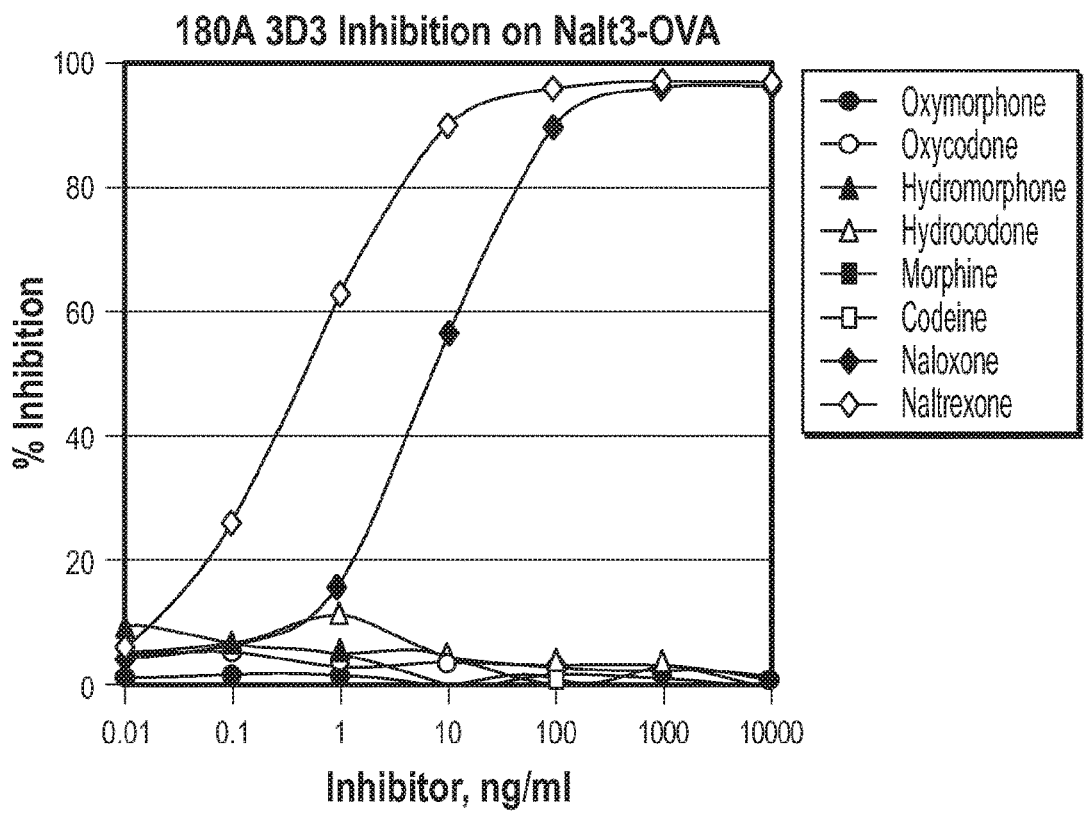
Figure 8:
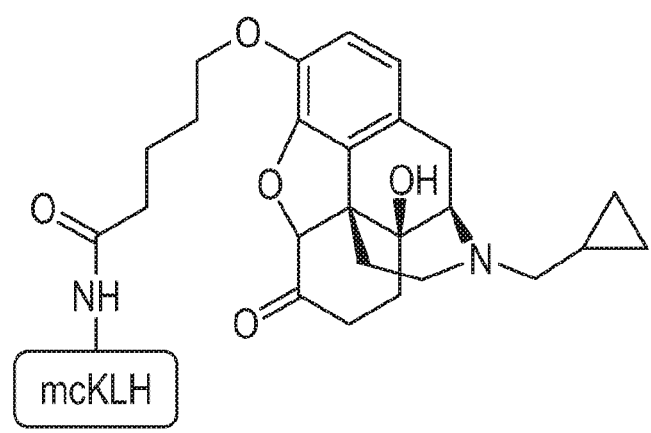

As shown in FIG. 7, monoclonal antibodies designated 179B 9G1.1, 179B 9E12, 179B 10A7, 179A 6H6, and 179B 9E7 were generated using naloxone-3-Val-mcKLH (Formula III, wherein $R_2$ is an allyl) and possessed good specificity for naloxone over the eight other key opioids tested in the inhibition ELISA assay. As shown in FIG. 8, monoclonal antibodies designated 180B 13F7, 180C 1F8, 180C 7G8, 180C 8A10, 180C 9D5, 180C 9G8, 180C 2A12, and 180A 3D3 were generated using naltrexone-3-Val-mcKLH (Formula III, wherein $R_2$ is a cyclopropyl) and possessed good specificity for naltrexone over the eight other key opioids tested in the inhibition ELISA assay. Based on these results, the monoclonal antibodies were then used in naloxone/naltrexone specific immunoassays as well as in methods of preventing or substantially reducing naloxone/naltrexone interference in other opiate assays, as described in further detail below.

Example 3: Monoclonal Antibody Sequencing

Hybridoma cells produced as in Example 2 were used to sequence the various monoclonal antibodies' heavy and light chains. The sequences of different clones were aligned, and the consensus sequences were provided. The various sequences obtained for each monoclonal antibody are shown in Tables 2-14 below.

TABLE 2

Sequence Identifiers for Various Sequences of the Anti-Naltrexone Monoclonal Antibody 180C 2A12

| Sequence | SEQ ID NO: of Amino Acid Sequence | SEQ ID NO: of DNA Sequence |
|---|---|---|
| Heavy Chain | 1 | 9 |
| Heavy Chain CDR1 | 2 | 10 |
| Heavy Chain CDR2 | 3 | 11 |
| Heavy Chain CDR3 | 4 | 12 |
| Light Chain | 5 | 13 |
| Light Chain CDR1 | 6 | 14 |
| Light Chain CDR2 | 7 | 15 |
| Light Chain CDR3 | 8 | 16 |
| Heavy Chain Variable Region | 17 | 19 |
| Light Chain Variable Region | 18 | 20 |

TABLE 3

Sequence Identifiers for Various Sequences of the Anti-Naltrexone Monoclonal Antibody 180A 3D3

| Sequence | SEQ ID NO: of Amino Acid Sequence | SEQ ID NO: of DNA Sequence |
|---|---|---|
| Heavy Chain | 21 | 29 |
| Heavy Chain CDR1 | 22 | 30 |
| Heavy Chain CDR2 | 23 | 31 |
| Heavy Chain CDR3 | 24 | 32 |
| Light Chain | 25 | 33 |
| Light Chain CDR1 | 26 | 34 |
| Light Chain CDR2 | 27 | 35 |
| Light Chain CDR3 | 28 | 36 |

TABLE 3-continued

Sequence Identifiers for Various Sequences of the
Anti-Naltrexone Monoclonal Antibody 180A 3D3

| Sequence | SEQ ID NO: of Amino Acid Sequence | SEQ ID NO: of DNA Sequence |
|---|---|---|
| Heavy Chain Variable Region | 37 | 39 |
| Light Chain Variable Region | 38 | 40 |

TABLE 4

Sequence Identifiers for Various Sequences of the
Anti-Naltrexone Monoclonal Antibody 180B13F7

| Sequence | SEQ ID NO: of Amino Acid Sequence | SEQ ID NO: of DNA Sequence |
|---|---|---|
| Heavy Chain | 41 | 49 |
| Heavy Chain CDR1 | 42 | 50 |
| Heavy Chain CDR2 | 43 | 51 |
| Heavy Chain CDR3 | 44 | 52 |
| Light Chain | 45 | 53 |
| Light Chain CDR1 | 46 | 54 |
| Light Chain CDR2 | 47 | 55 |
| Light Chain CDR3 | 48 | 56 |
| Heavy Chain Variable Region | 57 | 59 |
| Light Chain Variable Region | 58 | 60 |

TABLE 5

Sequence Identifiers for Various Sequences of the
Anti-Naltrexone Monoclonal Antibody 180C 1F8

| Sequence | SEQ ID NO: of Amino Acid Sequence | SEQ ID NO: of DNA Sequence |
|---|---|---|
| Heavy Chain | 61 | 69 |
| Heavy Chain CDR1 | 62 | 70 |
| Heavy Chain CDR2 | 63 | 71 |
| Heavy Chain CDR3 | 64 | 72 |
| Light Chain | 65 | 73 |
| Light Chain CDR1 | 66 | 74 |
| Light Chain CDR2 | 67 | 75 |
| Light Chain CDR3 | 68 | 76 |
| Heavy Chain Variable Region | 77 | 79 |
| Light Chain Variable Region | 78 | 80 |

TABLE 6

Sequence Identifiers for Various Sequences of the
Anti-Naltrexone Monoclonal Antibody 180C 7G8

| Sequence | SEQ ID NO: of Amino Acid Sequence | SEQ ID NO: of DNA Sequence |
|---|---|---|
| Heavy Chain | 81 | 89 |
| Heavy Chain CDR1 | 82 | 90 |
| Heavy Chain CDR2 | 83 | 91 |
| Heavy Chain CDR3 | 84 | 92 |
| Light Chain | 85 | 93 |
| Light Chain CDR1 | 86 | 94 |
| Light Chain CDR2 | 87 | 95 |
| Light Chain CDR3 | 88 | 96 |
| Heavy Chain Variable Region | 97 | 99 |
| Light Chain Variable Region | 98 | 100 |

TABLE 7

Sequence Identifiers for Various Sequences of the
Anti-Naltrexone Monoclonal Antibody 180C 8A10

| Sequence | SEQ ID NO: of Amino Acid Sequence | SEQ ID NO: of DNA Sequence |
|---|---|---|
| Heavy Chain | 101 | 109 |
| Heavy Chain CDR1 | 102 | 110 |
| Heavy Chain CDR2 | 103 | 111 |
| Heavy Chain CDR3 | 104 | 112 |
| Light Chain | 105 | 113 |
| Light Chain CDR1 | 106 | 114 |
| Light Chain CDR2 | 107 | 115 |
| Light Chain CDR3 | 108 | 116 |
| Heavy Chain Variable Region | 117 | 119 |
| Light Chain Variable Region | 118 | 120 |

TABLE 8

Sequence Identifiers for Various Sequences of the
Anti-Naltrexone Monoclonal Antibody 180C 9D5

| Sequence | SEQ ID NO: of Amino Acid Sequence | SEQ ID NO: of DNA Sequence |
|---|---|---|
| Heavy Chain | 121 | 129 |
| Heavy Chain CDR1 | 122 | 130 |
| Heavy Chain CDR2 | 123 | 131 |
| Heavy Chain CDR3 | 124 | 132 |
| Light Chain | 125 | 133 |
| Light Chain CDR1 | 126 | 134 |
| Light Chain CDR2 | 127 | 135 |
| Light Chain CDR3 | 128 | 136 |
| Heavy Chain Variable Region | 137 | 139 |
| Light Chain Variable Region | 138 | 140 |

TABLE 9

Sequence Identifiers for Various Sequences of the
Anti-Naltrexone Monoclonal Antibody 180C 9G8

| Sequence | SEQ ID NO: of Amino Acid Sequence | SEQ ID NO: of DNA Sequence |
|---|---|---|
| Heavy Chain | 141 | 149 |
| Heavy Chain CDR1 | 142 | 150 |
| Heavy Chain CDR2 | 143 | 151 |
| Heavy Chain CDR3 | 144 | 152 |
| Light Chain | 145 | 153 |
| Light Chain CDR1 | 146 | 154 |
| Light Chain CDR2 | 147 | 155 |
| Light Chain CDR3 | 148 | 156 |
| Heavy Chain Variable Region | 157 | 159 |
| Light Chain Variable Region | 158 | 160 |

TABLE 10

Sequence Identifiers for Various Sequences of the
Anti-Naloxone Monoclonal Antibody 179B 9G1.1

| Sequence | SEQ ID NO: of Amino Acid Sequence | SEQ ID NO: of DNA Sequence |
|---|---|---|
| Heavy Chain | 161 | 169 |
| Heavy Chain CDR1 | 162 | 170 |
| Heavy Chain CDR2 | 163 | 171 |
| Heavy Chain CDR3 | 164 | 172 |
| Light Chain | 165 | 173 |
| Light Chain CDR1 | 166 | 174 |

TABLE 10-continued

Sequence Identifiers for Various Sequences of the
Anti-Naloxone Monoclonal Antibody 179B 9G1.1

| Sequence | SEQ ID NO: of Amino Acid Sequence | SEQ ID NO: of DNA Sequence |
|---|---|---|
| Light Chain CDR2 | 167 | 175 |
| Light Chain CDR3 | 168 | 176 |
| Heavy Chain Variable Region | 177 | 179 |
| Light Chain Variable Region | 178 | 180 |

TABLE 11

Sequence Identifiers for Various Sequences of the
Anti-Naloxone Monoclonal Antibody 179B 9E12

| Sequence | SEQ ID NO: of Amino Acid Sequence | SEQ ID NO: of DNA Sequence |
|---|---|---|
| Heavy Chain | 181 | 189 |
| Heavy Chain CDR1 | 182 | 190 |
| Heavy Chain CDR2 | 183 | 191 |
| Heavy Chain CDR3 | 184 | 192 |
| Light Chain | 185 | 193 |
| Light Chain CDR1 | 186 | 194 |
| Light Chain CDR2 | 187 | 195 |
| Light Chain CDR3 | 188 | 196 |
| Heavy Chain Variable Region | 197 | 199 |
| Light Chain Variable Region | 198 | 200 |

TABLE 12

Sequence Identifiers for Various Sequences of the
Anti-Naloxone Monoclonal Antibody 179B 10A7

| Sequence | SEQ ID NO: of Amino Acid Sequence | SEQ ID NO: of DNA Sequence |
|---|---|---|
| Heavy Chain | 201 | 209 |
| Heavy Chain CDR1 | 202 | 210 |
| Heavy Chain CDR2 | 203 | 211 |
| Heavy Chain CDR3 | 204 | 212 |
| Light Chain | 205 | 213 |
| Light Chain CDR1 | 206 | 214 |
| Light Chain CDR2 | 207 | 215 |
| Light Chain CDR3 | 208 | 216 |
| Heavy Chain Variable Region | 217 | 219 |
| Light Chain Variable Region | 218 | 220 |

TABLE 13

Sequence Identifiers for Various Sequences of the
Anti-Naloxone Monoclonal Antibody 179A 6H6

| Sequence | SEQ ID NO: of Amino Acid Sequence | SEQ ID NO: of DNA Sequence |
|---|---|---|
| Heavy Chain | 221 | 229 |
| Heavy Chain CDR1 | 222 | 230 |
| Heavy Chain CDR2 | 223 | 231 |
| Heavy Chain CDR3 | 224 | 232 |
| Light Chain | 225 | 233 |
| Light Chain CDR1 | 226 | 234 |
| Light Chain CDR2 | 227 | 235 |
| Light Chain CDR3 | 228 | 236 |
| Heavy Chain Variable Region | 237 | 239 |
| Light Chain Variable Region | 238 | 240 |

TABLE 14

Sequence Identifiers for Various Sequences of the
Anti-Naloxone Monoclonal Antibody 179B 9E7

| Sequence | SEQ ID NO: of Amino Acid Sequence | SEQ ID NO: of DNA Sequence |
|---|---|---|
| Heavy Chain | 241 | 249 |
| Heavy Chain CDR1 | 242 | 250 |
| Heavy Chain CDR2 | 243 | 251 |
| Heavy Chain CDR3 | 244 | 252 |
| Light Chain | 245 | 253 |
| Light Chain CDR1 | 246 | 254 |
| Light Chain CDR2 | 247 | 255 |
| Light Chain CDR3 | 248 | 256 |
| Heavy Chain Variable Region | 257 | 259 |
| Light Chain Variable Region | 258 | 260 |

Example 4: Use of Monoclonal Antibodies in Naloxone and Naltrexone-Specific Assays In this Example, monoclonal antibodies produced in Example 2 were utilized in naloxone- and naltrexone-specific immunoassays to demonstrate the ability of these monoclonal antibodies to detect one or both drugs in a clinical immunoassay.

Figure 9:
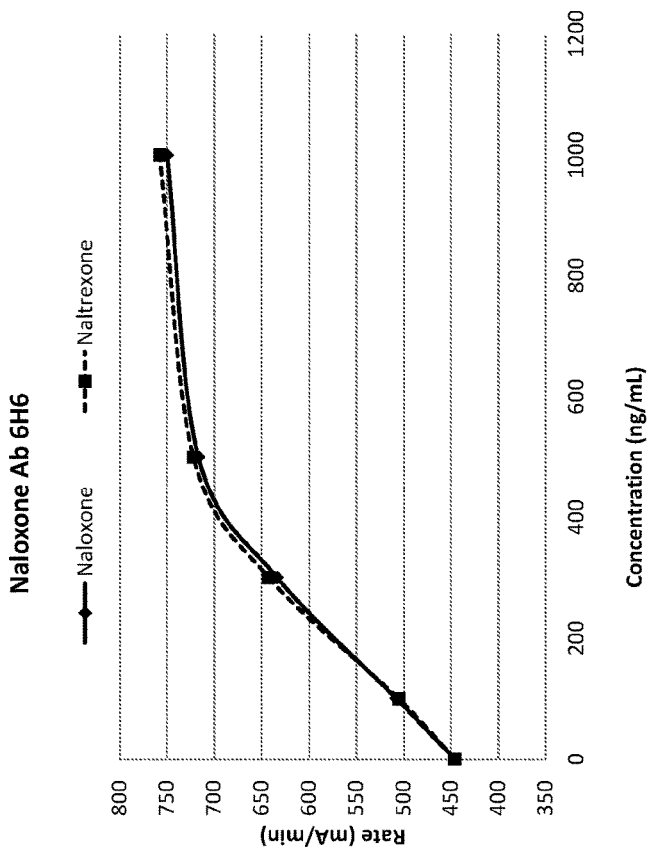
FIG. 9 graphically depicts a combination naloxone and naltrexone specific assay using the monoclonal antibody 179A 6H6 (produced using a naloxone-containing immunogen).

FIG. 9 graphically depicts naloxone and naltrexone specific assays using the anti-naloxone monoclonal antibody 179A 6H6. As can be seen, the anti-naloxone monoclonal antibody detects both naloxone and naltrexone at substantially the same specificity. Similar results were also obtained with anti-naloxone monoclonal antibodies 179B 10A7, 179B 9G1, 179B 9E12, and 179B 9E7. Therefore, these antibodies could be used in a clinical detection immunoassay for either or both drugs.

Figure 10:
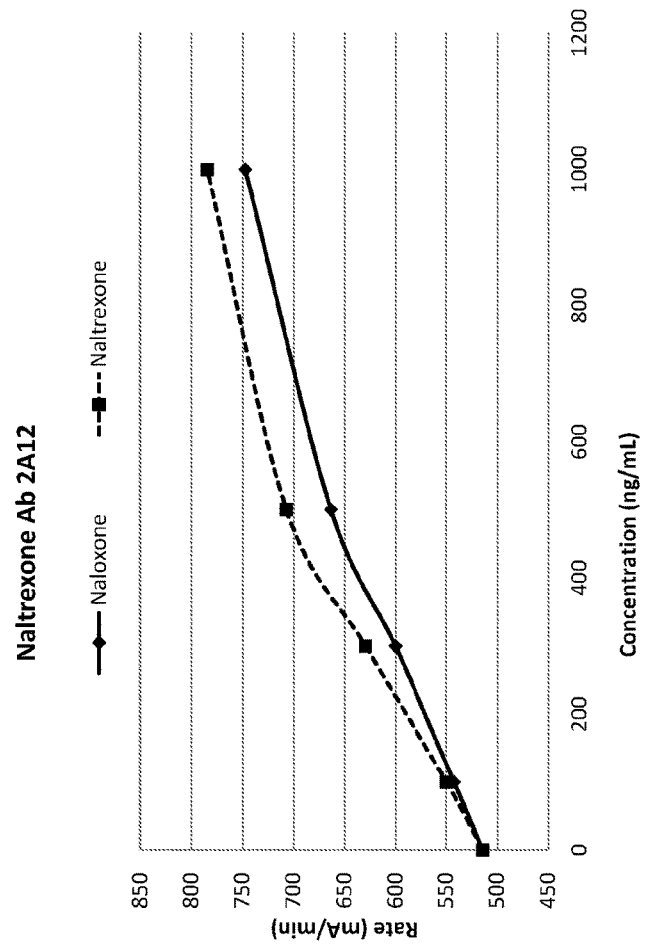
FIG. 10 graphically depicts a combination naloxone and naltrexone specific assay using the monoclonal antibody 180C 2A12 (produced using a naltrexone-containing immunogen).

FIG. 10 graphically depicts naloxone and naltrexone specific assays using the anti-naltrexone monoclonal antibody 180C 2A12. This anti-naltrexone monoclonal antibody was also capable of detecting naloxone in addition to naltrexone, albeit at a lower specificity compared to naltrexone. However, this antibody could still be used in a clinical detection immunoassay for either or both drugs.

Based on these results, these antibodies can be utilized in an assay structure as follows. An EMIT® II (enzyme multiplied immunoassay, Siemens Healthineers, Newark, DE) Plus Naloxone and/or Naltrexone Assay is a homogeneous enzyme immunoassay technique used for the analysis of specific compounds in human urine. The assay is based on competition between drug in the specimen and drug labeled with glucose-6-phosphate dehydrogenase (rG6PDH) for antibody binding sites. Enzyme activity decreases upon binding to the antibody, so the drug concentration in the specimen can be measured in terms of enzyme activity. Active enzyme converts nicotinamide adenine dinucleotide (NAD) to NADH in the presence of glucose-6-phosphate (G6P), resulting in an absorbance change that is measured spectrophotometrically. Endogenous serum G6PDH does not interfere because the coenzyme NAD functions only with the bacterial (*Leuconostoc mesenteroides*) enzyme employed in the assay.

The EMIT® assay format comprises an antibody/substrate reagent, known as reagent 1. This reagent includes the antibody as well as buffers, preservatives, and stabilizers for the assay. The EMIT® assay format also comprises an enzyme reagent, known as reagent 2. This reagent includes the conjugate as well as buffers, preservatives, and stabilizers for the assay.

Example 5: Reduction of Naloxone/Naltrexone Interference in Opioid Assays

In this Example, monoclonal antibodies produced in Example 2 were utilized in opiate enzyme multiplied immunoassays to demonstrate the ability to reduce naloxone/naltrexone interference in these assays.

FIG. 11 demonstrates that, in the presence of the naltrexone antibody blocker 3D3, the cross reactivity of naloxone and naltrexone changes from a positive to a negative response to the cutoff (300 ng/mL). Similarly, FIG. 12 demonstrates that, in the presence of the naloxone antibody blocker 6H6, the cross reactivity of naloxone changes from a positive to a negative response to the cutoff (300 ng/mL), only at a much lower concentration.

In FIG. 13, the anti-naltrexone monoclonal antibody 2A12 was used as a blocker in a hydrocodone assay to increase the amount of naloxone and naltrexone that produces a negative response to the cutoff (300 ng/ml).

Thus, in accordance with the present disclosure, there have been provided compositions and methods of producing and using same which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. An antibody or antigen-binding fragment thereof which can specifically bind to naloxone and naltrexone, wherein the antibody or antigen-binding fragment is produced by immunization of a non-human animal with an antigen of Formula III:

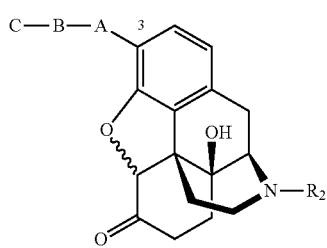

Formula III wherein, in Formula III: A is a hetero atom selected from the group consisting of —O—, —N—, or —S—; B is a functional group selected from the group consisting of —C—, a lower alkyl ($C_0$ to $C_{10}$), —CONH—, —$SO_2$—, or —$PO_4$—; C is a carrier protein; and $R_2$ is H, alkyl, allyl, or methylenecyclopropyl; and wherein the antibody or antigen-binding fragment thereof comprises:
- a heavy chain variable region CDR1 having the amino acid sequence of SEQ ID NO:2;
- a heavy chain variable region CDR2 having the amino acid sequence of SEQ ID NO:3;
- a heavy chain variable region CDR3 having the amino acid sequence of SEQ ID NO:4;
- a light chain variable region CDR1 having the amino acid sequence of SEQ ID NO:6;
- a light chain variable region CDR2 having the amino acid sequence of SEQ ID NO:7; and
- a light chain variable region CDR3 having the amino acid sequence of SEQ ID NO:8.

2. The antibody or antigen-binding fragment thereof of claim 1, further defined as a monoclonal antibody or antigen-binding fragment thereof.

3. The antibody or antigen-binding fragment thereof of claim 1, wherein a heavy chain variable region of the antibody or functional antigen-binding fragment thereof has an amino acid sequence that is at least about 90% identical to SEQ ID NO:17 and/or a light chain variable region of the antibody or antigen-binding fragment thereof has an amino acid sequence that is at least about 90% identical to SEQ ID NO:18.

4. The antibody or antigen-binding fragment thereof of claim 1, wherein the heavy and light chain variable regions of the antibody or antigen-binding fragment thereof have the amino acid sequences of SEQ ID NOS:17 and 18, respectively.

5. The antibody or antigen-binding fragment thereof of claim 1, wherein the heavy chain of the antibody or antigen-binding fragment thereof has an amino acid sequence that is at least about 90% identical to SEQ ID NO:1 and/or the light chain of the antibody or functional antigen-binding fragment thereof has an amino acid sequence that is at least about 90% identical to SEQ ID NO:5.

6. The antibody or antigen-binding fragment thereof of claim 1, wherein the heavy and light chains of the antibody or antigen-binding fragment thereof have the amino acid sequences of SEQ ID NOS:1 and 5, respectively.

7. The antibody or antigen-binding fragment thereof of claim 1, further defined as being selected from a full-length immunoglobulin molecule, an scFv, a Fab fragment, a Fab' fragment, a F(ab')2, a Fv, a disulfide linked Fv, and combinations thereof.

8. The antibody or antigen-binding fragment thereof of claim 1, further defined as a purified antibody or antigen-binding fragment thereof.

9. An antibody or antigen-binding fragment thereof which can specifically bind to naloxone and naltrexone, wherein the antibody or antigen-binding fragment comprises:
- a heavy chain variable region having an amino acid sequence that is at least 90% identical to SEQ ID NO:17; and
- a light chain variable region having an amino acid sequence that is at least 90% identical to SEQ ID NO:18.

10. The antibody or antigen-binding fragment thereof of claim 9, wherein the heavy chain variable region has the amino acid sequence of SEQ ID NO:17, and the light chain variable region has the amino acid sequence of SEQ ID NO:18.

11. The antibody or antigen-binding fragment thereof of claim 9, further defined as a monoclonal antibody or antigen-binding fragment thereof.

12. The antibody or antigen-binding fragment thereof of claim 9, further defined as being selected from a full-length immunoglobulin molecule, an scFv, a Fab fragment, a Fab' fragment, a F(ab')2, a Fv, a disulfide linked Fv, and combinations thereof.

13. The antibody or antigen-binding fragment thereof of claim 9, further defined as a purified antibody or antigen-binding fragment thereof.

14. An antibody or antigen-binding fragment thereof which can specifically bind to naloxone and naltrexone, wherein the antibody or antigen-binding fragment comprises:
- a heavy chain having an amino acid sequence that is at least 90% identical to SEQ ID NO:1; and
- a light chain having an amino acid sequence that is at least 90% identical to SEQ ID NO:5.

15. The antibody or antigen-binding fragment thereof of claim 14, wherein the heavy chain has the amino acid sequence of SEQ ID NO:1, and the light chain has the amino acid sequence of SEQ ID NO:5.

16. The antibody or antigen-binding fragment thereof of claim 14, further defined as a monoclonal antibody or antigen-binding fragment thereof.

17. The antibody or antigen-binding fragment thereof of claim 14, further defined as being selected from a full-length immunoglobulin molecule, an scFv, a Fab fragment, a Fab' fragment, a F(ab')2, a Fv, a disulfide linked Fv, and combinations thereof.

18. The antibody or antigen-binding fragment thereof of claim 14, further defined as a purified antibody or antigen-binding fragment thereof.

* * * * *

UNITED STATES PATENT AND TRADEMARK OFFICE
CERTIFICATE OF CORRECTION

| | | |
|---|---|---|
| PATENT NO. | : 12,404,346 B2 | Page 1 of 1 |
| APPLICATION NO. | : 17/310042 | |
| DATED | : September 2, 2025 | |
| INVENTOR(S) | : Manoj Sharma et al. | |

It is certified that error appears in the above-identified patent and that said Letters Patent is hereby corrected as shown below:

In the Claims

In Column 189, Line 62, in Claim 3, delete the word "functional";

In Column 190, Line 26, in Claim 5, delete the word "functional".

Signed and Sealed this
Eighteenth Day of November, 2025

John A. Squires
*Director of the United States Patent and Trademark Office*

```
                        SEQUENCE LISTING

<160> NUMBER OF SEQ ID NOS: 260

<210> SEQ ID NO 1
<211> LENGTH: 460
<212> TYPE: PRT
<213> ORGANISM: Artificial sequence
<220> FEATURE:
<223> OTHER INFORMATION: Amino Acid sequence of heavy chain of
      monoclonal antibody SHC 004

<400> SEQUENCE: 1

Met Gly Trp Ser Trp Ile Phe Leu Phe Leu Leu Ser Gly Thr Ala Gly
1               5                   10                  15

Val His Cys Gln Val Gln Leu Gln Gln Ser Gly Pro Glu Leu Val Lys
            20                  25                  30

Pro Gly Gly Ser Val Lys Leu Ser Cys Lys Ala Ser Gly Tyr Ile Phe
        35                  40                  45

Asn Asp Tyr Thr Ile His Trp Met Lys Gln Ser Pro Gly Gln Gly Leu
    50                  55                  60

Glu Trp Ile Gly Trp Met Asn Arg Arg Ser Phe Asn Thr Met Tyr Asn
65                  70                  75                  80

Asp Lys Phe Lys Gly Lys Ala Thr Met Thr Val Asp Lys Ser Ser Ser
                85                  90                  95

Thr Ala Tyr Ile Gln Leu Ser Ser Leu Thr Ser Asp Asp Ser Ala Val
            100                 105                 110

Tyr Phe Cys Val Arg Asp Val Tyr Asp Asn Leu Asp Tyr Trp Gly Gln
        115                 120                 125

Gly Thr Ser Val Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Glu Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240
```

```
Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
    290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365

Glu Gln Met Ala Lys Asp Lys Val Ser Leu Thr Cys Met Ile Thr Asp
    370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Ile Tyr Ser Lys Leu Asn Val Gln Lys Ser Asn Trp Glu Ala
            420                 425                 430

Gly Asn Thr Phe Thr Cys Ser Val Leu His Glu Gly Leu His Asn His
        435                 440                 445

His Thr Glu Lys Ser Leu Ser His Ser Pro Gly Lys
    450                 455                 460

<210> SEQ ID NO 2
<211> LENGTH: 5
<212> TYPE: PRT
<213> ORGANISM: Artificial sequence
<220> FEATURE:
<223> OTHER INFORMATION: Amino acid sequence of Heavy Chain CDR1 of
      monoclonal antibody SHC 004

<400> SEQUENCE: 2

Asp Tyr Thr Ile His
1               5

<210> SEQ ID NO 3
<211> LENGTH: 17
<212> TYPE: PRT
<213> ORGANISM: Artificial sequence
<220> FEATURE:
<223> OTHER INFORMATION: Amino acid sequence of Heavy Chain CDR2 of
      monoclonal antibody SHC 004

<400> SEQUENCE: 3

Trp Met Asn Arg Arg Ser Phe Asn Thr Met Tyr Asn Asp Lys Phe Lys
1               5                   10                  15

Gly

<210> SEQ ID NO 4
<211> LENGTH: 8
<212> TYPE: PRT
<213> ORGANISM: Artificial sequence
<220> FEATURE:
```

<223> OTHER INFORMATION: Amino acid sequence of Heavy Chain CDR3 of
      monoclonal antibody SHC 004

<400> SEQUENCE: 4

Asp Val Tyr Asp Asn Leu Asp Tyr
1               5

<210> SEQ ID NO 5
<211> LENGTH: 238
<212> TYPE: PRT
<213> ORGANISM: Artificial sequence
<220> FEATURE:
<223> OTHER INFORMATION: Amino acid sequence of Light Chain of
      monoclonal antibody SHC 004

<400> SEQUENCE: 5

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
                20                  25                  30

Ser Leu Gly Asp Gln Ala Ser Ile Ser Cys Arg Ser Ser Gln Ser Ile
            35                  40                  45

Val His Ser Asn Gly Asn Thr Tyr Leu Glu Trp Tyr Leu Gln Lys Pro
    50                  55                  60

Gly Gln Ser Pro Arg Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Arg Ile Ser Arg Val Glu Ala Glu Asp Leu Gly Leu Tyr Tyr Cys
            100                 105                 110

Phe Gln Gly Ser His Val Pro Leu Thr Phe Gly Ala Gly Thr Lys Leu
        115                 120                 125

Glu Leu Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Arg Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 6
<211> LENGTH: 16
<212> TYPE: PRT
<213> ORGANISM: Artificial sequence
<220> FEATURE:
<223> OTHER INFORMATION: Amino acid sequence of Light Chain CDR1 of
      monoclonal antibody SHC 004

<400> SEQUENCE: 6

Arg Ser Ser Gln Ser Ile Val His Ser Asn Gly Asn Thr Tyr Leu Glu
1               5                   10                  15

<210> SEQ ID NO 7
<211> LENGTH: 7
<212> TYPE: PRT
<213> ORGANISM: Artificial sequence
<220> FEATURE:
<223> OTHER INFORMATION: Amino acid sequence of Light Chain CDR2 of
      monoclonal antibody SHC 004

<400> SEQUENCE: 7

Lys Val Ser Asn Arg Phe Ser
1               5

<210> SEQ ID NO 8
<211> LENGTH: 9
<212> TYPE: PRT
<213> ORGANISM: Artificial sequence
<220> FEATURE:
<223> OTHER INFORMATION: Amino acid sequence of Light Chain CDR3 of
      monoclonal antibody SHC 004

<400> SEQUENCE: 8

Phe Gln Gly Ser His Val Pro Leu Thr
1               5

<210> SEQ ID NO 9
<211> LENGTH: 1383
<212> TYPE: PRT
<213> ORGANISM: Artificial sequence
<220> FEATURE:
<223> OTHER INFORMATION: DNA sequence of Heavy Chain of monoclonal
      antibody SHC 004

<400> SEQUENCE: 9

Ala Thr Gly Gly Gly Thr Gly Gly Ala Gly Cys Thr Gly Gly Ala
1               5                   10                  15

Thr Cys Thr Thr Thr Cys Thr Cys Thr Thr Cys Cys Thr Cys Cys Thr
                20                  25                  30

Gly Thr Cys Ala Gly Gly Ala Ala Cys Thr Gly Cys Ala Gly Gly Thr
            35                  40                  45

Gly Thr Cys Cys Ala Thr Thr Gly Cys Ala Gly Gly Thr Cys Cys
         50                  55                  60

Ala Gly Cys Thr Gly Cys Ala Gly Cys Ala Gly Thr Cys Thr Gly Gly
65                  70                  75                  80

Ala Cys Cys Thr Gly Ala Gly Cys Thr Gly Gly Thr Gly Ala Ala Gly
                85                  90                  95

Cys Cys Thr Gly Gly Ala Gly Gly Thr Thr Cys Ala Gly Thr Gly Ala
            100                 105                 110

Ala Gly Cys Thr Gly Thr Cys Cys Thr Gly Cys Ala Ala Gly Gly Cys
        115                 120                 125

Thr Thr Cys Thr Gly Gly Cys Thr Ala Cys Ala Cys Thr Thr Cys
        130                 135                 140

Ala Ala Thr Gly Ala Cys Thr Ala Thr Ala Cys Thr Ala Thr Ala Cys
145                 150                 155                 160

Ala Cys Thr Gly Gly Ala Thr Gly Ala Ala Gly Cys Ala Gly Ala Gly
                165                 170                 175

Thr Cys Cys Thr Gly Gly Ala Cys Ala Gly Gly Gly Ala Cys Thr Thr
            180                 185                 190

Gly Ala Gly Thr Gly Gly Ala Thr Thr Gly Gly Ala Thr Gly Gly Ala
        195                 200                 205

Thr Gly Ala Ala Thr Cys Gly Thr Ala Gly Ala Ala Gly Thr Thr
        210                 215                 220

-continued

```
Thr Ala Ala Cys Ala Cys Cys Ala Thr Gly Thr Ala Cys Ala Ala Thr
225                 230                 235                 240

Gly Ala Cys Ala Ala Gly Thr Thr Cys Ala Ala Gly Gly Gly Cys Ala
                245                 250                 255

Ala Gly Gly Cys Cys Ala Cys Ala Ala Thr Gly Ala Cys Thr Gly Thr
            260                 265                 270

Ala Gly Ala Cys Ala Ala Ala Thr Cys Cys Thr Cys Cys Ala Gly Cys
        275                 280                 285

Ala Cys Ala Gly Cys Cys Thr Ala Cys Ala Thr Thr Cys Ala Ala Cys
    290                 295                 300

Thr Cys Ala Gly Cys Ala Gly Cys Cys Thr Gly Ala Cys Cys Thr Cys
305                 310                 315                 320

Thr Gly Ala Cys Gly Ala Cys Thr Cys Thr Gly Cys Gly Gly Thr Cys
                325                 330                 335

Thr Ala Thr Thr Thr Cys Thr Gly Thr Gly Thr Ala Ala Gly Ala Gly
            340                 345                 350

Ala Thr Gly Thr Thr Thr Ala Thr Gly Ala Thr Ala Ala Thr Cys Thr
        355                 360                 365

Gly Gly Ala Cys Thr Ala Cys Thr Gly Gly Gly Gly Thr Cys Ala Ala
    370                 375                 380

Gly Gly Ala Ala Cys Cys Thr Cys Ala Gly Thr Cys Ala Cys Cys Gly
385                 390                 395                 400

Thr Cys Thr Cys Cys Thr Cys Ala Gly Cys Cys Ala Ala Ala Ala Cys
                405                 410                 415

Gly Ala Cys Ala Cys Cys Cys Cys Cys Ala Thr Cys Thr Gly Thr Cys
            420                 425                 430

Thr Ala Thr Cys Cys Ala Cys Thr Gly Gly Cys Cys Cys Cys Thr Gly
        435                 440                 445

Gly Ala Thr Cys Thr Gly Cys Thr Gly Cys Cys Cys Ala Ala Ala Cys
    450                 455                 460

Thr Ala Ala Cys Thr Cys Cys Ala Thr Gly Gly Thr Gly Ala Cys Cys
465                 470                 475                 480

Cys Thr Gly Gly Gly Ala Thr Gly Cys Cys Thr Gly Gly Thr Cys Ala
                485                 490                 495

Ala Gly Gly Gly Cys Thr Ala Thr Thr Thr Cys Cys Cys Thr Gly Ala
            500                 505                 510

Gly Cys Cys Ala Gly Thr Gly Ala Cys Ala Gly Thr Gly Ala Cys Cys
        515                 520                 525

Thr Gly Gly Ala Ala Cys Thr Cys Thr Gly Gly Ala Thr Cys Cys Cys
    530                 535                 540

Thr Gly Thr Cys Cys Ala Gly Cys Gly Gly Thr Gly Thr Gly Cys Ala
545                 550                 555                 560

Cys Ala Cys Cys Thr Thr Cys Cys Cys Ala Gly Cys Thr Gly Thr Cys
                565                 570                 575

Cys Thr Gly Cys Ala Gly Thr Cys Thr Gly Ala Cys Cys Thr Cys Thr
            580                 585                 590

Ala Cys Ala Cys Thr Cys Thr Gly Ala Gly Cys Ala Gly Cys Thr Cys
        595                 600                 605

Ala Gly Thr Gly Ala Cys Thr Gly Thr Cys Cys Cys Cys Thr Cys Cys
    610                 615                 620

Ala Gly Cys Ala Cys Cys Thr Gly Gly Cys Cys Cys Ala Gly Cys Gly
625                 630                 635                 640
```

-continued

Ala Gly Ala Cys Cys Gly Thr Cys Ala Cys Thr Gly Cys Ala Ala
                    645                 650                 655

Cys Gly Thr Thr Gly Cys Cys Ala Cys Cys Cys Gly Gly Cys Cys
                660                 665                 670

Ala Gly Cys Ala Gly Cys Ala Cys Ala Ala Gly Gly Thr Gly Gly
            675                 680                 685

Ala Cys Ala Ala Gly Ala Ala Ala Thr Thr Gly Thr Gly Cys Cys
        690                 695                 700

Cys Ala Gly Gly Gly Ala Thr Thr Gly Thr Gly Thr Thr Gly Thr
705                 710                 715                 720

Ala Ala Gly Cys Cys Thr Thr Gly Cys Ala Thr Ala Thr Gly Thr Ala
                    725                 730                 735

Cys Ala Gly Thr Cys Cys Ala Gly Ala Ala Gly Thr Ala Thr Cys
                740                 745                 750

Ala Thr Cys Thr Gly Thr Cys Thr Thr Cys Ala Thr Cys Thr Thr Cys
            755                 760                 765

Cys Cys Cys Cys Ala Ala Ala Gly Cys Cys Ala Ala Gly Gly
        770                 775                 780

Ala Thr Gly Thr Gly Cys Thr Cys Ala Cys Cys Ala Thr Thr Cys
785                 790                 795                 800

Thr Cys Thr Gly Ala Cys Thr Cys Cys Thr Ala Ala Gly Gly Thr Cys
                    805                 810                 815

Ala Cys Gly Thr Gly Thr Gly Thr Gly Thr Gly Thr Ala Gly
                820                 825                 830

Ala Cys Ala Thr Cys Ala Gly Cys Ala Ala Gly Gly Ala Thr Gly Ala
            835                 840                 845

Thr Cys Cys Cys Gly Ala Gly Gly Thr Cys Cys Ala Gly Thr Thr Cys
        850                 855                 860

Ala Gly Cys Thr Gly Gly Thr Thr Thr Gly Thr Ala Gly Ala Thr Gly
865                 870                 875                 880

Ala Thr Gly Thr Gly Gly Ala Gly Gly Thr Gly Cys Ala Cys Ala Cys
                    885                 890                 895

Ala Gly Cys Thr Cys Ala Gly Ala Cys Gly Cys Ala Ala Cys Cys Cys
                900                 905                 910

Cys Gly Gly Gly Ala Gly Gly Ala Gly Cys Ala Gly Thr Thr Cys Ala
            915                 920                 925

Ala Cys Ala Gly Cys Ala Cys Thr Thr Cys Cys Gly Cys Thr Cys
        930                 935                 940

Ala Gly Thr Cys Ala Gly Thr Gly Ala Ala Cys Thr Thr Cys Cys
945                 950                 955                 960

Ala Thr Cys Ala Thr Gly Cys Ala Cys Cys Ala Gly Gly Ala Cys Thr
                    965                 970                 975

Gly Gly Cys Thr Cys Ala Ala Thr Gly Gly Cys Ala Ala Gly Gly Ala
                980                 985                 990

Gly Thr Thr Cys Ala Ala Ala Thr  Gly Cys Ala Gly Gly  Gly Thr Cys
            995                 1000                 1005

Ala Ala  Cys Ala Gly Thr Gly  Cys Ala Gly Cys Thr  Thr Thr Cys
    1010                 1015                 1020

Cys Cys  Thr Gly Cys Cys Cys  Cys Cys Ala Thr Cys  Gly Ala Gly
    1025                 1030                 1035

Ala Ala  Ala Ala Cys Cys Ala  Thr Cys Thr Cys Cys  Ala Ala Ala
    1040                 1045                 1050

```
Ala Cys Cys Ala Ala Ala Gly Gly Cys Ala Gly Ala Cys Cys Gly
1055                1060                1065

Ala Ala Gly Gly Cys Thr Cys Cys Ala Cys Ala Gly Gly Thr Gly
1070                1075                1080

Thr Ala Cys Ala Cys Cys Ala Thr Thr Cys Cys Ala Cys Cys Thr
1085                1090                1095

Cys Cys Cys Ala Ala Gly Gly Ala Gly Cys Ala Gly Ala Thr Gly
1100                1105                1110

Gly Cys Cys Ala Ala Gly Gly Ala Thr Ala Ala Gly Thr Cys
1115                1120                1125

Ala Gly Thr Cys Thr Gly Ala Cys Cys Thr Gly Cys Ala Thr Gly
1130                1135                1140

Ala Thr Ala Ala Cys Ala Gly Ala Cys Thr Thr Cys Thr Thr Cys
1145                1150                1155

Cys Cys Thr Gly Ala Ala Gly Ala Cys Ala Thr Thr Ala Cys Thr
1160                1165                1170

Gly Thr Gly Gly Ala Gly Thr Gly Gly Cys Ala Gly Thr Gly Gly
1175                1180                1185

Ala Ala Thr Gly Gly Gly Cys Ala Gly Cys Cys Ala Gly Cys Gly
1190                1195                1200

Gly Ala Gly Ala Ala Cys Thr Ala Cys Ala Ala Gly Ala Ala Cys
1205                1210                1215

Ala Cys Thr Cys Ala Gly Cys Cys Cys Ala Thr Cys Ala Thr Gly
1220                1225                1230

Gly Ala Cys Ala Cys Ala Gly Ala Thr Gly Gly Cys Thr Cys Thr
1235                1240                1245

Thr Ala Cys Thr Thr Cys Ala Thr Cys Thr Ala Cys Ala Gly Cys
1250                1255                1260

Ala Ala Gly Cys Thr Cys Ala Ala Thr Gly Thr Gly Cys Ala Gly
1265                1270                1275

Ala Ala Gly Ala Gly Cys Ala Ala Cys Thr Gly Gly Gly Ala Gly
1280                1285                1290

Gly Cys Ala Gly Gly Ala Ala Ala Thr Ala Cys Thr Thr Thr Cys
1295                1300                1305

Ala Cys Cys Thr Gly Cys Thr Cys Thr Gly Thr Gly Thr Thr Ala
1310                1315                1320

Cys Ala Thr Gly Ala Gly Gly Gly Cys Cys Thr Gly Cys Ala Cys
1325                1330                1335

Ala Ala Cys Cys Ala Cys Cys Ala Thr Ala Cys Thr Gly Ala Gly
1340                1345                1350

Ala Ala Gly Ala Gly Cys Cys Thr Cys Thr Cys Cys Cys Ala Cys
1355                1360                1365

Thr Cys Thr Cys Cys Thr Gly Gly Thr Ala Ala Ala Thr Gly Ala
1370                1375                1380
```

<210> SEQ ID NO 10
<211> LENGTH: 15
<212> TYPE: DNA
<213> ORGANISM: Artificial sequence
<220> FEATURE:
<223> OTHER INFORMATION: DNA sequence of Heavy Chain CDR1 of monoclonal antibody SHC 004

<400> SEQUENCE: 10
gactatacta tacac                                                    15

<210> SEQ ID NO 11
<211> LENGTH: 51
<212> TYPE: DNA
<213> ORGANISM: Artificial sequence
<220> FEATURE:
<223> OTHER INFORMATION: DNA sequence of Heavy Chain CDR2 of monoclonal
      antibody SHC 004

<400> SEQUENCE: 11
tggatgaatc gtagaagttt taacaccatg tacaatgaca agttcaaggg c        51

<210> SEQ ID NO 12
<211> LENGTH: 24
<212> TYPE: DNA
<213> ORGANISM: Artificial sequence
<220> FEATURE:
<223> OTHER INFORMATION: DNA sequence of Heavy Chain CDR3 of monoclonal
      antibody SHC 004

<400> SEQUENCE: 12
gatgtttatg ataatctgga ctac                                       24

<210> SEQ ID NO 13
<211> LENGTH: 717
<212> TYPE: DNA
<213> ORGANISM: Artificial sequence
<220> FEATURE:
<223> OTHER INFORMATION: DNA sequence of Light Chain of monoclonal
      antibody SHC 004

<400> SEQUENCE: 13
atgaagttgc ctgttaggct gttggtgctg atgttctgga ttcctgcttc cagcagtgat    60
gttttgatga cccaaactcc actctccctg cctgtcagtc ttggagatca agcctccatc   120
tcttgcagat ccagtcagag tattgtacat agtaatggaa acacctattt agagtggtac   180
ctgcagaaac aggccagtc tccaaggctc ctgatctaca agtttccaa ccgattttct     240 ggggtcccag acaggttcag tggcagtgga tccgggacag atttcacact caggatcagt   300
agagtggagg ctgaggatct gggactttat tactgctttc aaggttcaca cgttcctctc   360
acgttcggtg ctgggaccaa gctggagctg aaacggctg atgctgcacc aactgtatcc    420
atcttcccac catccagtga gcagttaaca tctggaggtg cctcagtcgt gtgcttcttg   480
aacaacttct accccagaga catcaatgtc aagtggaaga ttgatggcag tgaacgacaa   540
aatggtgtcc tgaacagttg gactgatcag gacagcaaag acagcaccta cagcatgagc   600
agcaccctca cattgaccaa ggacgagtat gaacgacata cagctatac ctgtgaggcc    660 actcacaaga catcaacttc acccatcgtc aagagcttca acaggaatga gtgttag     717

<210> SEQ ID NO 14
<211> LENGTH: 48
<212> TYPE: DNA
<213> ORGANISM: Artificial sequence
<220> FEATURE:
<223> OTHER INFORMATION: DNA sequence of Light Chain CDR1 of monoclonal
      antibody SHC 004

<400> SEQUENCE: 14
agatccagtc agagtattgt acatagtaat ggaaacacct atttagag              48

<210> SEQ ID NO 15
<211> LENGTH: 21
<212> TYPE: DNA

```
<213> ORGANISM: Artificial sequence
<220> FEATURE:
<223> OTHER INFORMATION: DNA sequence of Light Chain CDR2 of monoclonal
      antibody SHC 004

<400> SEQUENCE: 15
aaagtttcca accgattttc t                                              21

<210> SEQ ID NO 16
<211> LENGTH: 27
<212> TYPE: DNA
<213> ORGANISM: Artificial sequence
<220> FEATURE:
<223> OTHER INFORMATION: DNA sequence of Light Chain CDR3 of monoclonal
      antibody SHC 004

<400> SEQUENCE: 16
tttcaaggtt cacacgttcc tctcacg                                        27

<210> SEQ ID NO 17
<211> LENGTH: 117
<212> TYPE: PRT
<213> ORGANISM: Artificial sequence
<220> FEATURE:
<223> OTHER INFORMATION: Amino acid sequence of Heavy Chain variable
      region of monoclonal antibody SHC 004

<400> SEQUENCE: 17
```

Gln Val Gln Leu Gln Gln Ser Gly Pro Glu Leu Val Lys Pro Gly Gly
1               5                   10                  15

Ser Val Lys Leu Ser Cys Lys Ala Ser Gly Tyr Ile Phe Asn Asp Tyr
            20                  25                  30

Thr Ile His Trp Met Lys Gln Ser Pro Gly Gln Gly Leu Glu Trp Ile
        35                  40                  45

Gly Trp Met Asn Arg Arg Ser Phe Asn Thr Met Tyr Asn Asp Lys Phe
    50                  55                  60

Lys Gly Lys Ala Thr Met Thr Val Asp Lys Ser Ser Thr Ala Tyr
65                  70                  75                  80

Ile Gln Leu Ser Ser Leu Thr Ser Asp Asp Ser Ala Val Tyr Phe Cys
                85                  90                  95

Val Arg Asp Val Tyr Asp Asn Leu Asp Tyr Trp Gly Gln Gly Thr Ser
            100                 105                 110

Val Thr Val Ser Ser
        115

```
<210> SEQ ID NO 18
<211> LENGTH: 112
<212> TYPE: PRT
<213> ORGANISM: Artificial sequence
<220> FEATURE:
<223> OTHER INFORMATION: Amino acid sequence of Light Chain variable
      region of monoclonal antibody SHC 004

<400> SEQUENCE: 18
```

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Leu Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 19
<211> LENGTH: 351
<212> TYPE: DNA
<213> ORGANISM: Artificial sequence
<220> FEATURE:
<223> OTHER INFORMATION: DNA sequence of Heavy Chain variable region of
      monoclonal antibody SHC 004

<400> SEQUENCE: 19
caggtccagc tgcagcagtc tggacctgag ctggtgaagc ctggaggttc agtgaagctg      60
tcctgcaagg cttctggcta catcttcaat gactatacta tacactggat gaagcagagt    120
cctggacagg gacttgagtg gattggatgg atgaatcgta gaagttttaa caccatgtac    180
aatgacaagt tcaagggcaa ggccacaatg actgtagaca atcctccag cacagcctac    240 attcaactca gcagcctgac ctctgacgac tctgcggtct atttctgtgt aagagatgtt    300
tatgataatc tggactactg gggtcaagga acctcagtca ccgtctcctc a             351

<210> SEQ ID NO 20
<211> LENGTH: 336
<212> TYPE: DNA
<213> ORGANISM: Artificial sequence
<220> FEATURE:
<223> OTHER INFORMATION: DNA sequence of Light Chain variable region of
      monoclonal antibody SHC 004

<400> SEQUENCE: 20
gatgttttga tgacccaaac tccactctcc ctgcctgtca gtcttggaga tcaagcctcc      60
atctcttgca gatccagtca gagtattgta catagtaatg gaaacaccta tttagagtgg    120
tacctgcaga aaccaggcca gtctccaagg ctcctgatct acaaagtttc caaccgattt    180
tctggggtcc cagacaggtt cagtggcagt ggatccggga cagatttcac actcaggatc    240
agtagagtgg aggctgagga tctgggactt tattactgct ttcaaggttc acacgttcct    300
ctcacgttcg gtgctgggac caagctggag ctgaaa                               336

<210> SEQ ID NO 21
<211> LENGTH: 137
<212> TYPE: PRT
<213> ORGANISM: Artificial sequence
<220> FEATURE:
<223> OTHER INFORMATION: Amino Acid sequence of heavy chain of
      monoclonal antibody 180A 3D3

<400> SEQUENCE: 21

Met Tyr Leu Gly Leu Asn Cys Val Phe Ile Val Phe Leu Leu Lys Gly
1               5                   10                  15

Val Gln Ser Glu Val Asn Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Arg Gly Leu
    50                  55                  60

Glu Trp Val Ala Glu Ile Ser Leu Lys Ser Tyr Asn Tyr Ala Thr His
65                  70                  75                  80

Tyr Ala Glu Ser Val Lys Gly Arg Phe Thr Ile Ser Gly Asp Glu Ser
                85                  90                  95

Lys Asn Ser Val Tyr Leu Gln Met Asn Asn Leu Arg Ala Glu Asp Thr
            100                 105                 110

Gly Ile Tyr Phe Cys Thr Arg Gly Asp Ser Tyr Ala Leu Asp Tyr Gly
        115                 120                 125

Gln Arg Thr Leu Val Thr Val Ser Ser
    130                 135

<210> SEQ ID NO 22
<211> LENGTH: 5
<212> TYPE: PRT
<213> ORGANISM: Artificial Sequence
<220> FEATURE:
<223> OTHER INFORMATION: Amino Acid sequence of heavy chain CDR1 of
      monoclonal antibody 180A 3D3

<400> SEQUENCE: 22

Asn Tyr Trp Met Asn
1               5

<210> SEQ ID NO 23
<211> LENGTH: 19
<212> TYPE: PRT
<213> ORGANISM: Artificial Sequence
<220> FEATURE:
<223> OTHER INFORMATION: Amino Acid sequence of heavy chain CDR2 of
      monoclonal antibody 180A 3D3

<400> SEQUENCE: 23

Glu Ile Ser Leu Lys Ser Tyr Asn Tyr Ala Thr His Tyr Ala Glu Ser
1               5                   10                  15

Val Lys Gly

<210> SEQ ID NO 24
<211> LENGTH: 8
<212> TYPE: PRT
<213> ORGANISM: Artificial sequence
<220> FEATURE:
<223> OTHER INFORMATION: Amino Acid sequence of heavy chain CDR3 of
      monoclonal antibody 180A 3D3

<400> SEQUENCE: 24

Gly Asp Ser Tyr Ala Leu Asp Tyr
1               5

<210> SEQ ID NO 25
<211> LENGTH: 132
<212> TYPE: PRT
<213> ORGANISM: Artificial Sequence
<220> FEATURE:
<223> OTHER INFORMATION: Amino Acid sequence of light chain of
      monoclonal antibody 180A 3D3

<400> SEQUENCE: 25

Met Glu Phe Gln Thr Gln Val Leu Met Ser Leu Leu Leu Cys Met Ser
1               5                   10                  15

Gly Ala Cys Ala Asp Ile Val Met Thr Gln Ser Pro Thr Phe Leu Ala
                20                  25                  30

Val Thr Val Ser Lys Lys Val Thr Ile Ser Cys Thr Ala Ser Glu Ser
            35                  40                  45

```
Leu Tyr Ser Ser Lys His Lys Val His Tyr Leu Ala Trp Tyr Gln Lys
        50                  55                  60

Lys Pro Glu Gln Ser Pro Lys Leu Leu Ile Tyr Gly Ala Ser Asn Arg
 65                  70                  75                  80

Tyr Ile Gly Val Pro Asp Arg Phe Thr Gly Ser Gly Ser Gly Thr Asp
                 85                  90                  95

Phe Thr Leu Thr Ile Ser Ser Val Gln Val Glu Asp Leu Thr His Tyr
            100                 105                 110

Tyr Cys Ala Gln Phe Tyr Ser Tyr Pro Tyr Thr Phe Gly Gly Gly Lys
        115                 120                 125

Leu Glu Ile Lys
    130

<210> SEQ ID NO 26
<211> LENGTH: 17
<212> TYPE: PRT
<213> ORGANISM: Artificial Sequence
<220> FEATURE:
<223> OTHER INFORMATION: Amino Acid sequence of light chain CDR1 of
      monoclonal antibody 180A 3D3

<400> SEQUENCE: 26

Thr Ala Ser Glu Ser Leu Tyr Ser Ser Lys His Lys Val His Tyr Leu
1               5                   10                  15

Ala

<210> SEQ ID NO 27
<211> LENGTH: 7
<212> TYPE: PRT
<213> ORGANISM: Artificial sequence
<220> FEATURE:
<223> OTHER INFORMATION: Amino Acid sequence of light chain CDR2 of
      monoclonal antibody 180A 3D3

<400> SEQUENCE: 27

Gly Ala Ser Asn Arg Tyr Ile
1               5

<210> SEQ ID NO 28
<211> LENGTH: 9
<212> TYPE: PRT
<213> ORGANISM: Artificial sequence
<220> FEATURE:
<223> OTHER INFORMATION: Amino Acid sequence of light chain CDR3 of
      monoclonal antibody 180A 3D3

<400> SEQUENCE: 28

Ala Gln Phe Tyr Ser Tyr Pro Tyr Thr
1               5

<210> SEQ ID NO 29
<211> LENGTH: 411
<212> TYPE: DNA
<213> ORGANISM: Artificial sequence
<220> FEATURE:
<223> OTHER INFORMATION: DNA sequence of heavy chain of monoclonal
      antibody 180A 3D3

<400> SEQUENCE: 29
atgtacttgg gactgaactg tgtattcata gtttttctct taaaaggtgt ccagagtgaa      60
gtaaaccttg aggagtctgg aggaggcttg gtgcaacctg gaggatccat gaaactctcc    120
tgtgttgctc tggattcact ttcagtaact actggatgaa ctgggtccgc cagtctccag    180
```

```
agaggggggct tgagtgggtt gctgaaatta gcttgaaatc ttataactat gcaacacatt      240
atgcggagtc tgtgaaggga ggttcaccat ctcaggagat gaatccaaaa atagtgtcta      300
cctgcaaatg aacaacttaa gagctgaaga tactggcatt tatttctgta ccaggggaga      360
ttcctatgct ctggactact gggtcaaaga accttagtca ccgtctcctc a               411

<210> SEQ ID NO 30
<211> LENGTH: 15
<212> TYPE: DNA
<213> ORGANISM: Artificial sequence
<220> FEATURE:
<223> OTHER INFORMATION: DNA sequence of heavy chain CDR1 of monoclonal
      antibody 180A 3D3

<400> SEQUENCE: 30
aactactgga tgaac                                                        15

<210> SEQ ID NO 31
<211> LENGTH: 56
<212> TYPE: DNA
<213> ORGANISM: Artificial sequence
<220> FEATURE:
<223> OTHER INFORMATION: DNA sequence of heavy chain CDR2 of monoclonal
      antibody 180A 3D3

<400> SEQUENCE: 31
gaaattagct tgaaatctta taactatgca acacattatg cggagtctgt gaaggg          56

<210> SEQ ID NO 32
<211> LENGTH: 24
<212> TYPE: DNA
<213> ORGANISM: Artificial Sequence
<220> FEATURE:
<223> OTHER INFORMATION: DNA sequence of heavy chain CDR3 of monoclonal
      antibody 180A 3D3

<400> SEQUENCE: 32
ggagattcct atgctctgga ctac                                              24

<210> SEQ ID NO 33
<211> LENGTH: 396
<212> TYPE: DNA
<213> ORGANISM: Artificial sequence
<220> FEATURE:
<223> OTHER INFORMATION: DNA sequence of light chain of monoclonal
      antibody 180A 3D3

<400> SEQUENCE: 33
atggagtttc agacccaggt actcatgtcc ctgctgctct gcatgtctgg tgcctgtgca       60
gacattgtga tgactcagtc tccaactttc cttgctgtga cagtaagtaa gaaggtcacc      120
attagttcac ggccagtgag agcctttatt caagcaaaca aaggtgcac tacttggctt       180 ggtaccagaa gaaaccagag caatctccta aactgctgat atacggggca tccaaccgat      240
acattggggt ccctatcgct tcacaggcag tggatctggg acagatttca ctctgaccat      300
cagcagtgta caggttgaag acctcacaca ttattactgt gcacagtttt acagctatcc      360
gtacacgttc ggagggggga caagctggaa ataaaa                                396

<210> SEQ ID NO 34
<211> LENGTH: 51
<212> TYPE: DNA
```

<213> ORGANISM: Artificial Sequence
<220> FEATURE:
<223> OTHER INFORMATION: DNA sequence of light chain CDR1 of monoclonal
      antibody 180A 3D3

<400> SEQUENCE: 34
acggccagtg agagccttta ttcaagcaaa cacaaggtgc actacttggc t                51

<210> SEQ ID NO 35
<211> LENGTH: 21
<212> TYPE: DNA
<213> ORGANISM: Artificial sequence
<220> FEATURE:
<223> OTHER INFORMATION: DNA sequence of light chain CDR2 of monoclonal
      antibody 180A 3D3

<400> SEQUENCE: 35
ggggcatcca accgatacat t                                                  21

<210> SEQ ID NO 36
<211> LENGTH: 27
<212> TYPE: DNA
<213> ORGANISM: Artificial sequence
<220> FEATURE:
<223> OTHER INFORMATION: DNA sequence of light chain CDR3 of monoclonal
      antibody 180A 3D3

<400> SEQUENCE: 36
gcacagtttt acagctatcc gtacacg                                            27

<210> SEQ ID NO 37
<211> LENGTH: 118
<212> TYPE: PRT
<213> ORGANISM: Artificial sequence
<220> FEATURE:
<223> OTHER INFORMATION: Amino Acid sequence of heavy chain variable
      region of monoclonal antibody 180A 3D3

<400> SEQUENCE: 37

Glu Val Asn Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Arg Gly Leu Glu Trp Val
        35                  40                  45

Ala Glu Ile Ser Leu Lys Ser Tyr Asn Tyr Ala Thr His Tyr Ala Glu
    50                  55                  60

Ser Val Lys Gly Arg Phe Thr Ile Ser Gly Asp Glu Ser Lys Asn Ser
65                  70                  75                  80

Val Tyr Leu Gln Met Asn Asn Leu Arg Ala Glu Asp Thr Gly Ile Tyr
                85                  90                  95

Phe Cys Thr Arg Gly Asp Ser Tyr Ala Leu Asp Tyr Gly Gln Arg Thr
            100                 105                 110

Leu Val Thr Val Ser Ser
        115

<210> SEQ ID NO 38
<211> LENGTH: 112
<212> TYPE: PRT
<213> ORGANISM: Artificial sequence
<220> FEATURE:
<223> OTHER INFORMATION: Amino Acid sequence of light chain variable
      region of monoclonal antibody 180A 3D3

<400> SEQUENCE: 38

Asp Ile Val Met Thr Gln Ser Pro Thr Phe Leu Ala Val Thr Val Ser
1               5                   10                  15

Lys Lys Val Thr Ile Ser Cys Thr Ala Ser Glu Ser Leu Tyr Ser Ser
            20                  25                  30

Lys His Lys Val His Tyr Leu Ala Trp Tyr Gln Lys Pro Glu Gln
        35                  40                  45

Ser Pro Lys Leu Leu Ile Tyr Gly Ala Ser Asn Arg Tyr Ile Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Val Glu Asp Leu Thr His Tyr Tyr Cys Ala Gln
                85                  90                  95

Phe Tyr Ser Tyr Pro Tyr Thr Phe Gly Gly Gly Lys Leu Glu Ile Lys
            100                 105                 110

<210> SEQ ID NO 39
<211> LENGTH: 284
<212> TYPE: DNA
<213> ORGANISM: Artificial Sequence
<220> FEATURE:
<223> OTHER INFORMATION: DNA sequence of heavy chain variable region of
      monoclonal antibody 180A 3D3

<400> SEQUENCE: 39
ctctggattc actttcagta actactggat gaactgggtc cgccagtctc cagagagggg      60
gcttgagtgg gttgctgaaa ttagcttgaa atcttataac tatgcaacac attatgcgga    120
gtctgtgaag ggaggttcac catctcagga gatgaatcca aaaatagtgt ctacctgcaa    180
atgaacaact taagagctga agatactggc atttatttct gtaccagggg agattcctat    240
gctctggact actgggtcaa agaaccttag tcaccgtctc ctca                     284

<210> SEQ ID NO 40
<211> LENGTH: 336
<212> TYPE: DNA
<213> ORGANISM: Artificial Sequence
<220> FEATURE:
<223> OTHER INFORMATION: DNA sequence of light chain variable region of
      monoclonal antibody 180A 3D3

<400> SEQUENCE: 40
gacattgtga tgactcagtc tccaactttc cttgctgtga cagtaagtaa gaaggtcacc      60
attagttcac ggccagtgag agcctttatt caagcaaaca caaggtgcac tacttggctt    120
ggtaccagaa gaaaccagag caatctccta aactgctgat atacggggca tccaaccgat    180
acattggggt ccctatcgct tcacaggcag tggatctggg acagatttca ctctgaccat    240
cagcagtgta caggttgaag acctcacaca ttattactgt gcacagtttt acagctatcc    300
gtacacgttc ggagggggga caagctggaa ataaaa                              336

<210> SEQ ID NO 41
<211> LENGTH: 135
<212> TYPE: PRT
<213> ORGANISM: Artificial Sequence
<220> FEATURE:
<223> OTHER INFORMATION: Amino Acid sequence of heavy chain of
      monoclonal antibody 180B 13F7

<400> SEQUENCE: 41

Met Arg Val Leu Ile Leu Val Tyr Leu Leu Thr Ala Leu Pro Gly Ile
1               5                   10                  15

Leu Ser Asp Ile Gln Leu Gln Glu Ser Gly Pro Gly Leu Val Lys Pro
            20                  25                  30

Ser Gln Thr Val Ser Leu Thr Cys Thr Val Thr Gly Tyr Ser Ile Thr
        35                  40                  45

Tyr Val Asn His Trp Trp Asn Trp Ile Arg Gln Val Ser Gly Asn Lys
    50                  55                  60

Leu Glu Trp Ile Gly Tyr Ile Ser Ser Ser Gly Ser Ile Asp Ser Asn
65                  70                  75                  80

Pro Ser Leu Lys Ser Arg Ile Ala Ile Thr Arg Asp Thr Ser Lys Asn
                85                  90                  95

Gln Leu Phe Leu Gln Leu Lys Ser Val Thr Thr Glu Asp Val Gly Thr
            100                 105                 110

Tyr Tyr Cys Val Ser Glu Asp Ser Ser Gly Tyr His Tyr Trp Gly Gly
        115                 120                 125

Thr Thr Leu Thr Val Ser Ser
    130                 135

<210> SEQ ID NO 42
<211> LENGTH: 7
<212> TYPE: PRT
<213> ORGANISM: Artificial Sequence
<220> FEATURE:
<223> OTHER INFORMATION: Amino Acid sequence of heavy chain CDR1 of
      monoclonal antibody 180B 13F7

<400> SEQUENCE: 42

Tyr Val Asn His Trp Trp Asn
1               5

<210> SEQ ID NO 43
<211> LENGTH: 16
<212> TYPE: PRT
<213> ORGANISM: Artificial Sequence
<220> FEATURE:
<223> OTHER INFORMATION: Amino Acid sequence of heavy chain CDR2 of
      monoclonal antibody 180B 13F7

<400> SEQUENCE: 43

Tyr Ile Ser Ser Ser Gly Ser Ile Asp Ser Asn Pro Ser Leu Lys Ser
1               5                   10                  15

<210> SEQ ID NO 44
<211> LENGTH: 8
<212> TYPE: PRT
<213> ORGANISM: Artificial sequence
<220> FEATURE:
<223> OTHER INFORMATION: Amino Acid sequence of heavy chain CDR3 of
      monoclonal antibody 180B 13F7

<400> SEQUENCE: 44

Glu Asp Ser Ser Gly Tyr His Tyr
1               5

<210> SEQ ID NO 45
<211> LENGTH: 131
<212> TYPE: PRT
<213> ORGANISM: Artificial Sequence

```
<220> FEATURE:
<223> OTHER INFORMATION: Amino Acid sequence of light chain of
      monoclonal antibody 180B 13F7

<400> SEQUENCE: 45

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val Phe Ser Asn Gly Lys Thr Tyr Phe His Trp Tyr Leu Gln Lys Pro
50                  55                  60

Gly Gln Ser Pro Lys Leu Leu Ile Tyr Arg Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Trp Thr Phe Gly Gly Gly Thr Lys Leu
        115                 120                 125

Glu Ile Lys
    130

<210> SEQ ID NO 46
<211> LENGTH: 16
<212> TYPE: PRT
<213> ORGANISM: Artificial Sequence
<220> FEATURE:
<223> OTHER INFORMATION: Amino Acid sequence of light chain CDR1 of
      monoclonal antibody 180B 13F7

<400> SEQUENCE: 46

Arg Ser Ser Gln Ser Leu Val Phe Ser Asn Gly Lys Thr Tyr Phe His
1               5                   10                  15

<210> SEQ ID NO 47
<211> LENGTH: 7
<212> TYPE: PRT
<213> ORGANISM: Artificial Sequence
<220> FEATURE:
<223> OTHER INFORMATION: Amino Acid sequence of light chain CDR2 of
      monoclonal antibody 180B 13F7

<400> SEQUENCE: 47

Arg Val Ser Asn Arg Phe Ser
1               5

<210> SEQ ID NO 48
<211> LENGTH: 9
<212> TYPE: PRT
<213> ORGANISM: Artificial Sequence
<220> FEATURE:
<223> OTHER INFORMATION: Amino Acid sequence of light chain CDR3 of
      monoclonal antibody 180B 13F7

<400> SEQUENCE: 48

Ser Gln Ser Thr His Val Pro Trp Thr
1               5

<210> SEQ ID NO 49
<211> LENGTH: 405
<212> TYPE: DNA
```

```
<213> ORGANISM: Artificial Sequence
<220> FEATURE:
<223> OTHER INFORMATION: DNA sequence of heavy chain of monoclonal
      antibody 180B 13F7

<400> SEQUENCE: 49
atgagagtgt tgattcttgt gtacctgttg acagcccttc ctggtatctt gtctgatata      60
cagcttcagg agtcaggacc tggcctggtg aagccttctc agacagtgtc cctcacctgc     120
actgtcatgg ctactctatc acttatgtta atcactggtg aactggatc cggcaggttt      180 caggaaacaa actggagtgg ataggtaca taagttccag tggcagtatt gacagcaatc      240
catctctcaa aagtgaatcg ccatcactag agacacttcc aagaaccagt tattcttgca     300
gttgaaatct gtgactactg aagatgtggg cacatattac tgtgtaagcg aagacagctc     360
gggataccac tactggggcc aggcactact ctcacagtct cctca                     405

<210> SEQ ID NO 50
<211> LENGTH: 21
<212> TYPE: DNA
<213> ORGANISM: Artificial Sequence
<220> FEATURE:
<223> OTHER INFORMATION: DNA sequence of heavy chain CDR1 of monoclonal
      antibody 180B 13F7

<400> SEQUENCE: 50
tatgttaatc actggtggaa c                                                21

<210> SEQ ID NO 51
<211> LENGTH: 48
<212> TYPE: DNA
<213> ORGANISM: Artificial Sequence
<220> FEATURE:
<223> OTHER INFORMATION: DNA sequence of heavy chain CDR2 of monoclonal
      antibody 180B 13F7

<400> SEQUENCE: 51
tacataagtt ccagtggcag tattgacagc aatccatctc tcaaaagt                   48

<210> SEQ ID NO 52
<211> LENGTH: 24
<212> TYPE: DNA
<213> ORGANISM: Artificial Sequence
<220> FEATURE:
<223> OTHER INFORMATION: DNA sequence of heavy chain CDR3 of monoclonal
      antibody 180B 13F7

<400> SEQUENCE: 52
gaagacagct cgggatacca ctac                                             24

<210> SEQ ID NO 53
<211> LENGTH: 390
<212> TYPE: DNA
<213> ORGANISM: Artificial Sequence
<220> FEATURE:
<223> OTHER INFORMATION: DNA sequence of light chain of monoclonal
      antibody 180B 13F7

<400> SEQUENCE: 53
atgaagttgc ctgttaggct gttggtgctg atgttctgga ttcctgcttc cagtagtgat      60
gttgtgatga cccaaactcc actctccctg cctgtcagtc ttggagatca agcctccatc     120
tcttgcagtc tagtcagagc cttgtattca gtaatgaaaa aacctatttc cattggtacc     180
tgcagaagcc aggccagtct ccaaagctcc tgatctacag agtttccaac cgattttctg     240
```

```
gggtcccaga caggtcagtg gcagtggatc agggacagat ttcacactca agatcagcag    300
agtggaggct gaggatctgg gagtttattt ctgctctcaa agtacacatg ttccgtggac    360
gttcggtgga ggcaccaagc tgaaatcaaa                                     390
```

<210> SEQ ID NO 54
<211> LENGTH: 47
<212> TYPE: DNA
<213> ORGANISM: Artificial sequence
<220> FEATURE:
<223> OTHER INFORMATION: DNA sequence of light chain CDR1 of monoclonal
      antibody 180B 13F7

<400> SEQUENCE: 54

```
agtctagtca gagccttgta ttcagtaatg gaaaaaccta tttccat                   47
```

<210> SEQ ID NO 55
<211> LENGTH: 21
<212> TYPE: DNA
<213> ORGANISM: Artificial sequence
<220> FEATURE:
<223> OTHER INFORMATION: DNA sequence of light chain CDR2 of monoclonal
      antibody 180B 13F7

<400> SEQUENCE: 55

```
agagtttcca accgattttc t                                               21
```

<210> SEQ ID NO 56
<211> LENGTH: 27
<212> TYPE: DNA
<213> ORGANISM: Artificial sequence
<220> FEATURE:
<223> OTHER INFORMATION: DNA sequence of light chain CDR3 of monoclonal
      antibody 180B 13F7

<400> SEQUENCE: 56

```
tctcaaagta cacatgttcc gtggacg                                         27
```

<210> SEQ ID NO 57
<211> LENGTH: 117
<212> TYPE: PRT
<213> ORGANISM: Artificial Sequence
<220> FEATURE:
<223> OTHER INFORMATION: Amino Acid sequence of heavy chain variable
      region of monoclonal antibody 180B 13F7

<400> SEQUENCE: 57

```
Asp Ile Gln Leu Gln Glu Ser Gly Pro Gly Leu Val Lys Pro Ser Gln
1               5                   10                  15

Thr Val Ser Leu Thr Cys Thr Val Thr Gly Tyr Ser Ile Thr Tyr Val
            20                  25                  30

Asn His Trp Trp Asn Trp Ile Arg Gln Val Ser Gly Asn Lys Leu Glu
        35                  40                  45

Trp Ile Gly Tyr Ile Ser Ser Gly Ser Ile Asp Ser Asn Pro Ser
    50                  55                  60

Leu Lys Ser Arg Ile Ala Ile Thr Arg Asp Thr Ser Lys Asn Gln Leu
65                  70                  75                  80

Phe Leu Gln Leu Lys Ser Val Thr Thr Glu Asp Val Gly Thr Tyr Tyr
                85                  90                  95

Cys Val Ser Glu Asp Ser Ser Gly Tyr His Tyr Trp Gly Gly Thr Thr
            100                 105                 110

Leu Thr Val Ser Ser
        115
```

<210> SEQ ID NO 58
<211> LENGTH: 112
<212> TYPE: PRT
<213> ORGANISM: Artificial Sequence
<220> FEATURE:
<223> OTHER INFORMATION: Amino Acid sequence of light chain variable
      region of monoclonal antibody 180B 13F7

<400> SEQUENCE: 58

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Phe Ser
            20                  25                  30

Asn Gly Lys Thr Tyr Phe His Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 59
<211> LENGTH: 405
<212> TYPE: DNA
<213> ORGANISM: Artificial Sequence
<220> FEATURE:
<223> OTHER INFORMATION: DNA sequence of heavy chain variable region of
      monoclonal antibody 180B 13F7

<400> SEQUENCE: 59
atgagagtgt tgattcttgt gtacctgttg acagcccttc ctggtatctt gtctgatata      60
cagcttcagg agtcaggacc tggcctggtg aagccttctc agacagtgtc cctcacctgc    120
actgtcatgg ctactctatc acttatgtta atcactggtg aactggatc cggcaggttt     180 caggaaacaa actggagtgg ataggggtaca taagttccag tggcagtatt gacagcaatc   240
catctctcaa aagtgaatcg ccatcactag agacacttcc aagaaccagt tattcttgca    300
gttgaaatct gtgactactg aagatgtggg cacatattac tgtgtaagcg aagacagctc    360
gggataccac tactggggcc aggcactact ctcacagtct cctca                    405

<210> SEQ ID NO 60
<211> LENGTH: 333
<212> TYPE: DNA
<213> ORGANISM: Artificial Sequence
<220> FEATURE:
<223> OTHER INFORMATION: DNA sequence of light chain variable region of
      monoclonal antibody 180B 13F7

<400> SEQUENCE: 60
gatgttgtga tgacccaaac tccactctcc ctgcctgtca gtcttggaga tcaagcctcc      60
atctcttgca gtctagtcag agccttgtat tcagtaatgg aaaaacctat ttccattggt    120
acctgcagaa gccaggccag tctccaaagc tcctgatcta cagagtttcc aaccgatttt    180
ctggggtccc agacaggtca gtggcagtgg atcagggaca gatttcacac tcaagatcag    240

```
cagagtggag gctgaggatc tgggagttta tttctgctct caaagtacac atgttccgtg        300
gacgttcggt ggaggcacca agctgaaatc aaa                                    333
```

<210> SEQ ID NO 61
<211> LENGTH: 134
<212> TYPE: PRT
<213> ORGANISM: Artificial Sequence
<220> FEATURE:
<223> OTHER INFORMATION: Amino Acid sequence of heavy chain of
      monoclonal antibody 180C 1F8

<400> SEQUENCE: 61

```
Met Glu Trp Ser Trp Ile Phe Leu Phe Phe Leu Ser Val Thr Thr Gly
1               5                   10                  15

Val His Ser Gln Val Gln Leu Gln Gln Ser Asp Ala Glu Leu Val Lys
            20                  25                  30

Pro Gly Thr Ser Val Lys Ile Ser Cys Lys Ala Ser Gly Phe Thr Phe
        35                  40                  45

Thr Asp His Ala Ile His Trp Val Lys Gln Arg Pro Glu Gln Gly Leu
    50                  55                  60

Glu Trp Ile Gly Tyr Ile Ser Pro Gly Asn Gly Asp Ile Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Asn Ser Leu Thr Ser Glu Asp Ser Ala Val
            100                 105                 110

Tyr Phe Cys Asp Tyr Tyr Asn Gly Arg Val Asp Tyr Trp Gly Gln Thr
        115                 120                 125

Thr Leu Thr Val Ser Ser
    130
```

<210> SEQ ID NO 62
<211> LENGTH: 5
<212> TYPE: PRT
<213> ORGANISM: Artificial Sequence
<220> FEATURE:
<223> OTHER INFORMATION: Amino Acid sequence of heavy chain CDR1 of
      monoclonal antibody 180C 1F8

<400> SEQUENCE: 62

```
Asp His Ala Ile His
1               5
```

<210> SEQ ID NO 63
<211> LENGTH: 17
<212> TYPE: PRT
<213> ORGANISM: Artificial Sequence
<220> FEATURE:
<223> OTHER INFORMATION: Amino Acid sequence of heavy chain CDR2 of
      monoclonal antibody 180C 1F8

<400> SEQUENCE: 63

```
Tyr Ile Ser Pro Gly Asn Gly Asp Ile Lys Tyr Asn Glu Lys Phe Lys
1               5                   10                  15

Gly
```

<210> SEQ ID NO 64
<211> LENGTH: 7
<212> TYPE: PRT
<213> ORGANISM: Artificial Sequence
<220> FEATURE:

```
<223> OTHER INFORMATION: Amino Acid sequence of heavy chain CDR3 of
      monoclonal antibody 180C 1F8

<400> SEQUENCE: 64

Tyr Asn Gly Arg Val Asp Tyr
1               5

<210> SEQ ID NO 65
<211> LENGTH: 127
<212> TYPE: PRT
<213> ORGANISM: Artificial Sequence
<220> FEATURE:
<223> OTHER INFORMATION: Amino Acid sequence of light chain of
      monoclonal antibody 180C 1F8

<400> SEQUENCE: 65

Met Glu Phe His Thr Gln Val Phe Val Phe Val Phe Leu Trp Leu Ser
1               5                   10                  15

Gly Val Asp Gly Asp Ile Val Met Thr Gln Ser Gln Lys Phe Met Thr
            20                  25                  30

Thr Ser Val Gly Asp Arg Val Ser Ile Thr Cys Lys Ala Ser Gln Asn
        35                  40                  45

Val Gly Ser Ala Val Ala Trp Tyr Gln Gln Lys Pro Gly Gln Ser Pro
    50                  55                  60

Lys Leu Leu Ile Tyr Ser Ala Ser Asn Arg Phe Thr Gly Val Pro Asp
65                  70                  75                  80

Arg Phe Thr Gly Ser Gly Ser Arg Thr Asp Phe Thr Leu Thr Ile Ser
                85                  90                  95

Asn Met Gln Ser Asp Asp Leu Ala Asp Tyr Phe Cys His Gln Tyr Arg
            100                 105                 110

Ser Tyr Pro Tyr Thr Phe Gly Gly Thr Lys Leu Glu Ile Lys
        115                 120                 125

<210> SEQ ID NO 66
<211> LENGTH: 11
<212> TYPE: PRT
<213> ORGANISM: Artificial Sequence
<220> FEATURE:
<223> OTHER INFORMATION: Amino Acid sequence of light chain CDR1 of
      monoclonal antibody 180C 1F8

<400> SEQUENCE: 66

Lys Ala Ser Gln Asn Val Gly Ser Ala Val Ala
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Amino Acid sequence of light chain CDR2 of
      monoclonal antibody 180C 1F8

<400> SEQUENCE: 67

Ser Ala Ser Asn Arg Phe Thr
1               5

<210> SEQ ID NO 68
<211> LENGTH: 9
<212> TYPE: PRT
<213> ORGANISM: Artificial Sequence
<220> FEATURE:
<223> OTHER INFORMATION: Amino Acid sequence of light chain CDR3 of
      monoclonal antibody 180C 1F8
```

<400> SEQUENCE: 68

His Gln Tyr Arg Ser Tyr Pro Tyr Thr
1               5

<210> SEQ ID NO 69
<211> LENGTH: 402
<212> TYPE: DNA
<213> ORGANISM: Artificial Sequence
<220> FEATURE:
<223> OTHER INFORMATION: DNA sequence of heavy chain of monoclonal
      antibody 180C 1F8

<400> SEQUENCE: 69
atggaatgga gctggatctt tctcttcttc ctgtcagtaa ctacaggtgt ccactcccag      60
gttcagctgc aacagtctga cgctgagttg gtgaaacctg ggacttcagt gaagatatcc     120
tgcaaggttc tggcttcacc ttcactgacc atgctattca ctgggtgaag cagaggcctg     180
aacagggcct ggaatggatt ggatatattt ctcccggaaa tggtgatatt aagtataatg     240
agaaattcaa gggcaggcca cactgactgc agacaaatcc tccagcactg cctacatgca     300
gctcaacagt ctgacatctg aagattctgc agtgtatttc tgtgattact acaatggtag     360
ggttgactac tggggccaag gaccactctc acagtctcct ca                        402

<210> SEQ ID NO 70
<211> LENGTH: 15
<212> TYPE: DNA
<213> ORGANISM: Artificial Sequence
<220> FEATURE:
<223> OTHER INFORMATION: DNA sequence of heavy chain CDR1 of monoclonal
      antibody 180C 1F8

<400> SEQUENCE: 70
gaccatgcta ttcac                                                       15

<210> SEQ ID NO 71
<211> LENGTH: 51
<212> TYPE: DNA
<213> ORGANISM: Artificial Sequence
<220> FEATURE:
<223> OTHER INFORMATION: DNA sequence of heavy chain CDR2 of monoclonal
      antibody 180C 1F8

<400> SEQUENCE: 71
tatatttctc ccggaaatgg tgatattaag tataatgaga aattcaaggg c               51

<210> SEQ ID NO 72
<211> LENGTH: 21
<212> TYPE: DNA
<213> ORGANISM: Artificial Sequence
<220> FEATURE:
<223> OTHER INFORMATION: DNA sequence of heavy chain CDR1 of monoclonal
      antibody 180C 1F8

<400> SEQUENCE: 72
tacaatggta gggttgacta c                                                21

<210> SEQ ID NO 73
<211> LENGTH: 379
<212> TYPE: DNA
<213> ORGANISM: Artificial Sequence
<220> FEATURE:
<223> OTHER INFORMATION: DNA sequence of light chain of monoclonal
      antibody 180C 1F8

-continued

<400> SEQUENCE: 73

```
atggagtttc atactcaggt ctttgtattc gtgtttctct ggttgtctgg tgttgatgga    60
gacattgtga tgacccagtc tcaaaagttc atgaccacgt cagtaggaga cagggtcagt   120
atcacctcaa ggccagtcag aatgtgggct ctgctgtagc ctggtatcaa cagaaaccag   180
gacaatctcc taaacttctg atttactcag catccaatcg gttcactgga gtccctgatc   240
gcttcacagg cagtgatctc ggacagattt cactctcacc attagcaata tgcagtctga   300
tgacctggca gattatttct gtcaccaata taggagctat ccgtacacgt tcggagggg   360 gaccaagctg gaaataaaa                                                 379
```

<210> SEQ ID NO 74
<211> LENGTH: 33
<212> TYPE: DNA
<213> ORGANISM: Artificial Sequence
<220> FEATURE:
<223> OTHER INFORMATION: DNA sequence of light chain CDR1 of monoclonal
      antibody 180C 1F8

<400> SEQUENCE: 74

```
aaggccagtc agaatgtggg ctctgctgta gcc                                  33
```

<210> SEQ ID NO 75
<211> LENGTH: 21
<212> TYPE: DNA
<213> ORGANISM: Artificial Sequence
<220> FEATURE:
<223> OTHER INFORMATION: DNA sequence of light chain CDR2 of monoclonal
      antibody 180C 1F8

<400> SEQUENCE: 75

```
tcagcatcca atcggttcac t                                               21
```

<210> SEQ ID NO 76
<211> LENGTH: 27
<212> TYPE: DNA
<213> ORGANISM: Artificial Sequence
<220> FEATURE:
<223> OTHER INFORMATION: DNA sequence of light chain CDR3 of monoclonal
      antibody 180C 1F8

<400> SEQUENCE: 76

```
caccaatata ggagctatcc gtacacg                                         27
```

<210> SEQ ID NO 77
<211> LENGTH: 115
<212> TYPE: PRT
<213> ORGANISM: Artificial Sequence
<220> FEATURE:
<223> OTHER INFORMATION: Amino Acid sequence of heavy chain variable
      region of monoclonal antibody 180C 1F8

<400> SEQUENCE: 77

```
Gln Val Gln Leu Gln Gln Ser Asp Ala Glu Leu Val Lys Pro Gly Thr
 1               5                  10                  15

Ser Val Lys Ile Ser Cys Lys Ala Ser Gly Phe Thr Phe Thr Asp His
             20                  25                  30

Ala Ile His Trp Val Lys Gln Arg Pro Glu Gln Gly Leu Glu Trp Ile
         35                  40                  45

Gly Tyr Ile Ser Pro Gly Asn Gly Asp Ile Lys Tyr Asn Glu Lys Phe
     50                  55                  60
```

```
Lys Gly Lys Ala Thr Leu Thr Ala Asp Lys Ser Ser Thr Ala Tyr
 65                  70                  75                  80

Met Gln Leu Asn Ser Leu Thr Ser Glu Asp Ser Ala Val Tyr Phe Cys
                 85                  90                  95

Asp Tyr Tyr Asn Gly Arg Val Asp Tyr Trp Gly Gln Thr Thr Leu Thr
            100                 105                 110

Val Ser Ser
        115

<210> SEQ ID NO 78
<211> LENGTH: 107
<212> TYPE: PRT
<213> ORGANISM: Artificial sequence
<220> FEATURE:
<223> OTHER INFORMATION: Amino Acid sequence of light chain variable
      region of monoclonal antibody 180C 1F8

<400> SEQUENCE: 78

Asp Ile Val Met Thr Gln Ser Gln Lys Phe Met Thr Thr Ser Val Gly
1               5                   10                  15

Asp Arg Val Ser Ile Thr Cys Lys Ala Ser Gln Asn Val Gly Ser Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Phe Thr Gly Val Pro Asp Arg Phe Thr Gly
    50                  55                  60

Ser Gly Ser Arg Thr Asp Phe Thr Leu Thr Ile Ser Asn Met Gln Ser
65                  70                  75                  80

Asp Asp Leu Ala Asp Tyr Phe Cys His Gln Tyr Arg Ser Tyr Pro Tyr
                85                  90                  95

Thr Phe Gly Gly Gly Thr Lys Leu Glu Ile Lys
            100                 105

<210> SEQ ID NO 79
<211> LENGTH: 345
<212> TYPE: DNA
<213> ORGANISM: Artificial Sequence
<220> FEATURE:
<223> OTHER INFORMATION: DNA sequence of heavy chain variable region of
      monoclonal antibody 180C 1F8

<400> SEQUENCE: 79
caggttcagc tgcaacagtc tgacgctgag ttggtgaaac ctgggacttc agtgaagata      60
tcctgcaagg ttctggcttc accttcactg accatgctat tcactgggtg aagcagaggc    120
ctgaacaggg cctggaatgg attggatata tttctcccgg aaatggtgat attaagtata    180
atgagaaatt caaggcagg ccacactgac tgcagacaaa tcctccagca ctgcctacat     240
gcagctcaac agtctgacat ctgaagattc tgcagtgtat ttctgtgatt actacaatgg    300
tagggttgac tactggggcc aaggaccact ctcacagtct cctca                    345

<210> SEQ ID NO 80
<211> LENGTH: 319
<212> TYPE: DNA
<213> ORGANISM: Artificial Sequence
<220> FEATURE:
<223> OTHER INFORMATION: DNA sequence of light chain variable region of
      monoclonal antibody 180C 1F8
```

<400> SEQUENCE: 80

```
gacattgtga tgacccagtc tcaaaagttc atgaccacgt cagtaggaga cagggtcagt      60
atcacctcaa ggccagtcag aatgtgggct ctgctgtagc ctggtatcaa cagaaaccag     120
gacaatctcc taaacttctg atttactcag catccaatcg gttcactgga gtccctgatc     180
gcttcacagg cagtgatctc ggacagattt cactctcacc attagcaata tgcagtctga     240
tgacctggca gattatttct gtcaccaata taggagctat ccgtacacgt tcggaggggg     300
gaccaagctg gaaataaaa                                                  319
```

<210> SEQ ID NO 81
<211> LENGTH: 136
<212> TYPE: PRT
<213> ORGANISM: Artificial Sequence
<220> FEATURE:
<223> OTHER INFORMATION: Amino acid sequence of heavy chain of monoclonal antibody 180C 7G8

<400> SEQUENCE: 81

Met Tyr Leu Gly Leu Asn Cys Val Ile Ile Val Phe Leu Leu Lys Gly
1               5                   10                  15
Val Gln Ser Glu Val Lys Leu Glu Glu Ser Gly Gly Gly Leu Val Gln
            20                  25                  30
Pro Gly Gly Ser Val Lys Leu Ser Cys Ala Val Phe Gly Phe Thr Phe
        35                  40                  45
Ser Asp Pro Trp Met Asp Trp Val Arg Gln Ser Pro Glu Lys Gly Leu
    50                  55                  60
Glu Trp Val Ala Glu Ile Arg Asn Lys Ala Tyr Asn His Ala Thr Tyr
65                  70                  75                  80
Tyr Ala Glu Ser Val Lys Gly Arg Phe Thr Ile Ser Arg Asp Asp Ser
                85                  90                  95
Asn Ser Arg Val Ser Leu Gln Met Asn Asn Leu Arg Ala Glu Asp Thr
            100                 105                 110
Gly Val Tyr Tyr Cys Thr Ala Gly Asp Ser Ser His Ser Tyr Trp Gln
        115                 120                 125
Gly Thr Leu Val Thr Val Ser Ala
    130                 135

<210> SEQ ID NO 82
<211> LENGTH: 5
<212> TYPE: PRT
<213> ORGANISM: Artificial Sequence
<220> FEATURE:
<223> OTHER INFORMATION: Amino acid sequence of heavy chain CDR1 of monoclonal antibody 180C 7G8

<400> SEQUENCE: 82

Asp Pro Trp Met Asp
1               5

<210> SEQ ID NO 83
<211> LENGTH: 19
<212> TYPE: PRT
<213> ORGANISM: Artificial Sequence
<220> FEATURE:
<223> OTHER INFORMATION: Amino acid sequence of heavy chain CDR2 of monoclonal antibody 180C 7G8

<400> SEQUENCE: 83

Glu Ile Arg Asn Lys Ala Tyr Asn His Ala Thr Tyr Tyr Ala Glu Ser
1               5                   10                  15

Val Lys Gly

<210> SEQ ID NO 84
<211> LENGTH: 7
<212> TYPE: PRT
<213> ORGANISM: Artificial Sequence
<220> FEATURE:
<223> OTHER INFORMATION: Amino acid sequence of heavy chain CDR3 of
      monoclonal antibody 180C 7G8

<400> SEQUENCE: 84

Gly Asp Ser Ser His Ser Tyr
1               5

<210> SEQ ID NO 85
<211> LENGTH: 127
<212> TYPE: PRT
<213> ORGANISM: Artificial Sequence
<220> FEATURE:
<223> OTHER INFORMATION: Amino acid sequence of light chain of
      monoclonal antibody 180C 7G8

<400> SEQUENCE: 85

Met Glu Phe Gln Thr Gln Val Phe Val Phe Val Leu Leu Trp Leu Ser
1               5                   10                  15

Gly Val Asp Gly Asp Ile Val Met Thr Gln Ser Gln Lys Phe Met Ser
            20                  25                  30

Thr Ser Val Gly Asp Arg Val Ser Ile Ile Cys Lys Ala Ser Gln Asn
        35                  40                  45

Val Arg Thr Ala Val Ala Trp Tyr Gln Gln Lys Pro Gly Gln Ser Pro
    50                  55                  60

Lys Thr Leu Ile Tyr Leu Ala Ser Asn Arg His Thr Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ala Glu Asp Leu Ala Asp Tyr Phe Cys Leu Gln His Trp
            100                 105                 110

Asn Tyr Pro Leu Thr Phe Gly Gly Gly Thr Lys Leu Glu Ile Lys
        115                 120                 125

<210> SEQ ID NO 86
<211> LENGTH: 11
<212> TYPE: PRT
<213> ORGANISM: Artificial Sequence
<220> FEATURE:
<223> OTHER INFORMATION: Amino acid sequence of light chain CDR1 of
      monoclonal antibody 180C 7G8

<400> SEQUENCE: 86

Lys Ala Ser Gln Asn Val Arg Thr Ala Val Ala
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Amino acid sequence of light chain CDR2 of
      monoclonal antibody 180C 7G8

<400> SEQUENCE: 87

Leu Ala Ser Asn Arg His Thr
1               5

<210> SEQ ID NO 88
<211> LENGTH: 9
<212> TYPE: PRT
<213> ORGANISM: Artificial Sequence
<220> FEATURE:
<223> OTHER INFORMATION: Amino acid sequence of light chain CDR3 of
      monoclonal antibody 180C 7G8

<400> SEQUENCE: 88

Leu Gln His Trp Asn Tyr Pro Leu Thr
1               5

<210> SEQ ID NO 89
<211> LENGTH: 408
<212> TYPE: DNA
<213> ORGANISM: Artificial Sequence
<220> FEATURE:
<223> OTHER INFORMATION: DNA sequence of heavy chain of monoclonal
      antibody 180C 7G8

<400> SEQUENCE: 89
atgtacttgg gactgaactg tgtaatcata gtttttctct taaaaggtgt ccagagtgaa      60
gtgaaacttg aggagtctgg aggaggcttg gtgcaacctg gaggatccgt gaaactctct    120
tgtgctgttt tggattcact ttcagtgatc cctggatgga ctgggtccgc cagtcgccag    180
agaaggggct tgagtgggtt gctgaaatta gaaacaaagc ttataatcat gccacatatt    240
atgctgagtc tgttaaggga ggttcaccat ctcaagagat gattccaaca gtagagtgtc    300
cctgcaaatg aacaacttaa gagctgaaga cactggcgtt tattactgta ccgccggtga    360
ctccagtcat tcttattggg gcaagggact ctggtcactg tctctgca                 408

<210> SEQ ID NO 90
<211> LENGTH: 15
<212> TYPE: DNA
<213> ORGANISM: Artificial Sequence
<220> FEATURE:
<223> OTHER INFORMATION: DNA sequence of heavy chain CDR1 of monoclonal
      antibody 180C 7G8

<400> SEQUENCE: 90
gatccctgga tggac                                                      15

<210> SEQ ID NO 91
<211> LENGTH: 56
<212> TYPE: DNA
<213> ORGANISM: Artificial Sequence
<220> FEATURE:
<223> OTHER INFORMATION: DNA sequence of heavy chain CDR2 of monoclonal
      antibody 180C 7G8

<400> SEQUENCE: 91
gaaattagaa acaaagctta taatcatgcc acatattatg ctgagtctgt taaggg         56

<210> SEQ ID NO 92
<211> LENGTH: 21
<212> TYPE: DNA
<213> ORGANISM: Artificial Sequence
<220> FEATURE:
<223> OTHER INFORMATION: DNA sequence of heavy chain CDR3 of monoclonal
      antibody 180C 7G8

<400> SEQUENCE: 92
ggtgactcca gtcattctta t                                          21

<210> SEQ ID NO 93
<211> LENGTH: 379
<212> TYPE: DNA
<213> ORGANISM: Artificial Sequence
<220> FEATURE:
<223> OTHER INFORMATION: DNA sequence of light chain of monoclonal
      antibody 180C 7G8

<400> SEQUENCE: 93
atggagtttc agacccaggt ctttgtattc gtgttgctct ggttgtctgg tgttgatgga     60
gacattgtga tgacccagtc tcaaaaattc atgtccacat cagtaggaga cagggtcagc    120
atcatctcaa ggccagtcag aatgttcgta ctgctgtagc ctggtatcaa cagaaaccag    180
ggcagtctcc taaaacactg atttacttgg catccaaccg gcacactgga gtccctgatc    240
gcttcacagg cagtgatctg ggacagattt cactctcacc attagcaatg tacaagctga    300
agacctggca gattatttct gtctgcaaca ttggaattat cctctcacgt tcggaggggg    360
gaccaaactg gaaataaaa                                                 379

<210> SEQ ID NO 94
<211> LENGTH: 33
<212> TYPE: DNA
<213> ORGANISM: Artificial Sequence
<220> FEATURE:
<223> OTHER INFORMATION: DNA sequence of light chain CDR1 of monoclonal
      antibody 180C 7G8

<400> SEQUENCE: 94
aaggccagtc agaatgttcg tactgctgta gcc                              33

<210> SEQ ID NO 95
<211> LENGTH: 21
<212> TYPE: DNA
<213> ORGANISM: Artificial Sequence
<220> FEATURE:
<223> OTHER INFORMATION: DNA sequence of light chain CDR2 of monoclonal
      antibody 180C 7G8

<400> SEQUENCE: 95
ttggcatcca accggcacac t                                          21

<210> SEQ ID NO 96
<211> LENGTH: 27
<212> TYPE: DNA
<213> ORGANISM: Artificial Sequence
<220> FEATURE:
<223> OTHER INFORMATION: DNA sequence of light chain CDR3 of monoclonal
      antibody 180C 7G8

<400> SEQUENCE: 96
ctgcaacatt ggaattatcc tctcacg                                    27

<210> SEQ ID NO 97
<211> LENGTH: 117
<212> TYPE: PRT
<213> ORGANISM: Artificial Sequence
<220> FEATURE:
<223> OTHER INFORMATION: Amino acid sequence of heavy chain variable
      region of monoclonal antibody 180C 7G8

<400> SEQUENCE: 97

Glu Val Lys Leu Glu Glu Ser Gly Gly Gly Leu Val Gln Pro Gly Gly
1               5                   10                  15

Ser Val Lys Leu Ser Cys Ala Val Phe Gly Phe Thr Phe Ser Asp Pro
            20                  25                  30

Trp Met Asp Trp Val Arg Gln Ser Pro Glu Lys Gly Leu Glu Trp Val
        35                  40                  45

Ala Glu Ile Arg Asn Lys Ala Tyr Asn His Ala Thr Tyr Tyr Ala Glu
    50                  55                  60

Ser Val Lys Gly Arg Phe Thr Ile Ser Arg Asp Asp Ser Asn Ser Arg
65                  70                  75                  80

Val Ser Leu Gln Met Asn Asn Leu Arg Ala Glu Asp Thr Gly Val Tyr
                85                  90                  95

Tyr Cys Thr Ala Gly Asp Ser Ser His Ser Tyr Trp Gln Gly Thr Leu
            100                 105                 110

Val Thr Val Ser Ala
        115

<210> SEQ ID NO 98
<211> LENGTH: 107
<212> TYPE: PRT
<213> ORGANISM: Artificial Sequence
<220> FEATURE:
<223> OTHER INFORMATION: Amino acid sequence of light chain variable
      region of monoclonal antibody 180C 7G8

<400> SEQUENCE: 98

Asp Ile Val Met Thr Gln Ser Gln Lys Phe Met Ser Thr Ser Val Gly
1               5                   10                  15

Asp Arg Val Ser Ile Ile Cys Lys Ala Ser Gln Asn Val Arg Thr Ala
            20                  25                  30

Val Ala Trp Tyr Gln Gln Lys Pro Gly Gln Ser Pro Lys Thr Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ala
65                  70                  75                  80

Glu Asp Leu Ala Asp Tyr Phe Cys Leu Gln His Trp Asn Tyr Pro Leu
                85                  90                  95

Thr Phe Gly Gly Gly Thr Lys Leu Glu Ile Lys
            100                 105

<210> SEQ ID NO 99
<211> LENGTH: 351
<212> TYPE: DNA
<213> ORGANISM: Artificial Sequence
<220> FEATURE:
<223> OTHER INFORMATION: DNA sequence of heavy chain variable region of
      monoclonal antibody 180C 7G8

<400> SEQUENCE: 99
gaagtgaaac ttgaggagtc tggaggaggc ttggtgcaac tggaggatc cgtgaaactc      60 tcttgtgctg ttttggattc actttcagtg atccctggat ggactgggtc cgccagtcgc    120
cagagaaggg gcttgagtgg gttgctgaaa ttagaaacaa agcttataat catgccacat    180
attatgctga gtctgttaag ggaggttcac catctcaaga gatgattcca acagtagagt    240

```
gtccctgcaa atgaacaact taagagctga agacactggc gtttattact gtaccgccgg      300
tgactccagt cattcttatt ggggcaaggg actctggtca ctgtctctgc a              351
```

<210> SEQ ID NO 100
<211> LENGTH: 319
<212> TYPE: DNA
<213> ORGANISM: Artificial Sequence
<220> FEATURE:
<223> OTHER INFORMATION: DNA sequence of light chain variable region of
monoclonal antibody 180C 7G8

<400> SEQUENCE: 100

```
gacattgtga tgacccagtc tcaaaaattc atgtccacat cagtaggaga cagggtcagc      60
atcatctcaa ggccagtcag aatgttcgta ctgctgtagc ctggtatcaa cagaaaccag      120
ggcagtctcc taaaacactg atttacttgg catccaaccg gcacactgga gtccctgatc      180
gcttcacagg cagtgatctg ggacagattt cactctcacc attagcaatg tacaagctga      240
agacctggca gattatttct gtctgcaaca ttggaattat cctctcacgt tcggagggg      300 gaccaaactg gaaataaaa                                                  319
```

<210> SEQ ID NO 101
<211> LENGTH: 134
<212> TYPE: PRT
<213> ORGANISM: Artificial sequence
<220> FEATURE:
<223> OTHER INFORMATION: Amino acid sequence of heavy chain of
monoclonal antibody 180C 8A10

<400> SEQUENCE: 101

```
Met Gly Trp Ser Tyr Ile Phe Leu Phe Leu Val Ala Thr Val Thr Asp
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Asn Tyr Trp Ile Asn Trp Val Lys Gln Arg Pro Gly Gln Gly Leu
    50                  55                  60

Glu Trp Leu Gly Glu Ile Asn Pro Ser Asn Ser Asn Thr Lys Tyr Asn
65                  70                  75                  80

Glu Lys Phe Lys Ser Arg Ala Thr Leu Thr Ala Asp Lys Ser Ser Ser
                85                  90                  95

Thr Ala Tyr Met Gln Leu His Ser Leu Thr Ser Glu Asp Ser Ala Val
            100                 105                 110

Tyr Tyr Cys Asn Tyr Tyr Asp Gly Gly His Asp Ser Trp Gly Gln Thr
        115                 120                 125

Thr Leu Thr Val Ser Ser
    130
```

<210> SEQ ID NO 102
<211> LENGTH: 5
<212> TYPE: PRT
<213> ORGANISM: Artificial Sequence
<220> FEATURE:
<223> OTHER INFORMATION: Amino acid sequence of heavy chain CDR1 of
monoclonal antibody 180C 8A10

<400> SEQUENCE: 102

```
Asn Tyr Trp Ile Asn
1               5
```

```
<210> SEQ ID NO 103
<211> LENGTH: 17
<212> TYPE: PRT
<213> ORGANISM: Artificial Sequence
<220> FEATURE:
<223> OTHER INFORMATION: Amino acid sequence of heavy chain CDR2 of
      monoclonal antibody 180C 8A10

<400> SEQUENCE: 103

Glu Ile Asn Pro Ser Asn Ser Asn Thr Lys Tyr Asn Glu Lys Phe Lys
1               5                   10                  15

Ser

<210> SEQ ID NO 104
<211> LENGTH: 7
<212> TYPE: PRT
<213> ORGANISM: Artificial Sequence
<220> FEATURE:
<223> OTHER INFORMATION: Amino acid sequence of heavy chain CDR3 of
      monoclonal antibody 180C 8A10

<400> SEQUENCE: 104

Tyr Asp Gly Gly His Asp Ser
1               5

<210> SEQ ID NO 105
<211> LENGTH: 127
<212> TYPE: PRT
<213> ORGANISM: Artificial sequence
<220> FEATURE:
<223> OTHER INFORMATION: Amino acid sequence of light chain of
      monoclonal antibody 180C 8A10

<400> SEQUENCE: 105

Met Glu Phe His Thr Gln Val Phe Val Phe Val Leu Trp Leu Ser
1               5                   10                  15

Gly Val Asp Gly Asp Ile Val Met Thr Gln Ser Gln Lys Phe Met Ser
                20                  25                  30

Thr Thr Leu Gly Asp Arg Val Ser Ile Ile Cys Lys Ala Ser Gln Asn
            35                  40                  45

Val Gly Thr Ala Val Ala Trp Tyr Gln Gln Lys Pro Gly Gln Ser Pro
        50                  55                  60

Lys Leu Leu Ile Tyr Ser Thr Ser Asn Arg Tyr Thr Gly Val Pro Asp
65                  70                  75                  80

Arg Phe Thr Gly Ser Gly Ser Gly Thr Asp Phe Ser Leu Thr Ile Ser
                85                  90                  95

Ser Val Gln Ser Glu Asp Leu Ala Asp Tyr Phe Cys His Gln Tyr Ser
            100                 105                 110

Ser Tyr Leu Tyr Thr Phe Gly Gly Gly Thr Arg Leu Glu Ile Lys
        115                 120                 125

<210> SEQ ID NO 106
<211> LENGTH: 11
<212> TYPE: PRT
<213> ORGANISM: Artificial Sequence
<220> FEATURE:
<223> OTHER INFORMATION: Amino acid sequence of light chain CDR1 of
      monoclonal antibody 180C 8A10

<400> SEQUENCE: 106

Lys Ala Ser Gln Asn Val Gly Thr Ala Val Ala
1               5                   10
```

<210> SEQ ID NO 107
<211> LENGTH: 7
<212> TYPE: PRT
<213> ORGANISM: Artificial Sequence
<220> FEATURE:
<223> OTHER INFORMATION: Amino acid sequence of light chain CDR2 of
monoclonal antibody 180C 8A10

<400> SEQUENCE: 107

Ser Thr Ser Asn Arg Tyr Thr
1               5

<210> SEQ ID NO 108
<211> LENGTH: 9
<212> TYPE: PRT
<213> ORGANISM: Artificial Sequence
<220> FEATURE:
<223> OTHER INFORMATION: Amino acid sequence of light chain CDR3 of
monoclonal antibody 180C 8A10

<400> SEQUENCE: 108

His Gln Tyr Ser Ser Tyr Leu Tyr Thr
1               5

<210> SEQ ID NO 109
<211> LENGTH: 402
<212> TYPE: DNA
<213> ORGANISM: Artificial Sequence
<220> FEATURE:
<223> OTHER INFORMATION: DNA sequence of heavy chain of monoclonal
antibody 180C 8A10

<400> SEQUENCE: 109
atgggatgga gctatatctt cctcttttg gtagcaacag ttacagatgt ccactcccag      60
gtccaactgc agcagcctgg ggctgagctt gtgaagcctg ggcttcagt gaagttgtcc     120 tgcaaggttc tggctacacc ttcaccaact actggataaa ctgggtgaaa cagaggcctg    180
ggcaaggcct tgagtggctt ggagaaatta atcctagcaa tagtaatact aaatataatg    240
agaaattcaa aagcgggcca cactgactgc agacaaatcc tccagcacag cctacatgca    300
actccacagc ctaacctctg aggactctgc ggtctactac tgtaattatt acgatggtgg    360
ccacgactcc tggggccagg gaccactctc acagtctcct ca                       402

<210> SEQ ID NO 110
<211> LENGTH: 15
<212> TYPE: DNA
<213> ORGANISM: artificial Sequence
<220> FEATURE:
<223> OTHER INFORMATION: DNA sequence of heavy chain CDR1 of monoclonal
antibody 180C 8A10

<400> SEQUENCE: 110
aactactgga taaac                                                      15

<210> SEQ ID NO 111
<211> LENGTH: 51
<212> TYPE: DNA
<213> ORGANISM: Artificial Sequence
<220> FEATURE:
<223> OTHER INFORMATION: DNA sequence of heavy chain CDR2 of monoclonal
antibody 180C 8A10

<400> SEQUENCE: 111
gaaattaatc ctagcaatag taatactaaa tataatgaga aattcaaaag c              51

<210> SEQ ID NO 112
<211> LENGTH: 21
<212> TYPE: DNA
<213> ORGANISM: Artificial Sequence
<220> FEATURE:
<223> OTHER INFORMATION: DNA sequence of heavy chain CDR3 of monoclonal
      antibody 180C 8A10

<400> SEQUENCE: 112
tacgatggtg gccacgactc c                                              21

<210> SEQ ID NO 113
<211> LENGTH: 379
<212> TYPE: DNA
<213> ORGANISM: Artificial Sequence
<220> FEATURE:
<223> OTHER INFORMATION: DNA sequence of light chain of monoclonal
      antibody 180C 8A10

<400> SEQUENCE: 113
atggagtttc atactcaggt ctttgtattc gtgtttctct ggttgtctgg tgttgatgga     60
gacattgtga tgacccagtc tcaaaaattc atgtccacaa cattaggaga cagggtcagc    120
atcatctcaa ggccagtcag aatgtgggta ctgctgtcgc ctggtatcaa cagaaaccag    180
gacaatctcc taaactactg atttactcaa catccaatcg ctacactgga gtccctgatc    240
gcttcacagg cagtgatctg ggacagattt cagtctcacc attagcagtg tgcagtctga    300
ggacctggca gattatttct gtcaccaata tagcagctat ctatacacgt tcggggggg     360 gaccaggctg gaaattaaa                                                 379

<210> SEQ ID NO 114
<211> LENGTH: 33
<212> TYPE: DNA
<213> ORGANISM: Artificial Sequence
<220> FEATURE:
<223> OTHER INFORMATION: DNA sequence of light chain CDR1 of monoclonal
      antibody 180C 8A10

<400> SEQUENCE: 114
aaggccagtc agaatgtggg tactgctgtc gcc                                 33

<210> SEQ ID NO 115
<211> LENGTH: 21
<212> TYPE: DNA
<213> ORGANISM: Artificial Sequence
<220> FEATURE:
<223> OTHER INFORMATION: DNA sequence of light chain CDR2 of monoclonal
      antibody 180C 8A10

<400> SEQUENCE: 115
tcaacatcca atcgctacac t                                              21

<210> SEQ ID NO 116
<211> LENGTH: 27
<212> TYPE: DNA
<213> ORGANISM: Artificial Sequence
<220> FEATURE:
<223> OTHER INFORMATION: DNA sequence of light chain CDR3 of monoclonal
      antibody 180C 8A10

<400> SEQUENCE: 116
caccaatata gcagctatct atacacg                                        27

```
<210> SEQ ID NO 117
<211> LENGTH: 115
<212> TYPE: PRT
<213> ORGANISM: Artificial Sequence
<220> FEATURE:
<223> OTHER INFORMATION: Amino acid sequence of heavy chain variable
      region of monoclonal antibody 180C 8A10

<400> SEQUENCE: 117

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Ile Asn Trp Val Lys Gln Arg Pro Gly Gln Gly Leu Glu Trp Leu
        35                  40                  45

Gly Glu Ile Asn Pro Ser Asn Ser Asn Thr Lys Tyr Asn Glu Lys Phe
    50                  55                  60

Lys Ser Arg Ala Thr Leu Thr Ala Asp Lys Ser Ser Ser Thr Ala Tyr
65                  70                  75                  80

Met Gln Leu His Ser Leu Thr Ser Glu Asp Ser Ala Val Tyr Tyr Cys
                85                  90                  95

Asn Tyr Tyr Asp Gly Gly His Asp Ser Trp Gly Gln Thr Thr Leu Thr
            100                 105                 110

Val Ser Ser
        115

<210> SEQ ID NO 118
<211> LENGTH: 107
<212> TYPE: PRT
<213> ORGANISM: Artificial Sequence
<220> FEATURE:
<223> OTHER INFORMATION: Amino acid sequence of light chain variable
      region of monoclonal antibody 180C 8A10

<400> SEQUENCE: 118

Asp Ile Val Met Thr Gln Ser Gln Lys Phe Met Ser Thr Thr Leu Gly
1               5                   10                  15

Asp Arg Val Ser Ile Ile Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Thr Ser Asn Arg Tyr Thr Gly Val Pro Asp Arg Phe Thr Gly
    50                  55                  60

Ser Gly Ser Gly Thr Asp Phe Ser Leu Thr Ile Ser Ser Val Gln Ser
65                  70                  75                  80

Glu Asp Leu Ala Asp Tyr Phe Cys His Gln Tyr Ser Ser Tyr Leu Tyr
                85                  90                  95

Thr Phe Gly Gly Gly Thr Arg Leu Glu Ile Lys
            100                 105

<210> SEQ ID NO 119
<211> LENGTH: 345
<212> TYPE: DNA
<213> ORGANISM: Artificial Sequence
<220> FEATURE:
<223> OTHER INFORMATION: DNA sequence of heavy chain variable region of
      monoclonal antibody 180C 8A10
```

<400> SEQUENCE: 119

```
caggtccaac tgcagcagcc tggggctgag cttgtgaagc ctggggcttc agtgaagttg      60
tcctgcaagg ttctggctac accttcacca actactggat aaactgggtg aaacagaggc    120
ctgggcaagg ccttgagtgg cttggagaaa ttaatcctag caatagtaat actaaatata   180
atgagaaatt caaaagcggg ccacactgac tgcagacaaa tcctccagca cagcctacat   240
gcaactccac agcctaacct ctgaggactc tgcggtctac tactgtaatt attacgatgg   300
tggccacgac tcctggggcc aggaccact ctcacagtct cctca                    345
```

<210> SEQ ID NO 120
<211> LENGTH: 319
<212> TYPE: DNA
<213> ORGANISM: Artificial sequence
<220> FEATURE:
<223> OTHER INFORMATION: DNA sequence of light chain variable region of monoclonal antibody 180C 8A10

<400> SEQUENCE: 120

```
gacattgtga tgacccagtc tcaaaaattc atgtccacaa cattaggaga cagggtcagc     60
atcatctcaa ggccagtcag aatgtgggta ctgctgtcgc ctggtatcaa cagaaaccag   120
gacaatctcc taaactactg atttactcaa catccaatcg ctacactgga gtccctgatc   180
gcttcacagg cagtgatctg ggacagattt cagtctcacc attagcagtg tgcagtctga   240
ggacctggca gattatttct gtcaccaata tagcagctat ctatacacgt tcggggggg    300
gaccaggctg gaaattaaa                                                 319
```

<210> SEQ ID NO 121
<211> LENGTH: 133
<212> TYPE: PRT
<213> ORGANISM: Artificial Sequence
<220> FEATURE:
<223> OTHER INFORMATION: Amino acid sequence for heavy chain of monoclonal antibody 180C 9D5

<400> SEQUENCE: 121

Met Gly Trp Asn Tyr Ile Phe Leu Phe Leu Ile Ala Thr Val Thr Asp
1               5                   10                  15

Val His Ser Gln Val Arg Leu Gln Gln Pro Gly Thr Asp Leu Val Lys
            20                  25                  30

Pro Gly Ala Ser Val Lys Leu Ser Cys Arg Ala Ser Gly Phe Thr Phe
        35                  40                  45

Thr Asn Tyr Trp Met Asn Trp Val Lys Gln Arg Pro Gly Gln Gly Leu
    50                  55                  60

Glu Trp Ile Gly Glu Ile Asn Thr Asn Gly Thr Lys Tyr Asn Glu
65                  70                  75                  80

Asn Phe Lys Asn Lys Ala Thr Leu Thr Val Asp Gln Ser Ser Ser Thr
                85                  90                  95

Ala Tyr Ile Gln Leu Ser Gly Leu Thr Ser Glu Asp Ser Ala Val Tyr
            100                 105                 110

Phe Cys Asn Tyr Phe Asp Gly Asn Tyr Asp Tyr Trp Gly Gln Gly Thr
        115                 120                 125

Leu Thr Val Ser Ser
    130

<210> SEQ ID NO 122
<211> LENGTH: 5

```
<212> TYPE: PRT
<213> ORGANISM: Artificial Sequence
<220> FEATURE:
<223> OTHER INFORMATION: Amino acid sequence for heavy chain CDR1 of
      monoclonal antibody 180C 9D5

<400> SEQUENCE: 122

Asn Tyr Trp Met Asn
1               5

<210> SEQ ID NO 123
<211> LENGTH: 16
<212> TYPE: PRT
<213> ORGANISM: Artificial Sequence
<220> FEATURE:
<223> OTHER INFORMATION: Amino acid sequence for heavy chain CDR2 of
      monoclonal antibody 180C 9D5

<400> SEQUENCE: 123

Glu Ile Asn Thr Asn Gly Gly Thr Lys Tyr Asn Glu Asn Phe Lys Asn
1               5                   10                  15

<210> SEQ ID NO 124
<211> LENGTH: 7
<212> TYPE: PRT
<213> ORGANISM: Artificial Sequence
<220> FEATURE:
<223> OTHER INFORMATION: Amino acid sequence for heavy chain CDR3 of
      monoclonal antibody 180C 9D5

<400> SEQUENCE: 124

Phe Asp Gly Asn Tyr Asp Tyr
1               5

<210> SEQ ID NO 125
<211> LENGTH: 127
<212> TYPE: PRT
<213> ORGANISM: Artificial Sequence
<220> FEATURE:
<223> OTHER INFORMATION: Amino acid sequence for light chain of
      monoclonal antibody 180C 9D5

<400> SEQUENCE: 125

Met Glu Phe His Thr Gln Val Phe Val Phe Val Leu Trp Leu Ser
1               5                   10                  15

Gly Val Asp Gly Asp Ile Val Met Thr Gln Ser Gln Lys Phe Met Ser
                20                  25                  30

Thr Pro Val Gly Asp Arg Val Ser Leu Thr Cys Arg Ala Ser Gln Asn
            35                  40                  45

Val Gly Thr Ala Val Ala Trp Tyr Gln Gln Lys Pro Gly Gln Pro Pro
        50                  55                  60

Lys Leu Leu Ile Tyr Ser Thr Ser Asn Arg Phe Thr Gly Val Pro Ser
65                  70                  75                  80

Arg Phe Thr Gly Ser Gly Ser Gly Thr Asp Phe Thr Leu Thr Ile Thr
                85                  90                  95

Asn Met Gln Ser Glu Asp Leu Ala Asp Tyr Phe Cys His Gln Tyr Ser
            100                 105                 110

Ser Tyr Pro Tyr Thr Phe Gly Gly Gly Thr Lys Leu Glu Ile Lys
        115                 120                 125

<210> SEQ ID NO 126
<211> LENGTH: 11
<212> TYPE: PRT
<213> ORGANISM: Artificial Sequence
```

```
<220> FEATURE:
<223> OTHER INFORMATION: Amino acid sequence for light chain CDR1 of
      monoclonal antibody 180C 9D5

<400> SEQUENCE: 126

Arg Ala Ser Gln Asn Val Gly Thr Ala Val Ala
1               5                   10

<210> SEQ ID NO 127
<211> LENGTH: 7
<212> TYPE: PRT
<213> ORGANISM: Artificial Sequence
<220> FEATURE:
<223> OTHER INFORMATION: Amino acid sequence for light chain CDR2 of
      monoclonal antibody 180C 9D5

<400> SEQUENCE: 127

Ser Thr Ser Asn Arg Phe Thr
1               5

<210> SEQ ID NO 128
<211> LENGTH: 9
<212> TYPE: PRT
<213> ORGANISM: Artificial Sequence
<220> FEATURE:
<223> OTHER INFORMATION: Amino acid sequence for light chain CDR3 of
      monoclonal antibody 180C 9D5

<400> SEQUENCE: 128

His Gln Tyr Ser Ser Tyr Pro Tyr Thr
1               5

<210> SEQ ID NO 129
<211> LENGTH: 399
<212> TYPE: DNA
<213> ORGANISM: Artificial Sequence
<220> FEATURE:
<223> OTHER INFORMATION: DNA sequence for heavy chain of monoclonal
      antibody 180C 9D5

<400> SEQUENCE: 129
atgggatgga actatatctt cctctttttg atagcaacag ttacagatgt ccactcccag      60
gtccgactgc agcagcctgg gactgatctt gtgaagcctg ggcttcagt gaagctgtcc      120 tgcagggttc tggcttcaca ttcaccaatt attggatgaa ttgggtgaaa cagaggcctg     180
gacaaggcct tgagtggatt ggagagatta ataccaacgg tggtactaag tacaatgaga     240
atttcaagaa taagccacac tgactgtgga ccaatcctcc agcacagcct acattcaact     300
cagcggcctg acatctgagg actctgcggt ctatttctgt aattacttcg atggtaacta     360
cgactactgg ggccaaggca cactctcaca gtctcctca                            399

<210> SEQ ID NO 130
<211> LENGTH: 15
<212> TYPE: DNA
<213> ORGANISM: Artificial Sequence
<220> FEATURE:
<223> OTHER INFORMATION: DNA sequence for heavy chain CDR1 of monoclonal
      antibody 180C 9D5

<400> SEQUENCE: 130
aattattgga tgaat                                                       15

<210> SEQ ID NO 131
<211> LENGTH: 48
<212> TYPE: DNA
```

```
<213> ORGANISM: Artificial Sequence
<220> FEATURE:
<223> OTHER INFORMATION: DNA sequence for heavy chain CDR2 of monoclonal
      antibody 180C 9D5

<400> SEQUENCE: 131
gagattaata ccaacggtgg tactaagtac aatgagaatt tcaagaat                    48

<210> SEQ ID NO 132
<211> LENGTH: 21
<212> TYPE: DNA
<213> ORGANISM: Artificial Sequence
<220> FEATURE:
<223> OTHER INFORMATION: DNA sequence for heavy chain CDR3 of monoclonal
      antibody 180C 9D5

<400> SEQUENCE: 132
ttcgatggta actacgacta c                                                 21

<210> SEQ ID NO 133
<211> LENGTH: 379
<212> TYPE: DNA
<213> ORGANISM: Artificial Sequence
<220> FEATURE:
<223> OTHER INFORMATION: DNA sequence for light chain of monoclonal
      antibody 180C 9D5

<400> SEQUENCE: 133
atggagtttc atactcaggt ctttgtattc gtgtttctct ggttgtctgg tgttgatgga       60
gacattgtga tgacccagtc tcaaaaattc atgtccacac cagtgggaga cagggtcagc     120
ctcacctcag ggccagtcag aatgtgggta ctgctgtagc ctggtatcaa cagaaaccag     180
gacaacctcc taaattacta atttattcaa catccaatcg attcactgga gtccctagtc     240
gcttcacagg cagtgatctg ggacagattt tactctcacc attaccaata tgcagtctga     300
agacctggca gattatttct gtcaccaata tagcagctat ccgtacacat tcggaggggg     360
gaccaaactg gaaataaaa                                                  379

<210> SEQ ID NO 134
<211> LENGTH: 33
<212> TYPE: DNA
<213> ORGANISM: Artificial Sequence
<220> FEATURE:
<223> OTHER INFORMATION: DNA sequence for light chain CDR1 of monoclonal
      antibody 180C 9D5

<400> SEQUENCE: 134
agggccagtc agaatgtggg tactgctgta gcc                                    33

<210> SEQ ID NO 135
<211> LENGTH: 21
<212> TYPE: DNA
<213> ORGANISM: Artificial Sequence
<220> FEATURE:
<223> OTHER INFORMATION: DNA sequence for light chain CDR2 of monoclonal
      antibody 180C 9D5

<400> SEQUENCE: 135
tcaacatcca atcgattcac t                                                 21

<210> SEQ ID NO 136
<211> LENGTH: 27
<212> TYPE: DNA
<213> ORGANISM: Artificial Sequence
<220> FEATURE:
```

<223> OTHER INFORMATION: DNA sequence for light chain CDR3 of monoclonal
      antibody 180C 9D5

<400> SEQUENCE: 136
caccaatata gcagctatcc gtacaca                                          27

<210> SEQ ID NO 137
<211> LENGTH: 114
<212> TYPE: PRT
<213> ORGANISM: Artificial Sequence
<220> FEATURE:
<223> OTHER INFORMATION: Amino acid sequence for heavy chain variable
      region of monoclonal antibody 180C 9D5

<400> SEQUENCE: 137

Gln Val Arg Leu Gln Gln Pro Gly Thr Asp Leu Val Lys Pro Gly Ala
1               5                   10                  15

Ser Val Lys Leu Ser Cys Arg Ala Ser Gly Phe Thr Phe Thr Asn Tyr
            20                  25                  30

Trp Met Asn Trp Val Lys Gln Arg Pro Gly Gln Gly Leu Glu Trp Ile
        35                  40                  45

Gly Glu Ile Asn Thr Asn Gly Gly Thr Lys Tyr Asn Glu Asn Phe Lys
50                  55                  60

Asn Lys Ala Thr Leu Thr Val Asp Gln Ser Ser Ser Thr Ala Tyr Ile
65                  70                  75                  80

Gln Leu Ser Gly Leu Thr Ser Glu Asp Ser Ala Val Tyr Phe Cys Asn
                85                  90                  95

Tyr Phe Asp Gly Asn Tyr Asp Tyr Trp Gly Gln Gly Thr Leu Thr Val
            100                 105                 110

Ser Ser

<210> SEQ ID NO 138
<211> LENGTH: 107
<212> TYPE: PRT
<213> ORGANISM: Artificial Sequence
<220> FEATURE:
<223> OTHER INFORMATION: Amino acid sequence for light chain variable
      region of monoclonal antibody 180C 9D5

<400> SEQUENCE: 138

Asp Ile Val Met Thr Gln Ser Gln Lys Phe Met Ser Thr Pro Val Gly
1               5                   10                  15

Asp Arg Val Ser Leu Thr Cys Arg Ala Ser Gln Asn Val Gly Thr Ala
            20                  25                  30

Val Ala Trp Tyr Gln Gln Lys Pro Gly Gln Pro Pro Lys Leu Leu Ile
        35                  40                  45

Tyr Ser Thr Ser Asn Arg Phe Thr Gly Val Pro Ser Arg Phe Thr Gly
50                  55                  60

Ser Gly Ser Gly Thr Asp Phe Thr Leu Thr Ile Thr Asn Met Gln Ser
65                  70                  75                  80

Glu Asp Leu Ala Asp Tyr Phe Cys His Gln Tyr Ser Ser Tyr Pro Tyr
                85                  90                  95

Thr Phe Gly Gly Gly Thr Lys Leu Glu Ile Lys
            100                 105

<210> SEQ ID NO 139
<211> LENGTH: 342
<212> TYPE: DNA
<213> ORGANISM: Artificial Sequence
<220> FEATURE:

```
<223> OTHER INFORMATION: DNA sequence for heavy chain variable region of
      monoclonal antibody 180C 9D5

<400> SEQUENCE: 139
caggtccgac tgcagcagcc tgggactgat cttgtgaagc tggggcttc agtgaagctg      60 tcctgcaggg ttctggcttc acattcacca attattggat gaattgggtg aaacagaggc    120
ctggacaagg ccttgagtgg attggagaga ttaataccaa cggtggtact aagtacaatg    180
agaatttcaa gaataagcca cactgactgt ggaccaatcc tccagcacag cctacattca    240
actcagcggc ctgacatctg aggactctgc ggtctatttc tgtaattact cgatggtaa    300 ctacgactac tggggccaag gcacactctc acagtctcct ca                       342

<210> SEQ ID NO 140
<211> LENGTH: 319
<212> TYPE: DNA
<213> ORGANISM: Artificial Sequence
<220> FEATURE:
<223> OTHER INFORMATION: DNA sequence for light chain variable region of
      monoclonal antibody 180C 9D5

<400> SEQUENCE: 140
gacattgtga tgacccagtc tcaaaaattc atgtccacac cagtgggaga cagggtcagc     60
ctcacctcag ggccagtcag aatgtgggta ctgctgtagc ctggtatcaa cagaaaccag    120
gacaacctcc taaattacta atttattcaa catccaatcg attcactgga gtccctagtc    180
gcttcacagg cagtgatctg ggacagattt tactctcacc attaccaata tgcagtctga    240
agacctggca gattatttct gtcaccaata tagcagctat ccgtacacat tcggaggggg    300
gaccaaactg gaaataaaa                                                 319

<210> SEQ ID NO 141
<211> LENGTH: 137
<212> TYPE: PRT
<213> ORGANISM: Artificial Sequence
<220> FEATURE:
<223> OTHER INFORMATION: Amino acid sequence of heavy chain of
      monoclonal antibody 180C 9G8

<400> SEQUENCE: 141

Met Tyr Leu Gly Leu Asn Cys Val Ile Ile Val Phe Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asp Trp Val Arg Gln Ser Pro Glu Lys Gly Leu
    50                  55                  60

Glu Trp Val Ala Glu Ile Arg Asn Lys Ala Asn Asn His Ala Thr Tyr
65                  70                  75                  80

Tyr Ala Glu Ser Val Lys Gly Arg Phe Thr Ile Ser Arg Asp Asp Ser
                85                  90                  95

Asn Ser Arg Met Phe Leu Gln Met Asp Ser Leu Arg Ala Glu Asp Thr
            100                 105                 110

Gly Ile Tyr Tyr Cys Ile Gly Gly Ile Pro Arg Tyr Phe Asp Val Gly
        115                 120                 125

Ala Gly Thr Thr Val Thr Val Ser Ser
    130                 135
```

```
<210> SEQ ID NO 142
<211> LENGTH: 5
<212> TYPE: PRT
<213> ORGANISM: Artificial Sequence
<220> FEATURE:
<223> OTHER INFORMATION: Amino acid sequence of heavy chain CDR1 of
      monoclonal antibody 180C 9G8

<400> SEQUENCE: 142

Asp Ala Trp Met Asp
1               5

<210> SEQ ID NO 143
<211> LENGTH: 19
<212> TYPE: PRT
<213> ORGANISM: Artificial Sequence
<220> FEATURE:
<223> OTHER INFORMATION: Amino acid sequence of heavy chain CDR2 of
      monoclonal antibody 180C 9G8

<400> SEQUENCE: 143

Glu Ile Arg Asn Lys Ala Asn Asn His Ala Thr Tyr Tyr Ala Glu Ser
1               5                   10                  15

Val Lys Gly

<210> SEQ ID NO 144
<211> LENGTH: 8
<212> TYPE: PRT
<213> ORGANISM: Artificial Sequence
<220> FEATURE:
<223> OTHER INFORMATION: Amino acid sequence of heavy chain CDR3 of
      monoclonal antibody 180C 9G8

<400> SEQUENCE: 144

Gly Ile Pro Arg Tyr Phe Asp Val
1               5

<210> SEQ ID NO 145
<211> LENGTH: 127
<212> TYPE: PRT
<213> ORGANISM: Artificial Sequence
<220> FEATURE:
<223> OTHER INFORMATION: Amino acid sequence of light chain of
      monoclonal antibody 180C 9G8

<400> SEQUENCE: 145

Met Glu Ser Gln Thr Gln Val Phe Val Tyr Met Leu Leu Trp Leu Ser
1               5                   10                  15

Gly Val Asp Gly Asp Ile Val Met Thr Gln Ser Gln Lys Phe Met Ser
                20                  25                  30

Thr Ser Val Gly Asp Arg Val Ser Ile Thr Cys Lys Ala Ser Gln Asn
            35                  40                  45

Val Arg Thr Tyr Val Ala Trp Tyr Gln Gln Lys Pro Gly Gln Ser Pro
        50                  55                  60

Lys Ala Leu Leu Tyr Ser Ala Ser Tyr Arg Tyr Ser Gly Val Pro Asp
65                  70                  75                  80

Arg Phe Ile Gly Ser Gly Ser Gly Thr Gln Phe Thr Leu Thr Ile Ser
                85                  90                  95

Asp Val Gln Ser Glu Asp Leu Ala Glu Tyr Phe Cys His Gln Tyr Asn
            100                 105                 110

Ser Tyr Pro Leu Thr Phe Gly Gly Gly Thr Lys Leu Glu Ile Gln
        115                 120                 125
```

```
<210> SEQ ID NO 146
<211> LENGTH: 11
<212> TYPE: PRT
<213> ORGANISM: Artificial Sequence
<220> FEATURE:
<223> OTHER INFORMATION: Amino acid sequence of light chain CDR1 of
      monoclonal antibody 180C 9G8

<400> SEQUENCE: 146

Lys Ala Ser Gln Asn Val Arg Thr Tyr Val Ala
1               5                   10

<210> SEQ ID NO 147
<211> LENGTH: 7
<212> TYPE: PRT
<213> ORGANISM: Artificial sequence
<220> FEATURE:
<223> OTHER INFORMATION: Amino acid sequence of light chain CDR2 of
      monoclonal antibody 180C 9G8

<400> SEQUENCE: 147

Ser Ala Ser Tyr Arg Tyr Ser
1               5

<210> SEQ ID NO 148
<211> LENGTH: 9
<212> TYPE: PRT
<213> ORGANISM: Artificial Sequence
<220> FEATURE:
<223> OTHER INFORMATION: Amino acid sequence of light chain CDR3 of
      monoclonal antibody 180C 9G8

<400> SEQUENCE: 148

His Gln Tyr Asn Ser Tyr Pro Leu Thr
1               5

<210> SEQ ID NO 149
<211> LENGTH: 411
<212> TYPE: DNA
<213> ORGANISM: Artificial Sequence
<220> FEATURE:
<223> OTHER INFORMATION: DNA sequence of heavy chain of monoclonal
      antibody 180C 9G8

<400> SEQUENCE: 149
atgtacttgg gactgaactg tgtaatcata gtttttctct taaaaggtgt ccagagtgaa      60
gtgaagcttg aggagtctgg aggaggcttg gtgcaacctg gaggatccat gaaactctct    120
tgtgctgttc tggattcact tttagtgatg cctggatgga ctgggtccgc cagtctccag    180
agaaggggct tgagtgggtt gctgaaatta gaaacaaagc taataatcat gcaacatatt    240
atgctgagtc tgtgagggga ggttcaccat ctcaagagat gattccaaca gtagaatgtt    300
cctgcaaatg gacagtttaa gagctgaaga cactggcatt tattactgta tcggggggaat    360 tccacgctac ttcgatgtct gggcgcaggg accacggtca ccgtctcctc a              411

<210> SEQ ID NO 150
<211> LENGTH: 15
<212> TYPE: DNA
<213> ORGANISM: Artificial Sequence
<220> FEATURE:
<223> OTHER INFORMATION: DNA sequence of heavy chain CDR1 of monoclonal
      antibody 180C 9G8

<400> SEQUENCE: 150
gatgcctgga tggac                                                       15
```

<210> SEQ ID NO 151
<211> LENGTH: 56
<212> TYPE: DNA
<213> ORGANISM: Artificial Sequence
<220> FEATURE:
<223> OTHER INFORMATION: DNA sequence of heavy chain CDR2 of monoclonal
    antibody 180C 9G8

<400> SEQUENCE: 151
gaaattagaa acaaagctaa taatcatgca acatattatg ctgagtctgt gagggg       56

<210> SEQ ID NO 152
<211> LENGTH: 24
<212> TYPE: DNA
<213> ORGANISM: Artificial Sequence
<220> FEATURE:
<223> OTHER INFORMATION: DNA sequence of heavy chain CDR3 of monoclonal
    antibody 180C 9G8

<400> SEQUENCE: 152
ggaattccac gctacttcga tgtc                                          24

<210> SEQ ID NO 153
<211> LENGTH: 379
<212> TYPE: DNA
<213> ORGANISM: Artificial Sequence
<220> FEATURE:
<223> OTHER INFORMATION: DNA sequence of light chain of monoclonal
    antibody 180C 9G8

<400> SEQUENCE: 153
atggagtcac agactcaggt ctttgtatac atgttgctgt ggttgtctgg tgttgatgga    60
gacattgtga tgacccagtc tcaaaaattc atgtccacat cagtcggaga cagggtcagc   120
attacctcaa ggccagtcag aatgtgagaa cttatgttgc ctggtatcaa cagaaaccag   180
gacaatcccc taaagcactg ctttattcgg cttcttaccg atacagtgga gtccctgatc   240
gcttcatagg cagtgatctg ggacacaatt cactctcacc atcagcgatg tgcagtctga   300
agacttggca gaatatttct gtcaccaata taacagctat cctctaacgt tcggaggggg   360
gaccaaactg gaaatacaa                                                379

<210> SEQ ID NO 154
<211> LENGTH: 33
<212> TYPE: DNA
<213> ORGANISM: Artificial Sequence
<220> FEATURE:
<223> OTHER INFORMATION: DNA sequence of light chain CDR1 of monoclonal
    antibody 180C 9G8

<400> SEQUENCE: 154
aaggccagtc agaatgtgag aacttatgtt gcc                                33

<210> SEQ ID NO 155
<211> LENGTH: 21
<212> TYPE: DNA
<213> ORGANISM: Artificial Sequence
<220> FEATURE:
<223> OTHER INFORMATION: DNA sequence of light chain CDR2 of monoclonal
    antibody 180C 9G8

<400> SEQUENCE: 155
tcggcttctt accgatacag t                                             21

<210> SEQ ID NO 156

```
<211> LENGTH: 27
<212> TYPE: DNA
<213> ORGANISM: Artificial Sequence
<220> FEATURE:
<223> OTHER INFORMATION: DNA sequence of light chain CDR3 of monoclonal
      antibody 180C 9G8

<400> SEQUENCE: 156
caccaatata acagctatcc tctaacg                                          27

<210> SEQ ID NO 157
<211> LENGTH: 118
<212> TYPE: PRT
<213> ORGANISM: Artificial Sequence
<220> FEATURE:
<223> OTHER INFORMATION: Amino acid sequence of heavy chain variable
      region of monoclonal antibody 180C 9G8

<400> SEQUENCE: 157

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Asn Lys Ala Asn Asn His Ala Thr Tyr Tyr Ala Glu
    50                  55                  60

Ser Val Lys Gly Arg Phe Thr Ile Ser Arg Asp Asp Ser Asn Ser Arg
65                  70                  75                  80

Met Phe Leu Gln Met Asp Ser Leu Arg Ala Glu Asp Thr Gly Ile Tyr
                85                  90                  95

Tyr Cys Ile Gly Gly Ile Pro Arg Tyr Phe Asp Val Gly Ala Gly Thr
            100                 105                 110

Thr Val Thr Val Ser Ser
        115

<210> SEQ ID NO 158
<211> LENGTH: 107
<212> TYPE: PRT
<213> ORGANISM: Artificial Sequence
<220> FEATURE:
<223> OTHER INFORMATION: Amino acid sequence of light chain variable
      region of monoclonal antibody 180C 9G8

<400> SEQUENCE: 158

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Tyr
            20                  25                  30

Val Ala Trp Tyr Gln Gln Lys Pro Gly Gln Ser Pro Lys Ala Leu Leu
        35                  40                  45

Tyr Ser Ala Ser Tyr Arg Tyr Ser Gly Val Pro Asp Arg Phe Ile Gly
    50                  55                  60

Ser Gly Ser Gly Thr Gln Phe Thr Leu Thr Ile Ser Asp Val Gln Ser
65                  70                  75                  80

Glu Asp Leu Ala Glu Tyr Phe Cys His Gln Tyr Asn Ser Tyr Pro Leu
                85                  90                  95

Thr Phe Gly Gly Gly Thr Lys Leu Glu Ile Gln
            100                 105
```

<210> SEQ ID NO 159
<211> LENGTH: 354
<212> TYPE: DNA
<213> ORGANISM: Artificial Sequence
<220> FEATURE:
<223> OTHER INFORMATION: DNA sequence of heavy chain variable region of
      monoclonal antibody 180C 9G8

<400> SEQUENCE: 159

```
gaagtgaagc ttgaggagtc tggaggaggc ttggtgcaac ctggaggatc catgaaactc      60
tcttgtgctg ttctggattc acttttagtg atgcctggat ggactgggtc cgccagtctc     120
cagagaaggg gcttgagtgg gttgctgaaa ttagaaacaa agctaataat catgcaacat     180
attatgctga gtctgtgagg ggaggttcac catctcaaga gatgattcca acagtagaat     240
gttcctgcaa atggacagtt aagagctgaa agacactggc atttattact gtatcggggg     300
aattccacgc tacttcgatg tctgggcgca gggaccacgg tcaccgtctc ctca           354
```

<210> SEQ ID NO 160
<211> LENGTH: 319
<212> TYPE: DNA
<213> ORGANISM: Artificial Sequence
<220> FEATURE:
<223> OTHER INFORMATION: DNA sequence of light chain variable region of
      monoclonal antibody 180C 9G8

<400> SEQUENCE: 160

```
gacattgtga tgacccagtc tcaaaaattc atgtccacat cagtcggaga cagggtcagc      60
attacctcaa ggccagtcag aatgtgagaa cttatgttgc ctggtatcaa cagaaaccag     120
gacaatcccc taaagcactg ctttattcgg cttcttaccg atacagtgga gtccctgatc     180
gcttcatagg cagtgatctg gacacaatt cactctcacc atcagcgatg tgcagtctga     240
agacttggca gaatatttct gtcaccaata taacagctat cctctaacgt tcggaggggg     300
gaccaaactg gaaatacaa                                                   319
```

<210> SEQ ID NO 161
<211> LENGTH: 136
<212> TYPE: PRT
<213> ORGANISM: Artificial Sequence
<220> FEATURE:
<223> OTHER INFORMATION: Amino acid sequence of heavy chain of
      monoclonal antibody 179B 9G1.1

<400> SEQUENCE: 161

```
Met Glu Trp Pro Cys Ile Phe Leu Phe Leu Leu Ser Val Thr Glu Gly
1               5                   10                  15

Val His Ser Gln Val Gln Leu Gln Gln Ser Gly Pro Glu Leu Val Lys
            20                  25                  30

Pro Gly Ala Ser Val Met Ile Ser Cys Lys Val Phe Gly Asp Ile Phe
        35                  40                  45

Ser Ser Ser Trp Met Asn Trp Val Lys Gln Arg Pro Gly Lys Gly Leu
    50                  55                  60

Glu Trp Ile Gly Trp Ile Cys Pro Gly Asn Gly Ala Thr Lys Tyr Asn
65                  70                  75                  80

Gly Lys Phe Lys Gly Lys Ala Thr Leu Thr Ala Asp Lys Ser Ser Gly
                85                  90                  95

Thr Gly Tyr Met Gln Leu Ser Ser Leu Thr Ser Glu Asp Ser Ala Val
            100                 105                 110

Tyr Phe Cys Glu Leu Gly Arg Arg Asp Gly Tyr Leu Asp Val Trp Ala
        115                 120                 125
```

```
Gly Thr Thr Val Thr Val Ser Ser
    130                 135
```

<210> SEQ ID NO 162
<211> LENGTH: 5
<212> TYPE: PRT
<213> ORGANISM: Artificial Sequence
<220> FEATURE:
<223> OTHER INFORMATION: Amino acid sequence of heavy chain CDR1 of
      monoclonal antibody 179B 9G1.1

<400> SEQUENCE: 162

```
Ser Ser Trp Met Asn
1               5
```

<210> SEQ ID NO 163
<211> LENGTH: 17
<212> TYPE: PRT
<213> ORGANISM: Artificial Sequence
<220> FEATURE:
<223> OTHER INFORMATION: Amino acid sequence of heavy chain CDR2 of
      monoclonal antibody 179B 9G1.1

<400> SEQUENCE: 163

```
Trp Ile Cys Pro Gly Asn Gly Ala Thr Lys Tyr Asn Gly Lys Phe Lys
1               5                   10                  15
Gly
```

<210> SEQ ID NO 164
<211> LENGTH: 9
<212> TYPE: PRT
<213> ORGANISM: Artificial Sequence
<220> FEATURE:
<223> OTHER INFORMATION: Amino acid sequence of heavy chain CDR3 of
      monoclonal antibody 179B 9G1.1

<400> SEQUENCE: 164

```
Gly Arg Arg Asp Gly Tyr Leu Asp Val
1               5
```

<210> SEQ ID NO 165
<211> LENGTH: 127
<212> TYPE: PRT
<213> ORGANISM: Artificial Sequence
<220> FEATURE:
<223> OTHER INFORMATION: Amino acid sequence of light chain of
      monoclonal antibody 179B 9G1.1

<400> SEQUENCE: 165

```
Met Glu Ser Gln Thr Gln Val Phe Val Tyr Met Leu Leu Trp Leu Ser
1               5                   10                  15

Gly Val Asp Gly Asp Ile Val Met Thr Gln Ser Gln Lys Phe Ile Phe
            20                  25                  30

Thr Ser Glu Gly Asp Arg Val Ser Val Thr Cys Lys Ala Ser Gln Asn
        35                  40                  45

Val Gly Thr Asn Ile Ala Trp Tyr Gln Gln Lys Pro Gly Gln Ser Pro
    50                  55                  60

Lys Ala Leu Ile Tyr Ser Ala Ser Asn Arg Tyr Ser Gly Val Pro Asp
65                  70                  75                  80

Arg Phe Thr Gly Ser Gly Ser Gly Thr Asp Phe Thr Leu Thr Phe Ser
                85                  90                  95

Asn Val Gln Ser Glu Asp Leu Ala Glu Tyr Phe Cys Leu Gln Tyr Asn
            100                 105                 110
```

Asn Tyr Pro Trp Thr Phe Gly Gly Gly Thr Lys Leu Glu Ile Lys
        115                 120                 125

<210> SEQ ID NO 166
<211> LENGTH: 11
<212> TYPE: PRT
<213> ORGANISM: Artificial Sequence
<220> FEATURE:
<223> OTHER INFORMATION: Amino acid sequence of light chain CDR1 of
      monoclonal antibody 179B 9G1.1

<400> SEQUENCE: 166

Lys Ala Ser Gln Asn Val Gly Thr Asn Ile Ala
1               5                   10

<210> SEQ ID NO 167
<211> LENGTH: 7
<212> TYPE: PRT
<213> ORGANISM: Artificial Sequence
<220> FEATURE:
<223> OTHER INFORMATION: Amino acid sequence of light chain CDR2 of
      monoclonal antibody 179B 9G1.1

<400> SEQUENCE: 167

Ser Ala Ser Asn Arg Tyr Ser
1               5

<210> SEQ ID NO 168
<211> LENGTH: 9
<212> TYPE: PRT
<213> ORGANISM: Artificial Sequence
<220> FEATURE:
<223> OTHER INFORMATION: Amino acid sequence of light chain CDR3 of
      monoclonal antibody 179B 9G1.1

<400> SEQUENCE: 168

Leu Gln Tyr Asn Asn Tyr Pro Trp Thr
1               5

<210> SEQ ID NO 169
<211> LENGTH: 408
<212> TYPE: DNA
<213> ORGANISM: Artificial Sequence
<220> FEATURE:
<223> OTHER INFORMATION: DNA sequence of heavy chain of monoclonal
      antibody 179B 9G1.1

<400> SEQUENCE: 169
atggaatggc cttgtatctt tctcttcctc ctgtcagtaa ctgaaggtgt ccactcccag      60
gtccagttgc agcagtctgg acctgaactg gtgaagcctg gggcctcagt gatgatttcc    120
tgcaaagttt tggcgatata ttcagtagtt cctggatgaa ctgggtgaag cagcggcctg    180
gaaagggtct tgagtggatt ggatggattt gtcctggaaa tggtgccact aagtacaatg    240
gaaagttcaa gggcaggcca cactgactgc agataaatcc tcaggcacag gctacatgca    300
gctcagcagc ctgacatctg aggactctgc ggtctatttc tgtgaactgg gacgtcggga    360
cggttatctc gatgtctggg ggcagggaca acggtcaccg tctcctca               408

<210> SEQ ID NO 170
<211> LENGTH: 15
<212> TYPE: DNA
<213> ORGANISM: Artificial Sequence
<220> FEATURE:
<223> OTHER INFORMATION: DNA sequence of heavy chain CDR1 of monoclonal
      antibody 179B 9G1.1

```
<400> SEQUENCE: 170
agttcctgga tgaac                                                           15

<210> SEQ ID NO 171
<211> LENGTH: 51
<212> TYPE: DNA
<213> ORGANISM: Artificial Sequence
<220> FEATURE:
<223> OTHER INFORMATION: DNA sequence of heavy chain CDR2 of monoclonal
      antibody 179B 9G1.1

<400> SEQUENCE: 171
tggatttgtc ctggaaatgg tgccactaag tacaatggaa agttcaaggg c                   51

<210> SEQ ID NO 172
<211> LENGTH: 27
<212> TYPE: DNA
<213> ORGANISM: Artificial Sequence
<220> FEATURE:
<223> OTHER INFORMATION: DNA sequence of heavy chain CDR3 of monoclonal
      antibody 179B 9G1.1

<400> SEQUENCE: 172
ggacgtcggg acggttatct cgatgtc                                              27

<210> SEQ ID NO 173
<211> LENGTH: 379
<212> TYPE: DNA
<213> ORGANISM: Artificial Sequence
<220> FEATURE:
<223> OTHER INFORMATION: DNA sequence of light chain of monoclonal
      antibody 179B 9G1.1

<400> SEQUENCE: 173
atggagtcac agactcaggt ctttgtatac atgttgctgt ggttgtctgg tgttgatgga          60
gacattgtga tgacacagtc tcaaaaattc atattcacat cagaaggtga cagggtcagc         120
gtcacctcaa ggccagtcag aatgtgggta ctaatattgc ctggtatcaa cagaaaccag         180
gacaatctcc taaagcactg atttactcgg catccaaccg gtacagtgga gtccctgatc         240
gcttcacagg cagtgatctg gacagattt cactctcact ttcagcaatg tgcagtctga          300
agacttggca gaatatttct gtctgcaata taacaactat ccgtggacgt tcggtggagg         360
caccaagctg gaaatcaaa                                                     379

<210> SEQ ID NO 174
<211> LENGTH: 33
<212> TYPE: DNA
<213> ORGANISM: artificial Sequence
<220> FEATURE:
<223> OTHER INFORMATION: DNA sequence of light chain CDR1 of monoclonal
      antibody 179B 9G1.1

<400> SEQUENCE: 174
aaggccagtc agaatgtggg tactaatatt gcc                                       33

<210> SEQ ID NO 175
<211> LENGTH: 21
<212> TYPE: DNA
<213> ORGANISM: Artificial Sequence
<220> FEATURE:
<223> OTHER INFORMATION: DNA sequence of light chain CDR2 of monoclonal
      antibody 179B 9G1.1
```

-continued

<400> SEQUENCE: 175
tcggcatcca accggtacag t                                              21

<210> SEQ ID NO 176
<211> LENGTH: 27
<212> TYPE: DNA
<213> ORGANISM: Artificial Sequence
<220> FEATURE:
<223> OTHER INFORMATION: DNA sequence of light chain CDR3 of monoclonal
      antibody 179B 9G1.1

<400> SEQUENCE: 176
ctgcaatata acaactatcc gtggacg                                        27

<210> SEQ ID NO 177
<211> LENGTH: 117
<212> TYPE: PRT
<213> ORGANISM: Artificial Sequence
<220> FEATURE:
<223> OTHER INFORMATION: Amino acid sequence of heavy chain variable
      region of monoclonal antibody 179B 9G1.1

<400> SEQUENCE: 177

Gln Val Gln Leu Gln Gln Ser Gly Pro Glu Leu Val Lys Pro Gly Ala
1               5                   10                  15

Ser Val Met Ile Ser Cys Lys Val Phe Gly Asp Ile Phe Ser Ser Ser
            20                  25                  30

Trp Met Asn Trp Val Lys Gln Arg Pro Gly Lys Gly Leu Glu Trp Ile
        35                  40                  45

Gly Trp Ile Cys Pro Gly Asn Gly Ala Thr Lys Tyr Asn Gly Lys Phe
    50                  55                  60

Lys Gly Lys Ala Thr Leu Thr Ala Asp Lys Ser Ser Gly Thr Gly Tyr
65                  70                  75                  80

Met Gln Leu Ser Ser Leu Thr Ser Glu Asp Ser Ala Val Tyr Phe Cys
                85                  90                  95

Glu Leu Gly Arg Arg Asp Gly Tyr Leu Asp Val Trp Ala Gly Thr Thr
            100                 105                 110

Val Thr Val Ser Ser
        115

<210> SEQ ID NO 178
<211> LENGTH: 107
<212> TYPE: PRT
<213> ORGANISM: Artificial Sequence
<220> FEATURE:
<223> OTHER INFORMATION: Amino acid sequence of light chain variable
      region of monoclonal antibody 179B 9G1.1

<400> SEQUENCE: 178

Asp Ile Val Met Thr Gln Ser Gln Lys Phe Ile Phe Thr Ser Glu Gly
1               5                   10                  15

Asp Arg Val Ser Val Thr Cys Lys Ala Ser Gln Asn Val Gly Thr Asn
            20                  25                  30

Ile Ala Trp Tyr Gln Gln Lys Pro Gly Gln Ser Pro Lys Ala Leu Ile
        35                  40                  45

Tyr Ser Ala Ser Asn Arg Tyr Ser Gly Val Pro Asp Arg Phe Thr Gly
    50                  55                  60

Ser Gly Ser Gly Thr Asp Phe Thr Leu Thr Phe Ser Asn Val Gln Ser
65                  70                  75                  80

Glu Asp Leu Ala Glu Tyr Phe Cys Leu Gln Tyr Asn Asn Tyr Pro Trp
                85                  90                  95

Thr Phe Gly Gly Gly Thr Lys Leu Glu Ile Lys
            100                 105

<210> SEQ ID NO 179
<211> LENGTH: 351
<212> TYPE: DNA
<213> ORGANISM: Artificial Sequence
<220> FEATURE:
<223> OTHER INFORMATION: DNA sequence of heavy chain variable region of
      monoclonal antibody 179B 9G1.1

<400> SEQUENCE: 179
caggtccagt tgcagcagtc tggacctgaa ctggtgaagc ctggggcctc agtgatgatt    60
tcctgcaaag ttttggcgat atattcagta gttcctggat gaactgggtg aagcagcggc   120
ctggaaaggg tcttgagtgg attggatgga tttgtcctgg aaatggtgcc actaagtaca   180
atggaaagtt caagggcagg ccacactgac tgcagataaa tcctcaggca caggctacat   240
gcagctcagc agcctgacat ctgaggactc tgcggtctat ttctgtgaac tgggacgtcg   300
ggacggttat ctcgatgtct gggggcaggg acaacggtca ccgtctcctc a            351

<210> SEQ ID NO 180
<211> LENGTH: 319
<212> TYPE: DNA
<213> ORGANISM: Artificial Sequence
<220> FEATURE:
<223> OTHER INFORMATION: DNA sequence of light chain variable region of
      monoclonal antibody 179B 9G1.1

<400> SEQUENCE: 180
gacattgtga tgacacagtc tcaaaaattc atattcacat cagaaggtga cagggtcagc    60
gtcacctcaa ggccagtcag aatgtgggta ctaatattgc ctggtatcaa cagaaaccag   120
gacaatctcc taaagcactg atttactcgg catccaaccg gtacagtgga gtccctgatc   180
gcttcacagg cagtgatctg gacagatttc actctcact ttcagcaatg tgcagtctga    240
agacttggca gaatatttct gtctgcaata taacaactat ccgtggacgt tcggtggagg   300
caccaagctg gaaatcaaa                                                319

<210> SEQ ID NO 181
<211> LENGTH: 138
<212> TYPE: PRT
<213> ORGANISM: Artificial Sequence
<220> FEATURE:
<223> OTHER INFORMATION: Amino acid sequence of heavy chain of
      monoclonal antibody 179B 9E12

<400> SEQUENCE: 181

Met Gly Trp Ser Trp Ile Phe Leu Phe Leu Leu Ser Gly Thr Ala Gly
1               5                   10                  15

Val His Cys Gln Ile Gln Leu Gln Gln Ser Gly Pro Glu Leu Val Lys
                20                  25                  30

Pro Gly Ala Ser Val Lys Ile Ser Cys Lys Ala Ser Asp Tyr Ser Phe
            35                  40                  45

Thr Asn Ser Tyr Ile Asn Trp Val Lys Gln Arg Pro Gly Gln Gly Leu
        50                  55                  60

Glu Trp Ile Gly Trp Ile Tyr Pro Gly Ser Thr Asn Thr Lys Tyr Asn
65                  70                  75                  80

```
Glu Lys Phe Trp Asp Lys Ala Thr Leu Thr Val Asp Thr Ser Ser Asn
                85                  90                  95

Thr Ala Tyr Met Glu Leu Arg Gly Leu Thr Ser Glu Asp Ser Ala Val
            100                 105                 110

Tyr Phe Cys Glu Met Gly Thr His Tyr Ser Tyr Asp Val Met Asp Trp
        115                 120                 125

Gly Gln Gly Thr Ser Val Thr Val Ser Ser
    130                 135
```

<210> SEQ ID NO 182
<211> LENGTH: 5
<212> TYPE: PRT
<213> ORGANISM: Artificial Sequence
<220> FEATURE:
<223> OTHER INFORMATION: Amino acid sequence of heavy chain CDR1 of monoclonal antibody 179B 9E12

<400> SEQUENCE: 182

```
Asn Ser Tyr Ile Asn
1               5
```

<210> SEQ ID NO 183
<211> LENGTH: 17
<212> TYPE: PRT
<213> ORGANISM: Artificial Sequence
<220> FEATURE:
<223> OTHER INFORMATION: Amino acid sequence of heavy chain CDR2 of monoclonal antibody 179B 9E12

<400> SEQUENCE: 183

```
Trp Ile Tyr Pro Gly Ser Thr Asn Thr Lys Tyr Asn Glu Lys Phe Trp
1               5                   10                  15

Asp
```

<210> SEQ ID NO 184
<211> LENGTH: 10
<212> TYPE: PRT
<213> ORGANISM: Artificial Sequence
<220> FEATURE:
<223> OTHER INFORMATION: Amino acid sequence of heavy chain CDR3 of monoclonal antibody 179B 9E12

<400> SEQUENCE: 184

```
Gly Thr His Tyr Ser Tyr Asp Val Met Asp
1               5                   10
```

<210> SEQ ID NO 185
<211> LENGTH: 127
<212> TYPE: PRT
<213> ORGANISM: Artificial Sequence
<220> FEATURE:
<223> OTHER INFORMATION: Amino acid sequence of light chain of monoclonal antibody 179B 9E12

<400> SEQUENCE: 185

```
Met Glu Phe Gln Thr Gln Val Phe Val Phe Val Leu Leu Trp Leu Ser
1               5                   10                  15

Gly Val Asp Gly Asp Ile Val Met Thr Pro Ser Gln Lys Phe Met Ser
            20                  25                  30

Thr Ser Val Gly Asp Arg Val Ser Ile Thr Cys Lys Ala Ser Gln Asn
        35                  40                  45

Val Arg Thr Ser Val Gly Trp Tyr Gln Gln Lys Pro Gly Gln Ser Pro
    50                  55                  60
```

```
Lys Pro Leu Ile Tyr Ala Thr Ser Asn Arg His Thr Gly Val Pro Asp
 65                  70                  75                  80

Arg Phe Thr Gly Ser Gly Ser Gly Thr Asp Phe Ser Leu Thr Ile Thr
                 85                  90                  95

Asn Val Gln Ser Glu Asp Gln Ala Asp Tyr Phe Cys Leu Gln His Trp
            100                 105                 110

Asn Tyr Pro Trp Thr Phe Gly Gly Gly Thr Lys Leu Glu Ile Lys
        115                 120                 125

<210> SEQ ID NO 186
<211> LENGTH: 11
<212> TYPE: PRT
<213> ORGANISM: Artificial Sequence
<220> FEATURE:
<223> OTHER INFORMATION: Amino acid sequence of light chain CDR1 of
      monoclonal antibody 179B 9E12

<400> SEQUENCE: 186

Lys Ala Ser Gln Asn Val Arg Thr Ser Val Gly
 1               5                  10

<210> SEQ ID NO 187
<211> LENGTH: 7
<212> TYPE: PRT
<213> ORGANISM: Artificial Sequence
<220> FEATURE:
<223> OTHER INFORMATION: Amino acid sequence of light chain CDR2 of
      monoclonal antibody 179B 9E12

<400> SEQUENCE: 187

Ala Thr Ser Asn Arg His Thr
 1               5

<210> SEQ ID NO 188
<211> LENGTH: 9
<212> TYPE: PRT
<213> ORGANISM: Artificial Sequence
<220> FEATURE:
<223> OTHER INFORMATION: Amino acid sequence of light chain CDR3 of
      monoclonal antibody 179B 9E12

<400> SEQUENCE: 188

Leu Gln His Trp Asn Tyr Pro Trp Thr
 1               5

<210> SEQ ID NO 189
<211> LENGTH: 414
<212> TYPE: DNA
<213> ORGANISM: Artificial Sequence
<220> FEATURE:
<223> OTHER INFORMATION: DNA sequence of heavy chain of monoclonal
      antibody 179 9E12

<400> SEQUENCE: 189
atgggatgga gctggatctt tcttttcctc ctgtcaggaa ctgcaggtgt ccattgccag        60
atccagctgc agcagtctgg acctgagttg gtgaagcctg ggcttcagt gaagatatcc       120 tgcaaggttc tgactacagc ttcactaact cctatataaa ctgggtgaag cagaggcctg       180
gacagggact tgagtggatt ggatggattt atcctggaag cactaatact aagtataatg       240
agaagttctg ggacaggcca cattgactgt ggacacatcc tccaacacag cctacatgga       300
gctcaggggt ctgacctctg aggactctgc ggtctatttc tgtgaaatgg ggactcacta       360
tagttacgat gttatggact atggggtcaa ggaacctcag tcaccgtctc ctca            414
```

-continued

<210> SEQ ID NO 190
<211> LENGTH: 15
<212> TYPE: DNA
<213> ORGANISM: Artificial Sequence
<220> FEATURE:
<223> OTHER INFORMATION: DNA sequence of heavy chain CDR1 of monoclonal
      antibody 179 9E12

<400> SEQUENCE: 190
aactcctata taaac                                                      15

<210> SEQ ID NO 191
<211> LENGTH: 51
<212> TYPE: DNA
<213> ORGANISM: Artificial Sequence
<220> FEATURE:
<223> OTHER INFORMATION: DNA sequence of heavy chain CDR2 of monoclonal
      antibody 179 9E12

<400> SEQUENCE: 191
tggatttatc ctggaagcac taatactaag tataatgaga agttctggga c              51

<210> SEQ ID NO 192
<211> LENGTH: 33
<212> TYPE: DNA
<213> ORGANISM: Artificial Sequence
<220> FEATURE:
<223> OTHER INFORMATION: DNA sequence of heavy chain CDR3 of monoclonal
      antibody 179 9E12

<400> SEQUENCE: 192
gggactcact atagttacga tgttatggac tac                                  33

<210> SEQ ID NO 193
<211> LENGTH: 379
<212> TYPE: DNA
<213> ORGANISM: Artificial Sequence
<220> FEATURE:
<223> OTHER INFORMATION: DNA sequence of light chain of monoclonal
      antibody 179 9E12

<400> SEQUENCE: 193
atggagtttc agacccaggt ctttgtattc gtgttgctct ggttgtctgg tgttgatgga     60
gacattgtga tgacccogtc tcaaaaattc atgtccacat cagtaggaga cagggtcagc    120
atcacctcaa ggccagtcag aatgttcgta cttctgtagg ctggtatcaa cagaaaccag    180
ggcagtctcc taaaccactg atttacgcga catccaaccg gcacactgga gtccctgatc    240
gcttcacagg cagtgatctg ggacagattt cagtctcacc attaccaatg tgcaatctga    300
agaccaggca gattatttct gtctgcagca ttggaattat ccgtggacgt tcggtggagg    360
caccaagctg gaaatcaaa                                                 379

<210> SEQ ID NO 194
<211> LENGTH: 33
<212> TYPE: DNA
<213> ORGANISM: Artificial Sequence
<220> FEATURE:
<223> OTHER INFORMATION: DNA sequence of light chain CDR1 of monoclonal
      antibody 179 9E12

<400> SEQUENCE: 194
aaggccagtc agaatgttcg tacttctgta ggc                                  33

```
<210> SEQ ID NO 195
<211> LENGTH: 21
<212> TYPE: DNA
<213> ORGANISM: Artificial Sequence
<220> FEATURE:
<223> OTHER INFORMATION: DNA sequence of light chain CDR2 of monoclonal
      antibody 179 9E12

<400> SEQUENCE: 195
gcgacatcca accggcacac t                                            21

<210> SEQ ID NO 196
<211> LENGTH: 27
<212> TYPE: DNA
<213> ORGANISM: Artificial Sequence
<220> FEATURE:
<223> OTHER INFORMATION: DNA sequence of light chain CDR3 of monoclonal
      antibody 179 9E12

<400> SEQUENCE: 196
ctgcagcatt ggaattatcc gtggacg                                      27

<210> SEQ ID NO 197
<211> LENGTH: 119
<212> TYPE: PRT
<213> ORGANISM: Artificial Sequence
<220> FEATURE:
<223> OTHER INFORMATION: Amino acid sequence of heavy chain variable
      region of monoclonal antibody 179 9E12

<400> SEQUENCE: 197

Gln Ile Gln Leu Gln Gln Ser Gly Pro Glu Leu Val Lys Pro Gly Ala
1               5                   10                  15

Ser Val Lys Ile Ser Cys Lys Ala Ser Asp Tyr Ser Phe Thr Asn Ser
            20                  25                  30

Tyr Ile Asn Trp Val Lys Gln Arg Pro Gly Gln Gly Leu Glu Trp Ile
        35                  40                  45

Gly Trp Ile Tyr Pro Gly Ser Thr Asn Thr Lys Tyr Asn Glu Lys Phe
    50                  55                  60

Trp Asp Lys Ala Thr Leu Thr Val Asp Thr Ser Ser Asn Thr Ala Tyr
65                  70                  75                  80

Met Glu Leu Arg Gly Leu Thr Ser Glu Asp Ser Ala Val Tyr Phe Cys
                85                  90                  95

Glu Met Gly Thr His Tyr Ser Tyr Asp Val Met Asp Trp Gly Gln Gly
            100                 105                 110

Thr Ser Val Thr Val Ser Ser
        115

<210> SEQ ID NO 198
<211> LENGTH: 107
<212> TYPE: PRT
<213> ORGANISM: Artificial Sequence
<220> FEATURE:
<223> OTHER INFORMATION: Amino acid sequence of light chain variable
      region of monoclonal antibody 179 9E12

<400> SEQUENCE: 198

Asp Ile Val Met Thr Pro Ser Gln Lys Phe Met Ser Thr Ser Val Gly
1               5                   10                  15

Asp Arg Val Ser Ile Thr Cys Lys Ala Ser Gln Asn Val Arg Thr Ser
            20                  25                  30

Val Gly Trp Tyr Gln Gln Lys Pro Gly Gln Ser Pro Lys Pro Leu Ile
        35                  40                  45
```

Tyr Ala Thr Ser Asn Arg His Thr Gly Val Pro Asp Arg Phe Thr Gly
            50                  55                  60

Ser Gly Ser Gly Thr Asp Phe Ser Leu Thr Ile Thr Asn Val Gln Ser
 65                  70                  75                  80

Glu Asp Gln Ala Asp Tyr Phe Cys Leu Gln His Trp Asn Tyr Pro Trp
                 85                  90                  95

Thr Phe Gly Gly Gly Thr Lys Leu Glu Ile Lys
            100                 105

<210> SEQ ID NO 199
<211> LENGTH: 357
<212> TYPE: DNA
<213> ORGANISM: Artificial Sequence
<220> FEATURE:
<223> OTHER INFORMATION: DNA sequence of heavy chain variable region of
      monoclonal antibody 179 9E12

<400> SEQUENCE: 199
cagatccagc tgcagcagtc tggacctgag ttggtgaagc ctggggcttc agtgaagata      60
tcctgcaagg ttctgactac agcttcacta actcctatat aaactgggtg aagcagaggc    120
ctggacaggg acttgagtgg attggatgga tttatcctgg aagcactaat actaagtata    180
atgagaagtt ctgggacagg ccacattgac tgtggacaca tcctccaaca cagcctacat    240
ggagctcagg ggtctgacct ctgaggactc tgcggtctat ttctgtgaaa tggggactca    300
ctatagttac gatgttatgg actatggggt caaggaacct cagtcaccgt ctcctca       357

<210> SEQ ID NO 200
<211> LENGTH: 319
<212> TYPE: DNA
<213> ORGANISM: Artificial Sequence
<220> FEATURE:
<223> OTHER INFORMATION: DNA sequence of light chain variable region of
      monoclonal antibody 179 9E12

<400> SEQUENCE: 200
gacattgtga tgaccccgtc tcaaaaattc atgtccacat cagtaggaga cagggtcagc      60
atcacctcaa ggccagtcag aatgttcgta cttctgtagg ctggtatcaa cagaaaccag    120
ggcagtctcc taaaccactg atttacgcga catccaaccg gcacactgga gtccctgatc    180
gcttcacagg cagtgatctg ggacagattt cagtctcacc attaccaatg tgcaatctga    240
agaccaggca gattatttct gtctgcagca ttggaattat ccgtggacgt cggtggagg     300 caccaagctg gaaatcaaa                                                  319

<210> SEQ ID NO 201
<211> LENGTH: 138
<212> TYPE: PRT
<213> ORGANISM: Artificial Sequence
<220> FEATURE:
<223> OTHER INFORMATION: Amino acid sequence of heavy chain of
      monoclonal antibody 179B 10A7

<400> SEQUENCE: 201

Met Gly Trp Ser Trp Ile Phe Leu Phe Leu Leu Ser Gly Thr Ala Gly
  1               5                  10                  15

Val His Cys Gln Ile Gln Leu Gln Gln Ser Gly Pro Glu Leu Val Lys
                 20                  25                  30

Pro Gly Ala Ser Val Lys Ile Ser Cys Lys Ala Ser Asp Tyr Ser Phe
             35                  40                  45

Thr Lys Ser Tyr Ile Asn Trp Val Lys Gln Arg Pro Gly Gln Gly Leu
    50                  55                  60

Glu Trp Ile Gly Trp Ile Tyr Pro Gly Ser Ala Asn Ile Lys Tyr Asn
65                  70                  75                  80

Glu Lys Phe Arg Asp Lys Ala Thr Leu Thr Val Asp Thr Ser Ser Asn
                85                  90                  95

Thr Ala Tyr Ile Gln Leu Ser Ser Leu Thr Ser Glu Asp Ser Ala Val
            100                 105                 110

Tyr Phe Cys Glu Met Gly Thr His Tyr Thr Tyr Asp Val Met Asp Trp
        115                 120                 125

Gly Gln Gly Thr Ser Val Thr Val Ser Ser
    130                 135

<210> SEQ ID NO 202
<211> LENGTH: 5
<212> TYPE: PRT
<213> ORGANISM: Artificial Sequence
<220> FEATURE:
<223> OTHER INFORMATION: Amino acid sequence of heavy chain CDR1 of
      monoclonal antibody 179B 10A7

<400> SEQUENCE: 202

Lys Ser Tyr Ile Asn
1               5

<210> SEQ ID NO 203
<211> LENGTH: 17
<212> TYPE: PRT
<213> ORGANISM: Artificial Sequence
<220> FEATURE:
<223> OTHER INFORMATION: Amino acid sequence of heavy chain CDR2 of
      monoclonal antibody 179B 10A7

<400> SEQUENCE: 203

Trp Ile Tyr Pro Gly Ser Ala Asn Ile Lys Tyr Asn Glu Lys Phe Arg
1               5                   10                  15

Asp

<210> SEQ ID NO 204
<211> LENGTH: 11
<212> TYPE: PRT
<213> ORGANISM: Artificial Sequence
<220> FEATURE:
<223> OTHER INFORMATION: Amino acid sequence of heavy chain CDR3 of
      monoclonal antibody 179B 10A7

<400> SEQUENCE: 204

Gly Thr His Tyr Thr Tyr Asp Val Met Asp Tyr
1               5                   10

<210> SEQ ID NO 205
<211> LENGTH: 127
<212> TYPE: PRT
<213> ORGANISM: Artificial Sequence
<220> FEATURE:
<223> OTHER INFORMATION: Amino acid sequence of light chain of
      monoclonal antibody 179B 10A7

<400> SEQUENCE: 205

Met Glu Phe Gln Thr Gln Val Phe Val Phe Val Leu Leu Trp Leu Ser
1               5                   10                  15

Gly Val Asp Gly Asp Ile Val Met Thr Pro Ser Gln Lys Phe Met Ser
            20                  25                  30

```
Thr Ser Val Gly Asp Arg Val Ser Ile Thr Cys Lys Ala Ser Gln Asn
            35                  40                  45

Val Arg Thr Ser Val Gly Trp Tyr Gln Gln Lys Pro Gly Gln Ser Pro
 50                  55                  60

Lys Pro Leu Ile Tyr Ala Ala Ser Asn Arg His Thr Gly Val Pro Asp
 65              70                  75                  80

Arg Phe Thr Gly Ser Gly Ser Gly Thr Asp Phe Ser Leu Thr Ile Thr
                 85                  90                  95

Asn Val Gln Ser Glu Asp Gln Ala Asp Tyr Phe Cys Leu Gln His Trp
             100                 105                 110

Asn Tyr Pro Trp Thr Phe Gly Gly Gly Thr Lys Leu Glu Ile Lys
         115                 120                 125
```

<210> SEQ ID NO 206
<211> LENGTH: 11
<212> TYPE: PRT
<213> ORGANISM: Artificial Sequence
<220> FEATURE:
<223> OTHER INFORMATION: Amino acid sequence of light chain CDR1 of
      monoclonal antibody 179B 10A7

<400> SEQUENCE: 206

```
Lys Ala Ser Gln Asn Val Arg Thr Ser Val Gly
 1               5                  10
```

<210> SEQ ID NO 207
<211> LENGTH: 7
<212> TYPE: PRT
<213> ORGANISM: Artificial Sequence
<220> FEATURE:
<223> OTHER INFORMATION: Amino acid sequence of light chain CDR2 of
      monoclonal antibody 179B 10A7

<400> SEQUENCE: 207

```
Ala Ala Ser Asn Arg His Thr
 1               5
```

<210> SEQ ID NO 208
<211> LENGTH: 9
<212> TYPE: PRT
<213> ORGANISM: Artificial Sequence
<220> FEATURE:
<223> OTHER INFORMATION: Amino acid sequence of light chain CDR3 of
      monoclonal antibody 179B 10A7

<400> SEQUENCE: 208

```
Leu Gln His Trp Asn Tyr Pro Trp Thr
 1               5
```

<210> SEQ ID NO 209
<211> LENGTH: 414
<212> TYPE: DNA
<213> ORGANISM: Artificial Sequence
<220> FEATURE:
<223> OTHER INFORMATION: DNA sequence of heavy chain of monoclonal
      antibody 179B 10A7

<400> SEQUENCE: 209

```
atgggatgga gctggatctt tcttttcctc ctgtcaggaa ctgcaggtgt ccattgccag     60
atccagctgc agcagtctgg acctgagttg gtgaagcctg ggcttcagt gaagatatcc    120 tgcaaggttc tgactacagc ttcactaagt cctatataaa ctgggtgaag cagaggcctg    180
gacagggact tgagtggatt ggatggattt atcctggaag cgcaaatatt aaatataatg    240
```

```
agaagttcag ggacaggcca cattgactgt agacacatcc tccaacacag cctacataca      300
actcagcagt ctgacctctg aggactctgc ggtctatttc tgtgaaatgg ggactcacta      360
tacttacgat gttatggact atggggtcaa ggaacctcag tcaccgtctc ctca            414

<210> SEQ ID NO 210
<211> LENGTH: 15
<212> TYPE: DNA
<213> ORGANISM: Artificial Sequence
<220> FEATURE:
<223> OTHER INFORMATION: DNA sequence of heavy chain CDR1 of monoclonal
      antibody 179B 10A7

<400> SEQUENCE: 210
aagtcctata taaac                                                        15

<210> SEQ ID NO 211
<211> LENGTH: 51
<212> TYPE: DNA
<213> ORGANISM: Artificial Sequence
<220> FEATURE:
<223> OTHER INFORMATION: DNA sequence of heavy chain CDR2 of monoclonal
      antibody 179B 10A7

<400> SEQUENCE: 211
tggatttatc ctggaagcgc aaatattaaa tataatgaga agttcaggga c                51

<210> SEQ ID NO 212
<211> LENGTH: 33
<212> TYPE: DNA
<213> ORGANISM: Artificial Sequence
<220> FEATURE:
<223> OTHER INFORMATION: DNA sequence of heavy chain CDR3 of monoclonal
      antibody 179B 10A7

<400> SEQUENCE: 212
gggactcact atacttacga tgttatggac tac                                    33

<210> SEQ ID NO 213
<211> LENGTH: 379
<212> TYPE: DNA
<213> ORGANISM: Artificial Sequence
<220> FEATURE:
<223> OTHER INFORMATION: DNA sequence of light chain of monoclonal
      antibody 179B 10A7

<400> SEQUENCE: 213
atggagtttc agacccaggt ctttgtattc gtgttgctct ggttgtctgg tgttgatgga       60
gacattgtga tgaccccgtc tcaaaaattc atgtccacat cagttggaga cagggtcagc      120
atcaccttaa ggccagtcag aatgttcgta cttctgtagg ctggtatcaa cagaaaccag      180
ggcagtctcc taaaccactg atttacgcgg catccaaccg gcacactgga gtccctgatc      240
gcttcacagg cagtgatctg ggacagactt cagtctcacc attaccaatg tgcaatctga      300
agaccaggca gattatttct gtctgcaaca ttggaattat ccgtggacgt tcggtggagg      360
caccaagctg gaaatcaaa                                                   379

<210> SEQ ID NO 214
<211> LENGTH: 33
<212> TYPE: DNA
<213> ORGANISM: Artificial Sequence
<220> FEATURE:
<223> OTHER INFORMATION: DNA sequence of light chain CDR1 of monoclonal
      antibody 179B 10A7
```

<400> SEQUENCE: 214
aaggccagtc agaatgttcg tacttctgta ggc                     33

<210> SEQ ID NO 215
<211> LENGTH: 21
<212> TYPE: DNA
<213> ORGANISM: Artificial Sequence
<220> FEATURE:
<223> OTHER INFORMATION: DNA sequence of light chain CDR2 of monoclonal
      antibody 179B 10A7

<400> SEQUENCE: 215
gcggcatcca accggcacac t                                  21

<210> SEQ ID NO 216
<211> LENGTH: 27
<212> TYPE: DNA
<213> ORGANISM: Artificial Sequence
<220> FEATURE:
<223> OTHER INFORMATION: DNA sequence of light chain CDR3 of monoclonal
      antibody 179B 10A7

<400> SEQUENCE: 216
ctgcaacatt ggaattatcc gtggacg                            27

<210> SEQ ID NO 217
<211> LENGTH: 119
<212> TYPE: PRT
<213> ORGANISM: Artificial Sequence
<220> FEATURE:
<223> OTHER INFORMATION: Amino acid sequence of heavy chain variable
      region of monoclonal antibody 179B 10A7

<400> SEQUENCE: 217

Gln Ile Gln Leu Gln Gln Ser Gly Pro Glu Leu Val Lys Pro Gly Ala
1               5                   10                  15

Ser Val Lys Ile Ser Cys Lys Ala Ser Asp Tyr Ser Phe Thr Lys Ser
            20                  25                  30

Tyr Ile Asn Trp Val Lys Gln Arg Pro Gly Gln Gly Leu Glu Trp Ile
        35                  40                  45

Gly Trp Ile Tyr Pro Gly Ser Ala Asn Ile Lys Tyr Asn Glu Lys Phe
    50                  55                  60

Arg Asp Lys Ala Thr Leu Thr Val Asp Thr Ser Ser Asn Thr Ala Tyr
65                  70                  75                  80

Ile Gln Leu Ser Ser Leu Thr Ser Glu Asp Ser Ala Val Tyr Phe Cys
                85                  90                  95

Glu Met Gly Thr His Tyr Thr Tyr Asp Val Met Asp Trp Gly Gln Gly
            100                 105                 110

Thr Ser Val Thr Val Ser Ser
        115

<210> SEQ ID NO 218
<211> LENGTH: 107
<212> TYPE: PRT
<213> ORGANISM: Artificial Sequence
<220> FEATURE:
<223> OTHER INFORMATION: Amino acid sequence of light chain variable
      region of monoclonal antibody 179B 10A7

<400> SEQUENCE: 218

Asp Ile Val Met Thr Pro Ser Gln Lys Phe Met Ser Thr Ser Val Gly
1               5                   10                  15

```
Asp Arg Val Ser Ile Thr Cys Lys Ala Ser Gln Asn Val Arg Thr Ser
            20                  25                  30

Val Gly Trp Tyr Gln Gln Lys Pro Gly Gln Ser Pro Lys Pro Leu Ile
        35                  40                  45

Tyr Ala Ala Ser Asn Arg His Thr Gly Val Pro Asp Arg Phe Thr Gly
    50                  55                  60

Ser Gly Ser Gly Thr Asp Phe Ser Leu Thr Ile Thr Asn Val Gln Ser
65                  70                  75                  80

Glu Asp Gln Ala Asp Tyr Phe Cys Leu Gln His Trp Asn Tyr Pro Trp
                85                  90                  95

Thr Phe Gly Gly Gly Thr Lys Leu Glu Ile Lys
            100                 105
```

<210> SEQ ID NO 219
<211> LENGTH: 357
<212> TYPE: DNA
<213> ORGANISM: Artificial Sequence
<220> FEATURE:
<223> OTHER INFORMATION: DNA sequence of heavy chain variable region of
      monoclonal antibody 179B 10A7

<400> SEQUENCE: 219

```
cagatccagc tgcagcagtc tggacctgag ttggtgaagc ctggggcttc agtgaagata      60
tcctgcaagg ttctgactac agcttcacta gtcctatat aaactgggtg aagcagaggc     120
ctggacaggg acttgagtgg attggatgga tttatcctgg aagcgcaaat attaaatata    180
atgagaagtt cagggacagg ccacattgac tgtagacaca tcctccaaca cagcctacat    240
acaactcagc agtctgacct ctgaggactc tgcggtctat ttctgtgaaa tggggactca    300
ctatacttac gatgttatgg actatgggt caaggaacct cagtcaccgt ctcctca       357
```

<210> SEQ ID NO 220
<211> LENGTH: 319
<212> TYPE: DNA
<213> ORGANISM: Artificial Sequence
<220> FEATURE:
<223> OTHER INFORMATION: DNA sequence of light chain variable region of
      monoclonal antibody 179B 10A7

<400> SEQUENCE: 220

```
gacattgtga tgacccgtc tcaaaaattc atgtccacat cagttggaga cagggtcagc      60
atcaccttaa ggccagtcag aatgttcgta cttctgtagg ctggtatcaa cagaaaccag    120
ggcagtctcc taaaccactg atttacgcgg catccaaccg gcacactgga gtccctgatc    180
gcttcacagg cagtgatctg gacagactt cagtctcacc attaccaatg tgcaatctga    240
agaccaggca gattatttct gtctgcaaca ttggaattat ccgtggacgt tcggtggagg    300
caccaagctg gaaatcaaa                                                  319
```

<210> SEQ ID NO 221
<211> LENGTH: 135
<212> TYPE: PRT
<213> ORGANISM: Artificial Sequence
<220> FEATURE:
<223> OTHER INFORMATION: Amino acid sequence of heavy chain of
      monoclonal antibody 179A 6H6

<400> SEQUENCE: 221

```
Met Tyr Leu Gly Leu Asn Cys Val Ile Ile Val Phe Leu Leu Lys Gly
1               5                   10                  15
```

-continued

```
Val Gln Ser Glu Val Lys Leu Glu Glu Ser Gly Gly Gly Leu Val Pro
            20                  25                  30

Pro Gly Gly Ser Met Lys Leu Ser Cys Ser Val Ser Gly Phe Thr Phe
        35                  40                  45

Ser Asp Ala Trp Ile Asp Trp Val Arg Gln Ser Pro Glu Lys Gly Leu
    50                  55                  60

Glu Trp Ile Ala Glu Ser Arg Asn Lys Ala Asn Asn Tyr Ala Ile Tyr
65                  70                  75                  80

Tyr Thr Glu Ser Val Lys Gly Arg Phe Thr Ile Ser Arg Asp Asp Ser
                85                  90                  95

Lys Ser Arg Val Tyr Leu Gln Met Asn Asn Leu Arg Val Glu Asp Thr
            100                 105                 110

Gly Ile Tyr Tyr Cys Thr Gly Pro Asp Tyr Asp Ser Tyr Trp Gly Gly
        115                 120                 125

Thr Leu Val Thr Val Ser Ala
    130                 135

<210> SEQ ID NO 222
<211> LENGTH: 5
<212> TYPE: PRT
<213> ORGANISM: Artificial Sequence
<220> FEATURE:
<223> OTHER INFORMATION: Amino acid sequence of heavy chain CDR1 of
      monoclonal antibody 179A 6H6

<400> SEQUENCE: 222

Asp Ala Trp Ile Asp
1               5

<210> SEQ ID NO 223
<211> LENGTH: 19
<212> TYPE: PRT
<213> ORGANISM: Artificial Sequence
<220> FEATURE:
<223> OTHER INFORMATION: Amino acid sequence of heavy chain CDR2 of
      monoclonal antibody 179A 6H6

<400> SEQUENCE: 223

Glu Ser Arg Asn Lys Ala Asn Asn Tyr Ala Ile Tyr Tyr Thr Glu Ser
1               5                   10                  15

Val Lys Gly

<210> SEQ ID NO 224
<211> LENGTH: 6
<212> TYPE: PRT
<213> ORGANISM: Artificial Sequence
<220> FEATURE:
<223> OTHER INFORMATION: Amino acid sequence of heavy chain CDR3 of
      monoclonal antibody 179A 6H6

<400> SEQUENCE: 224

Pro Asp Tyr Asp Ser Tyr
1               5

<210> SEQ ID NO 225
<211> LENGTH: 127
<212> TYPE: PRT
<213> ORGANISM: Artificial Sequence
<220> FEATURE:
<223> OTHER INFORMATION: Amino acid sequence of light chain of
      monoclonal antibody 179A 6H6
```

<400> SEQUENCE: 225

Met Glu Phe Gln Thr Gln Val Phe Val Phe Val Leu Leu Trp Leu Ser
1               5                   10                  15

Gly Val Asp Gly Asp Val Val Met Thr Gln Ser Gln Lys Ile Met Ser
            20                  25                  30

Thr Ser Val Gly Asp Arg Val Ser Ile Thr Cys Lys Ala Ser Gln Asn
        35                  40                  45

Val Arg Thr Ala Val Thr Trp Tyr Gln Leu Lys Pro Gly Gln Ser Pro
    50                  55                  60

Lys Ala Leu Ile Tyr Leu Ala Ser Asn Arg His Thr Gly Val Pro Asp
65                  70                  75                  80

Arg Phe Arg Gly Ser Gly Ser Gly Thr Asp Phe Thr Leu Thr Ile Ile
                85                  90                  95

Asn Val Gln Ser Glu Asp Leu Ala Asp Tyr Phe Cys Leu Gln His Trp
            100                 105                 110

Asn Tyr Pro Leu Thr Phe Gly Ala Gly Thr Lys Leu Glu Leu Lys
        115                 120                 125

<210> SEQ ID NO 226
<211> LENGTH: 11
<212> TYPE: PRT
<213> ORGANISM: Artificial Sequence
<220> FEATURE:
<223> OTHER INFORMATION: Amino acid sequence of light chain CDR1 of
      monoclonal antibody 179A 6H6

<400> SEQUENCE: 226

Lys Ala Ser Gln Asn Val Arg Thr Ala Val Thr
1               5                   10

<210> SEQ ID NO 227
<211> LENGTH: 7
<212> TYPE: PRT
<213> ORGANISM: Artificial Sequence
<220> FEATURE:
<223> OTHER INFORMATION: Amino acid sequence of light chain CDR2 of
      monoclonal antibody 179A 6H6

<400> SEQUENCE: 227

Leu Ala Ser Asn Arg His Thr
1               5

<210> SEQ ID NO 228
<211> LENGTH: 9
<212> TYPE: PRT
<213> ORGANISM: Artificial Sequence
<220> FEATURE:
<223> OTHER INFORMATION: Amino acid sequence of light chain CDR3 of
      monoclonal antibody 179A 6H6

<400> SEQUENCE: 228

Leu Gln His Trp Asn Tyr Pro Leu Thr
1               5

<210> SEQ ID NO 229
<211> LENGTH: 405
<212> TYPE: DNA
<213> ORGANISM: Artificial Sequence
<220> FEATURE:
<223> OTHER INFORMATION: DNA sequence of heavy chain of monoclonal
      antibody 179A 6H6

<400> SEQUENCE: 229

```
atgtacttgg gactgaactg tgtaatcata gttttctct taaaaggtgt ccagagtgaa      60
gtgaagcttg aggagtctgg aggaggcttg gtgccacctg gaggatccat gaaactctct     120
tgttctgttc tggattcact tttagtgatg cctggataga ctgggtccgc cagtctccag     180
agaaggggct tgagtggatt gctgaaagtc gaaacaaagc taataattat gcaatatatt     240
acactgagtc tgtgaagggc ggttcaccat ctcaagagat gattccaaaa gtagagtgta     300
cctgcaaatg aacaacttaa gagttgaaga cactggcatt tattactgta ccgggccgga     360
ttacgactct tactggggcc aggactctg gtcactgtct ctgca                     405
```

<210> SEQ ID NO 230
<211> LENGTH: 15
<212> TYPE: DNA
<213> ORGANISM: Artificial Sequence
<220> FEATURE:
<223> OTHER INFORMATION: DNA sequence of heavy chain CDR1 of monoclonal antibody 179A 6H6

<400> SEQUENCE: 230

```
gatgcctgga tagac                                                      15
```

<210> SEQ ID NO 231
<211> LENGTH: 56
<212> TYPE: DNA
<213> ORGANISM: Artificial Sequence
<220> FEATURE:
<223> OTHER INFORMATION: DNA sequence of heavy chain CDR2 of monoclonal antibody 179A 6H6

<400> SEQUENCE: 231

```
gaaagtcgaa acaaagctaa taattatgca atatattaca ctgagtctgt gaaggg         56
```

<210> SEQ ID NO 232
<211> LENGTH: 18
<212> TYPE: DNA
<213> ORGANISM: Artificial Sequence
<220> FEATURE:
<223> OTHER INFORMATION: DNA sequence of heavy chain CDR3 of monoclonal antibody 179A 6H6

<400> SEQUENCE: 232

```
ccggattacg actcttac                                                   18
```

<210> SEQ ID NO 233
<211> LENGTH: 379
<212> TYPE: DNA
<213> ORGANISM: Artificial Sequence
<220> FEATURE:
<223> OTHER INFORMATION: DNA sequence of light chain of monoclonal antibody 179A 6H6

<400> SEQUENCE: 233

```
atggagtttc agacccaggt ctttgtattc gtgttgctct ggttgtctgg tgttgatgga      60
gacgttgtga tgacccagtc tcaaaaaatc atgtccacat cagtaggaga cagggtcagc     120
atcacctcaa ggccagtcag aatgttcgta ctgctgttac tggtatcaa ctgaaaccag      180 gtcagtctcc taaagcactg atttacttgg catccaaccg gcacactgga gtccctgatc     240
```

```
gctttagagg cagtgatctg ggacagattt cactcttacc attatcaatg tgcaatctga    300
ggacctggca gattatttct gtctgcaaca ttggaattat cctctcacgt tcggtgctgg    360
gaccaagctg gagttgaaa                                                  379
```

<210> SEQ ID NO 234
<211> LENGTH: 33
<212> TYPE: DNA
<213> ORGANISM: Artificial Sequence
<220> FEATURE:
<223> OTHER INFORMATION: DNA sequence of light chain CDR1 of monoclonal antibody 179A 6H6

<400> SEQUENCE: 234

```
aaggccagtc agaatgttcg tactgctgtt acc                                   33
```

<210> SEQ ID NO 235
<211> LENGTH: 21
<212> TYPE: DNA
<213> ORGANISM: Artificial Sequence
<220> FEATURE:
<223> OTHER INFORMATION: DNA sequence of light chain CDR2 of monoclonal antibody 179A 6H6

<400> SEQUENCE: 235

```
ttggcatcca accggcacac t                                                21
```

<210> SEQ ID NO 236
<211> LENGTH: 27
<212> TYPE: DNA
<213> ORGANISM: Artificial Sequence
<220> FEATURE:
<223> OTHER INFORMATION: DNA sequence of light chain CDR3 of monoclonal antibody 179A 6H6

<400> SEQUENCE: 236

```
ctgcaacatt ggaattatcc tctcacg                                          27
```

<210> SEQ ID NO 237
<211> LENGTH: 116
<212> TYPE: PRT
<213> ORGANISM: Artificial Sequence
<220> FEATURE:
<223> OTHER INFORMATION: Amino acid sequence of heavy chain variable region of monoclonal antibody 179A 6H6

<400> SEQUENCE: 237

```
Glu Val Lys Leu Glu Glu Ser Gly Gly Gly Leu Val Pro Pro Gly Gly
1               5                   10                  15

Ser Met Lys Leu Ser Cys Ser Val Ser Gly Phe Thr Phe Ser Asp Ala
            20                  25                  30

Trp Ile Asp Trp Val Arg Gln Ser Pro Glu Lys Gly Leu Glu Trp Ile
        35                  40                  45

Ala Glu Ser Arg Asn Lys Ala Asn Asn Tyr Ala Ile Tyr Tyr Thr Glu
    50                  55                  60

Ser Val Lys Gly Arg Phe Thr Ile Ser Arg Asp Asp Ser Lys Ser Arg
65                  70                  75                  80

Val Tyr Leu Gln Met Asn Asn Leu Arg Val Glu Asp Thr Gly Ile Tyr
                85                  90                  95
```

Tyr Cys Thr Gly Pro Asp Tyr Asp Ser Tyr Trp Gly Gly Thr Leu Val
            100                 105                 110

Thr Val Ser Ala
        115

<210> SEQ ID NO 238
<211> LENGTH: 107
<212> TYPE: PRT
<213> ORGANISM: Artificial Sequence
<220> FEATURE:
<223> OTHER INFORMATION: Amino acid sequence of  light chain variable of
      monoclonal antibody 179A 6H6

<400> SEQUENCE: 238

Asp Val Val Met Thr Gln Ser Gln Lys Ile Met Ser Thr Ser Val Gly
1               5                   10                  15

Asp Arg Val Ser Ile Thr Cys Lys Ala Ser Gln Asn Val Arg Thr Ala
            20                  25                  30

Val Thr Trp Tyr Gln Leu Lys Pro Gly Gln Ser Pro Lys Ala Leu Ile
        35                  40                  45

Tyr Leu Ala Ser Asn Arg His Thr Gly Val Pro Asp Arg Phe Arg Gly
    50                  55                  60

Ser Gly Ser Gly Thr Asp Phe Thr Leu Thr Ile Ile Asn Val Gln Ser
65                  70                  75                  80

Glu Asp Leu Ala Asp Tyr Phe Cys Leu Gln His Trp Asn Tyr Pro Leu
                85                  90                  95

Thr Phe Gly Ala Gly Thr Lys Leu Glu Leu Lys
            100                 105

<210> SEQ ID NO 239
<211> LENGTH: 278
<212> TYPE: DNA
<213> ORGANISM: Artificial Sequence
<220> FEATURE:
<223> OTHER INFORMATION: DNA sequence of heavy chain variable region of
      monoclonal antibody 179A 6H6

<400> SEQUENCE: 239
ttctggattc acttttagtg atgcctggat agactgggtc cgccagtctc cagagaaggg      60
gcttgagtgg attgctgaaa gtcgaaacaa agctaataat tatgcaatat attacactga     120
gtctgtgaag ggcggttcac catctcaaga tgattccaa aaagtagagt gtacctgcaa     180
atgaacaact taagagttga agacactggc atttattact gtaccgggcc ggattacgac     240
tcttactggg gccagggact ctggtcactg tctctgca                            278

<210> SEQ ID NO 240
<211> LENGTH: 319
<212> TYPE: DNA
<213> ORGANISM: Artificial Sequence
<220> FEATURE:
<223> OTHER INFORMATION: DNA sequence of light chain variable region of
      monoclonal antibody 179A 6H6

<400> SEQUENCE: 240
gacgttgtga tgacccagtc tcaaaaaatc atgtccacat cagtaggaga cagggtcagc      60
atcacctcaa ggccagtcag aatgttcgta ctgctgttac ctggtatcaa ctgaaaccag     120
gtcagtctcc taaagcactg atttacttgg catccaaccg gcacactgga gtccctgatc     180
gctttagagg cagtgatctg gacagattt cactcttacc attatcaatg tgcaatctga     240

```
ggacctggca gattatttct gtctgcaaca ttggaattat cctctcacgt tcggtgctgg    300
gaccaagctg gagttgaaa                                                 319
```

<210> SEQ ID NO 241
<211> LENGTH: 137
<212> TYPE: PRT
<213> ORGANISM: Artificial Sequence
<220> FEATURE:
<223> OTHER INFORMATION: Amino acid sequence of heavy chain of
      monoclonal antibody 179B 9E7

<400> SEQUENCE: 241

Met Tyr Leu Gly Leu Asn Cys Val Ile Ile Val Phe Leu Leu Lys Gly
1               5                   10                  15

Val Gln Ser Glu Met Lys Leu Glu Glu Ser Gly Gly Gly Leu Val Gln
            20                  25                  30

Pro Gly Gly Ser Met Lys Leu Ser Cys Thr Ala Ser Gly Phe Thr Phe
        35                  40                  45

Ser Asp Ala Trp Met Asp Trp Val Arg Gln Ser Pro Glu Lys Gly Leu
    50                  55                  60

Glu Trp Val Ala Glu Ile Arg Asn Lys Ala Tyr Asn His Ala Thr Tyr
65                  70                  75                  80

Tyr Ala Glu Ser Val Arg Gly Arg Phe Thr Ile Ser Arg Asp Asp Ser
                85                  90                  95

Lys Ser Lys Met Phe Leu Glu Met Asn Ser Leu Arg Pro Glu Asp Thr
            100                 105                 110

Gly Ile Tyr Tyr Cys Ile Gly Gly Ile Trp Thr Asp Phe Asp Tyr Gly
        115                 120                 125

Gln Gly Thr Thr Leu Thr Val Ser Ser
    130                 135

<210> SEQ ID NO 242
<211> LENGTH: 5
<212> TYPE: PRT
<213> ORGANISM: Artificial Sequence
<220> FEATURE:
<223> OTHER INFORMATION: Amino acid sequence of heavy chain CDR1 of
      monoclonal antibody 179B 9E7

<400> SEQUENCE: 242

Asp Ala Trp Met Asp
1               5

<210> SEQ ID NO 243
<211> LENGTH: 19
<212> TYPE: PRT
<213> ORGANISM: Artificial Sequence
<220> FEATURE:
<223> OTHER INFORMATION: Amino acid sequence of heavy chain CDR2 of
      monoclonal antibody 179B 9E7

<400> SEQUENCE: 243

Glu Ile Arg Asn Lys Ala Tyr Asn His Ala Thr Tyr Tyr Ala Glu Ser
1               5                   10                  15

Val Arg Gly

<210> SEQ ID NO 244
<211> LENGTH: 8
<212> TYPE: PRT
<213> ORGANISM: Artificial Sequence

```
<220> FEATURE:
<223> OTHER INFORMATION: Amino acid sequence of heavy chain CDR3 of
      monoclonal antibody 179B 9E7

<400> SEQUENCE: 244

Gly Ile Trp Thr Asp Phe Asp Tyr
1               5

<210> SEQ ID NO 245
<211> LENGTH: 127
<212> TYPE: PRT
<213> ORGANISM: Artificial Sequence
<220> FEATURE:
<223> OTHER INFORMATION: Amino acid sequence of light chain of
      monoclonal antibody 179B 9E7

<400> SEQUENCE: 245

Met Glu Ser Gln Thr Gln Val Phe Val Tyr Met Leu Leu Trp Leu Ser
1               5                   10                  15

Gly Val Asp Gly Asp Ile Val Met Thr Gln Ser Gln Lys Phe Met Ser
            20                  25                  30

Thr Ser Val Gly Asp Arg Val Ser Val Thr Cys Lys Ala Ser Gln Asn
        35                  40                  45

Val Gly Ile Asn Val Ala Trp Tyr Gln Gln Lys Ser Gly Gln Pro Pro
    50                  55                  60

Lys Ala Leu Ile Tyr Ser Ala Ser Ser Arg Tyr Ser Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Glu Tyr Phe Cys His Gln Tyr Asn
            100                 105                 110

Asn Tyr Pro Leu Thr Phe Gly Ala Gly Thr Lys Leu Asp Leu Lys
        115                 120                 125

<210> SEQ ID NO 246
<211> LENGTH: 11
<212> TYPE: PRT
<213> ORGANISM: Artificial Sequence
<220> FEATURE:
<223> OTHER INFORMATION: Amino acid sequence of light chain CDR1 of
      monoclonal antibody 179B 9E7

<400> SEQUENCE: 246

Lys Ala Ser Gln Asn Val Gly Ile Asn Val Ala
1               5                   10

<210> SEQ ID NO 247
<211> LENGTH: 7
<212> TYPE: PRT
<213> ORGANISM: artificial Sequence
<220> FEATURE:
<223> OTHER INFORMATION: Amino acid sequence of light chain CD2 of
      monoclonal antibody 179B 9E7

<400> SEQUENCE: 247

Ser Ala Ser Ser Arg Tyr Ser
1               5

<210> SEQ ID NO 248
<211> LENGTH: 9
<212> TYPE: PRT
<213> ORGANISM: Artificial Sequence
```

<220> FEATURE:
<223> OTHER INFORMATION: Amino acid sequence of light chain CDR3 of
      monoclonal antibody 179B 9E7

<400> SEQUENCE: 248

His Gln Tyr Asn Asn Tyr Pro Leu Thr
1               5

<210> SEQ ID NO 249
<211> LENGTH: 411
<212> TYPE: DNA
<213> ORGANISM: Artificial Sequence
<220> FEATURE:
<223> OTHER INFORMATION: DNA sequence of heavy chain of monoclonal
      antibody 179B 9E7

<400> SEQUENCE: 249
atgtacttgg gactgaactg tgtaatcata gttttctct taaaaggtgt ccagagtgaa      60
atgaagcttg aggagtctgg aggaggctta gtgcaacctg gaggatccat gaaactctcc     120
tgtactgttc tggattcact tttagtgatg cctggatgga ctgggtccgc cagtctccag     180
agaaggggct tgagtgggtt gctgagatta gaaacaaagc ttataatcat gcaacatatt     240
atgctgagtc tgtggaggga ggttcaccat ctccagagat gattccaaaa gtaaaatgtt     300
cctggaaatg aacagcttaa gacctgaaga cactggcatt tattattgta tcgggggggat    360 ttggacggac tttgactact gggccaaggc accactctca cagtctcctc a              411

<210> SEQ ID NO 250
<211> LENGTH: 15
<212> TYPE: DNA
<213> ORGANISM: Artificial Sequence
<220> FEATURE:
<223> OTHER INFORMATION: DNA sequence of heavy chain CDR1 of monoclonal
      antibody 179B 9E7

<400> SEQUENCE: 250
gatgcctgga tggac                                                       15

<210> SEQ ID NO 251
<211> LENGTH: 56
<212> TYPE: DNA
<213> ORGANISM: Artificial Sequence
<220> FEATURE:
<223> OTHER INFORMATION: DNA sequence of heavy chain CDR2 of monoclonal
      antibody 179B 9E7

<400> SEQUENCE: 251
gagattagaa acaaagctta taatcatgca acatattatg ctgagtctgt ggaggg          56

<210> SEQ ID NO 252
<211> LENGTH: 24
<212> TYPE: DNA
<213> ORGANISM: Artificial Sequence
<220> FEATURE:
<223> OTHER INFORMATION: DNA sequence of heavy chain CDR3 of monoclonal
      antibody 179B 9E7

<400> SEQUENCE: 252
gggatttgga cggactttga ctac                                             24

<210> SEQ ID NO 253
<211> LENGTH: 379
<212> TYPE: DNA
<213> ORGANISM: Artificial Sequence
<220> FEATURE:

<223> OTHER INFORMATION: DNA sequence of light chain of monoclonal
      antibody 179B 9E7

<400> SEQUENCE: 253
atggagtcac agactcaggt ctttgtatac atgttgctgt ggttgtctgg tgttgatgga    60
gacattgtga tgacccagtc tcaaaaattc atgtccacat cagtaggaga cagggtcagc   120
gtcacctcaa ggccagtcag aatgtgggta ttaatgtagc ctggtatcaa cagaaatcag   180
ggcaacctcc taaagcactg atttattcgg catcttcccg gtacagtgga gtccctgatc   240
gcttcacagg cagtgatctg ggacagattt cactctcacc atcagcaatg tgcagtctga   300
agacttggca gagtatttct gtcaccaata taataattat cctctcacgt tcggtgctgg   360
gaccaagctg gacctgaaa                                                 379

<210> SEQ ID NO 254
<211> LENGTH: 33
<212> TYPE: DNA
<213> ORGANISM: Artificial Sequence
<220> FEATURE:
<223> OTHER INFORMATION: DNA sequence of light chain CDR1 of monoclonal
      antibody 179B 9E7

<400> SEQUENCE: 254
aaggccagtc agaatgtggg tattaatgta gcc                                  33

<210> SEQ ID NO 255
<211> LENGTH: 21
<212> TYPE: DNA
<213> ORGANISM: Artificial Sequence
<220> FEATURE:
<223> OTHER INFORMATION: DNA sequence of light chain CDR2 of monoclonal
      antibody 179B 9E7

<400> SEQUENCE: 255
tcggcatctt cccggtacag t                                               21

<210> SEQ ID NO 256
<211> LENGTH: 27
<212> TYPE: DNA
<213> ORGANISM: Artificial Sequence
<220> FEATURE:
<223> OTHER INFORMATION: DNA sequence of light chain CDR3 of monoclonal
      antibody 179B 9E7

<400> SEQUENCE: 256
caccaatata ataattatcc tctcacg                                         27

<210> SEQ ID NO 257
<211> LENGTH: 118
<212> TYPE: PRT
<213> ORGANISM: Artificial Sequence
<220> FEATURE:
<223> OTHER INFORMATION: Amino acid sequence of heavy chain variable
      region of monoclonal antibody 179B 9E7

<400> SEQUENCE: 257

Glu Met Lys Leu Glu Glu Ser Gly Gly Gly Leu Val Gln Pro Gly Gly
1               5                   10                  15

Ser Met Lys Leu Ser Cys Thr Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Asn Lys Ala Tyr Asn His Ala Thr Tyr Tyr Ala Glu
            50                  55                  60

Ser Val Arg Gly Arg Phe Thr Ile Ser Arg Asp Asp Ser Lys Ser Lys
 65                  70                  75                  80

Met Phe Leu Glu Met Asn Ser Leu Arg Pro Glu Asp Thr Gly Ile Tyr
                85                  90                  95

Tyr Cys Ile Gly Gly Ile Trp Thr Asp Phe Asp Tyr Gly Gln Gly Thr
            100                 105                 110

Thr Leu Thr Val Ser Ser
        115

<210> SEQ ID NO 258
<211> LENGTH: 107
<212> TYPE: PRT
<213> ORGANISM: Artificial Sequence
<220> FEATURE:
<223> OTHER INFORMATION: Amino acid sequence of light chain variable
      region of monoclonal antibody 179B 9E7

<400> SEQUENCE: 258

Asp Ile Val Met Thr Gln Ser Gln Lys Phe Met Ser Thr Ser Val Gly
 1               5                  10                  15

Asp Arg Val Ser Val Thr Cys Lys Ala Ser Gln Asn Val Gly Ile Asn
                20                  25                  30

Val Ala Trp Tyr Gln Gln Lys Ser Gly Gln Pro Pro Lys Ala Leu Ile
            35                  40                  45

Tyr Ser Ala Ser Ser Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys His Gln Tyr Asn Asn Tyr Pro Leu
                85                  90                  95

Thr Phe Gly Ala Gly Thr Lys Leu Asp Leu Lys
            100                 105

<210> SEQ ID NO 259
<211> LENGTH: 354
<212> TYPE: DNA
<213> ORGANISM: Artificial Sequence
<220> FEATURE:
<223> OTHER INFORMATION: DNA sequence of heavy chain variable region of
      monoclonal antibody 179B 9E7

<400> SEQUENCE: 259
gaaatgaagc ttgaggagtc tggaggaggc ttagtgcaac ctggaggatc catgaaactc      60
tcctgtactg ttctggattc acttttagtg atgcctggat ggactgggtc cgccagtctc     120
cagagaaggg gcttgagtgg gttgctgaga ttagaaacaa agcttataat catgcaacat     180
attatgctga gtctgtggag ggaggttcac catctccaga tgattccaa aaagtaaaat      240 gttcctggaa atgaacagct taagacctga agacactggc atttattatt gtatcggggg     300
gatttggacg gactttgact actgggccaa ggcaccactc tcacagtctc ctca           354

<210> SEQ ID NO 260
<211> LENGTH: 319
<212> TYPE: DNA
<213> ORGANISM: Artificial Sequence
<220> FEATURE:
<223> OTHER INFORMATION: DNA sequence of light chain variable region of
      monoclonal antibody 179B 9E7

```
<400> SEQUENCE: 260
gacattgtga tgacccagtc tcaaaaattc atgtccacat cagtaggaga cagggtcagc        60
gtcacctcaa ggccagtcag aatgtgggta ttaatgtagc ctggtatcaa cagaaatcag       120
ggcaacctcc taaagcactg atttattcgg catcttcccg gtacagtgga gtccctgatc       180
gcttcacagg cagtgatctg ggacagattt cactctcacc atcagcaatg tgcagtctga       240
agacttggca gagtatttct gtcaccaata taataattat cctctcacgt tcggtgctgg       300
gaccaagctg gacctgaaa                                                    319
```